United States Patent
Ouchi

[19]

[11] Patent Number: 5,964,740
[45] Date of Patent: Oct. 12, 1999

[54] TREATMENT ACCESSORY FOR AN ENDOSCOPE

[75] Inventor: Teruo Ouchi, Tokyo, Japan

[73] Assignee: Asahi Kogaku Kogyo Kabushiki Kaisha, Tokyo, Japan

[21] Appl. No.: 08/835,234

[22] Filed: Apr. 7, 1997

[30] Foreign Application Priority Data

| Jul. 9, 1996 | [JP] | Japan | 8-178782 |
| Jul. 9, 1996 | [JP] | Japan | 8-178783 |
| Jul. 26, 1996 | [JP] | Japan | 8-197491 |
| Feb. 5, 1997 | [JP] | Japan | 9-022267 |

[51] Int. Cl.[6] ................................. A61M 5/00
[52] U.S. Cl. .................. 604/264; 606/185; 604/164
[58] Field of Search .................... 604/164–170, 604/117, 192, 198, 263–264, 272, 283, 280, 157, 533; 606/185, 184, 181; 128/753

[56] References Cited

U.S. PATENT DOCUMENTS

| 4,211,214 | 7/1980 | Chikashige . |
| 4,222,380 | 9/1980 | Terayama . |
| 4,857,057 | 8/1989 | Sanagi . |
| 5,348,545 | 9/1994 | Shani et al. . |
| 5,601,588 | 2/1997 | Tonomura et al. . |

FOREIGN PATENT DOCUMENTS

| 0704189 | 4/1996 | European Pat. Off. . |
| 6019682 | 6/1985 | Japan . |
| 2-16763 | 5/1990 | Japan . |
| 3-15081 | 4/1991 | Japan . |
| 3-32327 | 7/1991 | Japan . |
| 7-51371 | 2/1995 | Japan . |

OTHER PUBLICATIONS

Copy of a European Search Report dated Apr. 6, 1998 for the corresponding European Application.
"Gastrointestinal Endoscopy", Martin B. Grossman, M.D., *Clinical Symposia,* vol. 32, No. 3, CIBA Pharmaceutical Company, Summit, New Jersey, 1980.

*Primary Examiner*—John D. Yasko
*Assistant Examiner*—Deborah Blyveis
*Attorney, Agent, or Firm*—Greenblum & Bernstein, P.L.C.

[57] ABSTRACT

An injector instrument and a forceps tap for use with an endoscope. The injector instrument is provided with at least one needle formed of a synthetic resin and is further provided with a variety of stopper devices which limit the amount that the needle can extend from the endoscope. The injector instrument may be formed having a curved or easy-to-bend portion. The forceps tap is provided at the entrance to a forceps channel of the endoscope to accommodate at lease two injector instruments or other treatment accessories such that the treatment accessories can be inserted in a single forceps channel and such that substances (such as internal fluids from a human cavity) are held inside the forceps channel.

21 Claims, 53 Drawing Sheets

| EXPERIMENT | R₁ | R₂ | RESULT |
|---|---|---|---|
| ① | 11.9 | 12.2 | OK |
| ② | 10 | 10.3 | OK |
| ③ | 9 | 9.3 | OK |
| ④ | 7.6 | 7.9 | OK |

| EXPERIMENT | R₁ | R₂ | RESULT |
|---|---|---|---|
| ① | 7.6 | 7.85 | OK |
| ② | 7 | 7.25 | OK |
| ③ | 5 | 5.25 | OK |

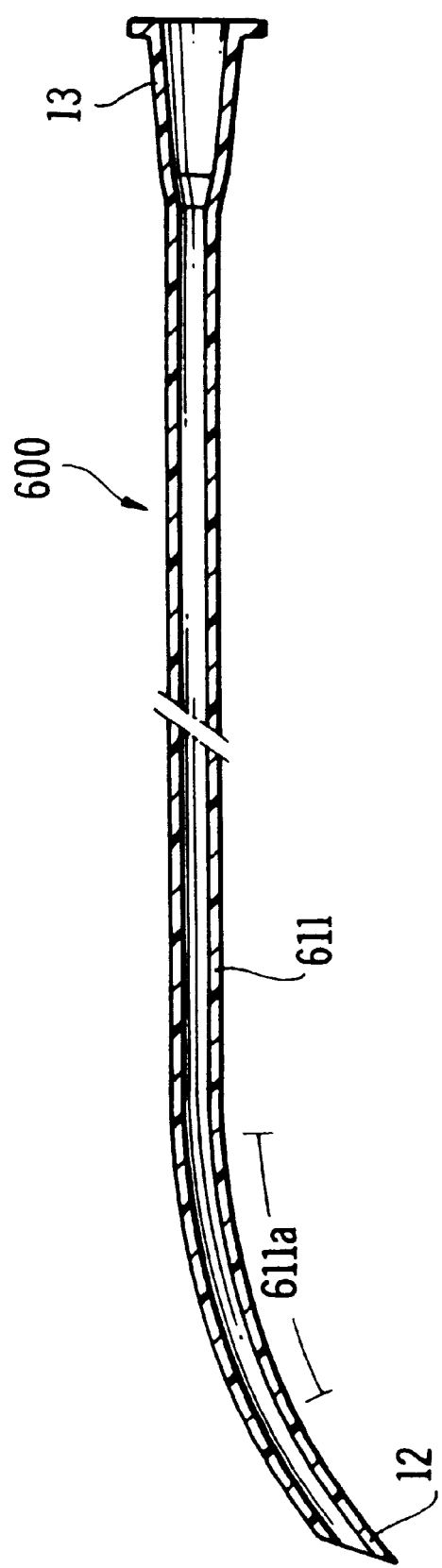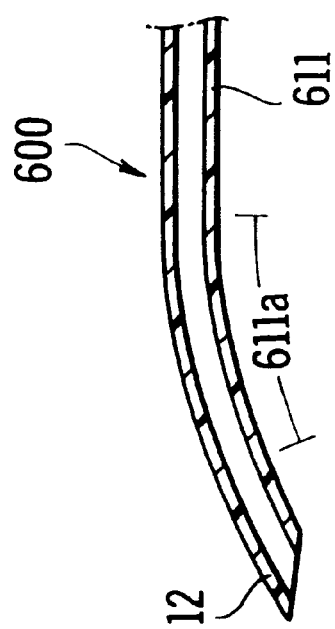

FIG. 42
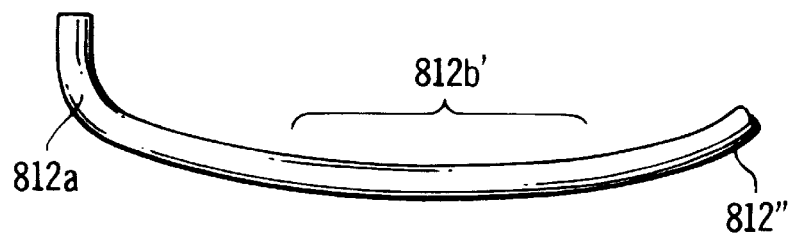
FIG. 43
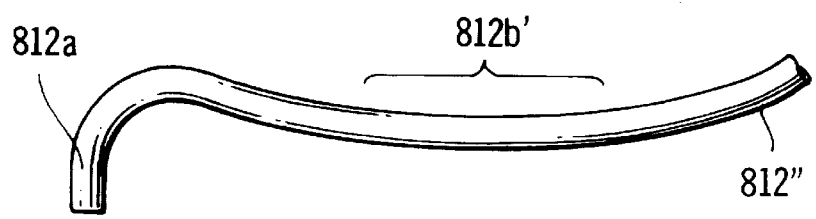
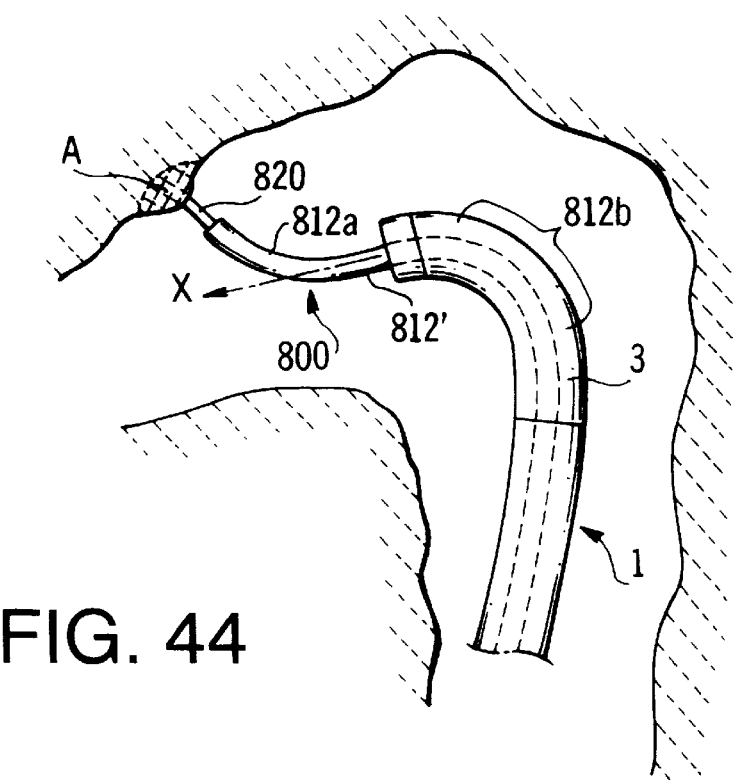
FIG. 44

FIG. 88
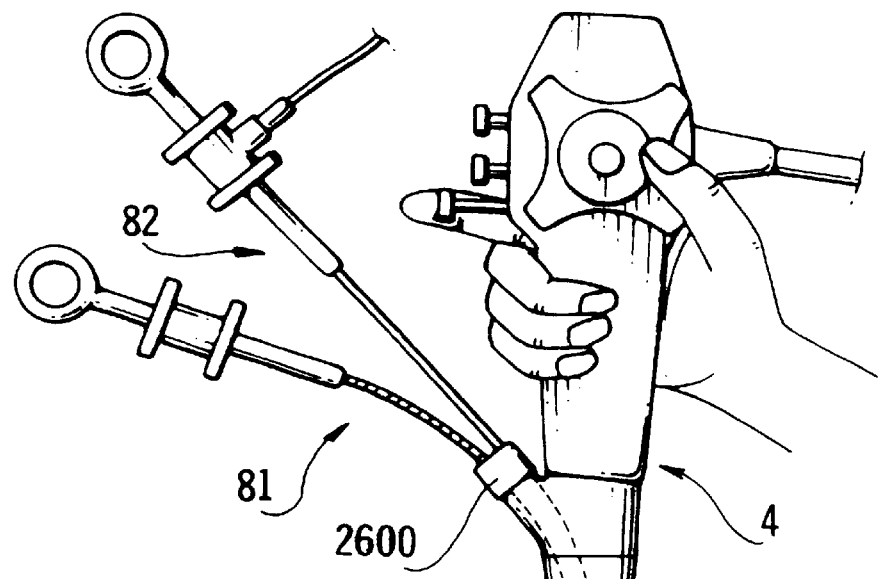
FIG. 87
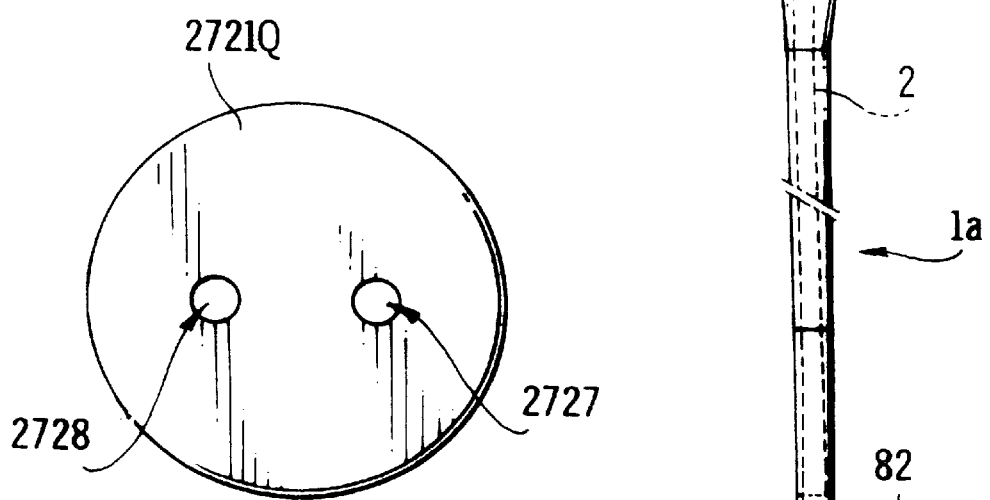
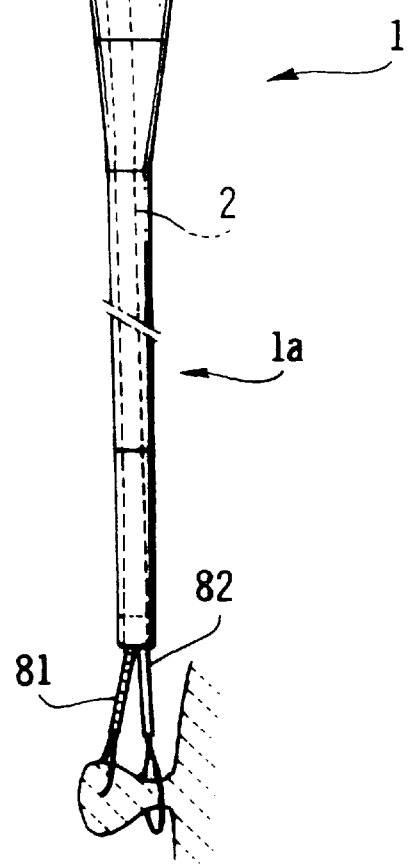

TREATMENT ACCESSORY FOR AN ENDOSCOPE

BACKGROUND OF THE INVENTION

The invention relates to a treatment accessory for an endoscope and, in particular, to an injector instrument, which is used for injecting a medical fluid into tissue within a body cavity.

A conventional injector instrument generally includes a needle, formed as a metal pipe, that is stuck into an inner wall of the body cavity in order to inject the medical fluid.

Generally, the needle is inflexible and must be made as short as possible in order to pass through a forceps channel even when the forceps channel is bent. However, no matter how small, the length of the needle may prevent the passage of the needle through a bent section of the forceps channel.

In order to deliver fluid to the needle, the injector instrument includes a fluid supply tube that is connected to the needle. The fluid supply tube is formed with a flexible material.

Further, since the forceps channel is generally formed of a fluorocarbon resin material, if the metal needle sticks into the wall of the forceps channel, a hole may be made causing difficulties in the operation or use of the endoscope. Therefore, the needle and the fluid supply tube are slidably enclosed in a protective sheath such that the needle can be extended from or retracted into the flexible tube.

Since a double tube structure is used, that is, a fluid supply tube and a protective sheath, either the diameter of the fluid supply tube is too small causing increased resistance in supplying fluid to the needle or the diameter of the outer tube is too large for use in endoscopes having a small-diameter forceps channel. Still further, the use of the double tube structure makes ravage and disinfection difficult. This last problem may be overcome by disposing of the injection instrument after each use (i.e., used as a disposable item), however, the cost of each instrument may be prohibitive.

However, if the conventional injector instrument includes a cover tube made of a synthetic resin, and by sliding the fluid supply tube relative to the cover tube, the injector needle is extended from or retracted into the cover tube other problems may arise.

When the injector instrument is inserted through a forceps channel of an endoscope, the injector needle is retracted inside the cover tube so that the needle does not stick in the side wall of the forceps channel. After the distal end of the injector instrument is extended from the distal end of the forceps channel, the fluid supply tube and the injector needle are pressed from a proximal end such that the injector needle extends from the cover tube.

However, if, during feeding of the injector needle and fluid supply tube through the cover tube or during feeding of the cover tube through the forceps channel, the injector needle is pushed from the proximal end at a time when the injector needle is located at a portion of the cover tube that is curved, the tip of the injector needle may stick into the wall of the cover tube, particularly when the injector needle is oriented such that the tip thereof is located at the outer curvature side of the cover tube.

To avoid such a problem, in a conventional injector instrument, the fluid supply tube may be inserted into the cover tube in an orientation such that a bending tendency of the cover tube and a bending tendency of the fluid supply tube coincide with each other and such that the tip of the injector needle will be located on the inner curvature side of the bent portion when the cover tube bends.

However, such a method is time consuming and difficult to perform and, further, if the orientation of the cover tube or the fluid supply tube changes, the tip of the injector needle may become located on an outer curvature side of the cover tube such that the injector needle may stick in the cover tube.

Further, even if the needle is retracted inside the cover tube, as shown in FIG. 48, when the needle 10020 passes through a curved portion 20003 of the forceps channel 20002 of an endoscope 20000, the needle 10020, having a length A, may pierce through or extend from the cover tube 10012 and also pierce the wall of the forceps channel 20002, and may damage another element, such as an optical fiber 20004 or the like, that is also enclosed in the curved portion 20003 of the endoscope 20000.

Additionally, when making an injection into an affected part, particularly if the affected part is on a slippery mucous surface, it is preferable to insert the needle of the injector instrument in the affected part at a right angle.

A known injector instrument is provided with a wire connected to the distal end of the cover tube and, by operation of the wire, the orientation of the needle is controlled.

However, the distal end portion of the injector instrument is very thin and is easily broken. In this case, since the end portion is bent a short distance by a thin wire, a relatively strong force is required, and the end portion is easily broken. Further, at a manipulation portion of the endoscope, the bending operation and a subtle injecting operation must be done simultaneously, a complicated and difficult procedure.

When the conventional injector instrument for the endoscope is used, an operator inserts the injector instrument into a forceps channel of the endoscope. During this stage, the needle is retracted inside the cover tube. When the injector instrument is inserted, the operator grasps a manipulation portion of the endoscope with one hand, and inserts the cover tube with the other hand.

When the tip of the injector instrument extends from the tip of the endoscope and enters the observing field of the endoscope, the needle is extended from the cover tube. In order to extend the needle, the fluid supply tube is further inserted into the cover tube at the manipulation side. It is difficult for the operator to push the fluid supply tube into the cover tube while also manipulating the endoscope, and thus an assistant pushes the inner tube according to the operator's instruction.

When the needle has been extended from the tip of the cover tube, the needle is stuck in the affected part of the human tissue. This is done by pushing the cover tube into the forceps channel of the endoscope.

When the needle is stuck into the affected part, medical fluid is supplied to the inner tube from the manipulation side. The medical fluid is supplied from an injector connected to the proximal end of the fluid supply tube, and operated by the assistant.

After the medical fluid is injected, the cover tube is pulled to remove the needle from the affected part. The needle is then retracted inside the cover tube by pulling the fluid supply tube, and lastly the cover tube is drawn out of the forceps channel of the endoscope to completely remove the injector instrument.

In each of the above steps of using the injector instrument, co-operation between the operator and the assistant is required.

An injection treatment requires a subtle manipulation of each part of the injection instrument and of the endoscope.

However, if the operation of extending the needle from the cover tube, and the insertion of the needle in the affected part is divided and assigned to two different individuals, i.e., the operator and the assistant, the injection treatment is considerably difficult to perform accurately and requires both the operator and assistant to be skilled in the manipulation of the injector instrument and the endoscope.

As discussed above, it is important to control the length that the injector instrument extends beyond the distal end of the endoscope and the orientation of the injector instrument relative to the distal end of the endoscope. This is also important for other conventional treatment accessories which are generally provided with a flexible tube through which an operation wire is inserted. The flexible tube of the treatment accessory is inserted in the forceps channel of the endoscope.

When a treatment is performed, the flexible tube is positioned to face an affected part to be treated by sliding the flexible tube inside the forceps channel, and once the flexible tube is located in position, the flexible tube is held by hand, and the operation wire is operated to perform the intended treatment.

Similar to the operation of the injector instrument described above, when the endoscopic treatment is performed the operations of manipulation of the flexible tube, holding of the flexible tube, and manipulation of the operation wire must all be done.

It is difficult for an operator to perform all of the above operations alone, and generally, an assistant assists the operator to perform the endoscopic treatment. Since all of the operations cannot be done by a single operator, the treatment is complicated and may not be carried out with accuracy.

In a particular case, the injector instrument described above may be used for homeostasis treatment inside a digestive tube, such as an esophageal tube. In homeostasis treatment, it is sometimes necessary to inject homeostatic fluid in a plurality of adjacent positions within the digestive tube and further, the injection must occur relatively accurately on an affected area. As such, due to a need for multiple injections or due to an initial misplacement of the needle, the needle will be stuck into the tissue more than once, that is, the needle is stuck in, and if properly located an injection is performed, then the needle is removed and moved to another position. The needle is then stuck in at the new position, and so forth. However, when the needle is removed after being stuck in the first time, bleeding occurs and the area becomes clouded by the blood. Therefore, it becomes difficult to observe the area around the affected part through the endoscope and accurately select the next injection location. Thus, the blood must be washed out with cleaning fluid before the next injection is done.

In the endoscope, in order to prevent the sores (internal fluids and the like) inside the human cavity from coming back through the forceps channel and exiting through the entrance thereof, a forceps tap is provided at the entrance (the proximal side) of the forceps channel. Conventionally, the forceps tap is provided with a slit and when the treatment accessory is used, the slit is pushed-open by the treatment accessory and the treatment accessory is inserted through the forceps channel.

The slits on conventional forceps taps are designed to allow only one treatment accessory to be inserted through. Therefore, if a plurality of treatment accessories are to be used, a specialized endoscope having a plurality of forceps channels must be used, and the treatment accessories are then inserted through respective forceps channels.

Since a plurality of channels are formed, the insertion portion of such an endoscope is relatively thick, which increases the amount of pain felt by a patient. Further, as the number of forceps channels and taps provided is increased the cost of the endoscope increases.

Japan Utility Model Registration Publication SHO 60-19682 describes an endoscope having a manipulation portion and an insertion portion. The insertion portion is provided with a single forceps channel, however, in the manipulation portion, the forceps channel is branched such that at the proximal side end, two channels are formed.

Such a structure requires the inclusion of a branching channel arrangement in the manipulation portion. This further complicates the structure of the already complicated manipulation portion and increases the size of the manipulation portion. Further, two forceps taps are still necessary to cover the two channels.

SUMMARY OF THE INVENTION

It is therefore an object of the present invention to provide an improved injector instrument which is inexpensive, is easily fed around bends in a forceps channel, is sufficiently small to be inserted into even a thin forceps channel, and is easily cleaned and disinfected.

Another object of the invention is to provide an improved injector instrument in which the needle does not stick in the cover tube allowing easy assembly.

Yet another object of the invention is to provide an improved injector instrument allowing the needle to be appropriately oriented with respect to an affected portion.

A further object is to provide an injector instrument that is durable and is relatively inexpensive to manufacture.

A still further object of the invention is to provide an improved injector instrument which does not have a rigid needle portion which may damage another member adjacent to the forceps channel.

Still yet another object of the invention is to provide an improved injector instrument with which the operator can insert a needle at a target position easily and accurately.

Yet another object of the invention is to provide an improved endoscope system which enables an operator to perform the endoscopic treatment alone.

Still yet another object of the invention is to provide an improved injector instrument that facilitates performing multiple insertions of the needle and therefore facilitates performing multiple injections.

Still another object of the invention is to provide an improved forceps tap having a simple and inexpensive design which allows a plurality of treatment accessories to be introduced into a single forceps channel.

According to one aspect of the invention, there is provided an injector instrument, for insertion into a forceps channel of an endoscope, that includes a flexible fluid supply tube and a needle portion provided at a distal end of the fluid supply tube. In particular, the needle portion is formed from a material having a Rockwell hardness from R50 to R129. Further, the needle portion could be formed from a material having a Shore hardness of D75 or less. Note that the forceps channel is made of a material having a Shore hardness from D41 to D70.

With this arrangement of the injector instrument, the injector instrument can be easily inserted in the forceps channel with less risk of the needle portion sticking in the walls of the forceps channel.

In a preferred embodiment, the fluid supply tube and needle portion may be integrally formed.

In another preferred embodiment, the needle portion may include an obliquely cut sharp tip.

In yet another preferred embodiment, the needle portion may include a sharp tip having two slanted planes.

In yet another preferred embodiment, the injector instrument may further include a mandrel member that is inserted into the fluid supply tube and the needle portion during insertion of the fluid supply tube and the needle portion into the forceps channel.

In yet another preferred embodiment, the hardness of the needle portion may be greater than the hardness of a wall of the forceps channel.

In yet another preferred embodiment, the needle portion my include a stop element spaced from a distal end of the needle portion.

In yet another preferred embodiment, the needle portion may be a flexible resin.

In yet another preferred embodiment, the injector instrument may further include a cover tube, the fluid supply tube and needle portion being inserted into the cover tube.

In this embodiment, the fluid supply tube and the needle portion can also be easily inserted into the cover tube without the needle portion sticking in the walls of the cover tube.

In a particular case of this embodiment, the injector instrument may further include a detent element that holds the needle portion in at least one position with respect to the cover tube. The detent element may include an O-ring on one of the fluid supply tube and cover tube and at least one groove on the other of the fluid supply tube and cover tube. Preferably, there are two grooves spaced a predetermined distance apart and the needle portion has a movable distance within the cover tube which is less than the predetermined distance.

In another particular case of this embodiment, at least two fluid supply tubes and needle portions are inserted into the cover tube.

In yet another particular case of this embodiment, the cover tube is a coiled wire. In this case, the injector instrument may further include a metal tip portion at the distal end of the coiled wire.

In yet another particular case of this embodiment, the injector instrument may further include a manipulation element, the manipulation element moving the fluid supply tube within the cover tube.

In yet another particular case of this embodiment, the injector instrument may further include a mandrel member that is inserted into the fluid supply tube and the needle portion during insertion of the fluid supply tube and the needle portion into the cover tube.

In yet another preferred embodiment, the fluid supply tube may be formed to have a curved portion at a distal end portion when the fluid supply tube is in a neutral state.

According to another aspect of the invention, there is provided an injector instrument, for insertion into a forceps channel of an endoscope, that includes a flexible fluid supply tube, a needle portion provided at a distal end of the fluid supply tube, and a cover tube in which the fluid supply tube is slidably inserted. The cover tube is formed to have a first curved portion at a distal end portion when the cover tube is in a neutral state.

In a preferred embodiment, the cover tube includes a second curved portion. In a particular case, the second curved portion has a greater radius of curvature than the first curved portion. Further, the first and second curved portions are curved in the same direction or in opposite directions.

In another particular case, the second curved portion is neutrally straight but bends more easily than the first curved portion.

According to yet another aspect of the invention, there is provided a treatment accessory, for insertion into an entrance of a forceps channel of an endoscope, that includes a flexible element, a treatment device attached at a distal end of the flexible element, and a fixing tube attached to a predetermined portion along the length of the flexible element. The fixing tube is also positioned to abut the entrance of the forceps channel.

In a preferred embodiment, the fixing tube is inserted into an opening at the entrance of the forceps channel.

In another preferred embodiment, the fixing tube is adjustable along the length of the flexible element.

In a particular case of this embodiment, the treatment accessory may further include a locking device for locking the fixing tube at a selected position along the length of the flexible element. In particular, the locking device may include two complementary tapered elements. Alternatively, the locking device may include a slot in the fixing tube, and a roller guided in the slot to press against the flexible element.

According to yet another aspect of the invention, there is provided a forceps tap, for closing an end of a forceps channel of an endoscope, that includes at least two treatment accessory guide portions provided at an upper surface of the forceps tap, adjacent guide portions being separated by a portion of the forceps tap, and an opening for receiving a treatment accessory located beneath each of the at least two guide portions.

In a preferred embodiment, each opening is formed as a single slit forms each of the openings.

In another preferred embodiment, each of the openings is a slit.

In yet another preferred embodiment, one of the openings is a slit and another of the openings is a hole.

In yet another preferred embodiment, the forceps tap includes a separate packing containing the openings, the separate packing being located beneath the guide portions.

BRIEF DESCRIPTION OF THE DRAWINGS

FIG. 25 is a sectional side view of an injector instrument according to a seventh embodiment of the invention;

FIG. 26 is a sectional side view of an alternative arrangement of the injector instrument of FIG. 25;

FIG. 42 is a side view of another modified cover tube of the injector instrument of FIG. 33;

FIG. 43 is a side view of an alternative structure for the modified cover tube of FIG. 42;

FIG. 44 is a schematic view illustrating the use of the injector instrument of FIG. 33 having the modified cover tube of FIG. 41 in the endoscope in a large intestine.

FIG. 87 is a top view of a modification of the packing of FIG. 83; and

FIG. 88 is a schematic view illustrating the use of endoscope provided with the forceps tap of FIG. 78.

DETAILED DESCRIPTION OF THE PREFERRED EMBODIMENTS

Figure 1:
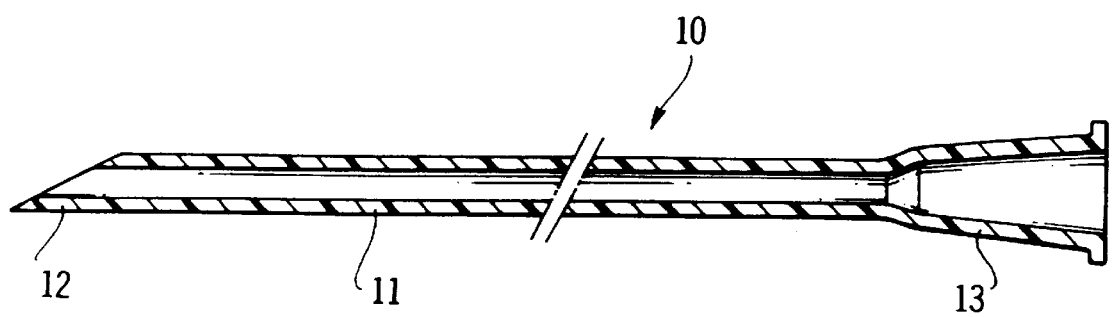
FIG. 1 is a sectional side view of an injector instrument according to a first embodiment of the invention.
Figure 3:
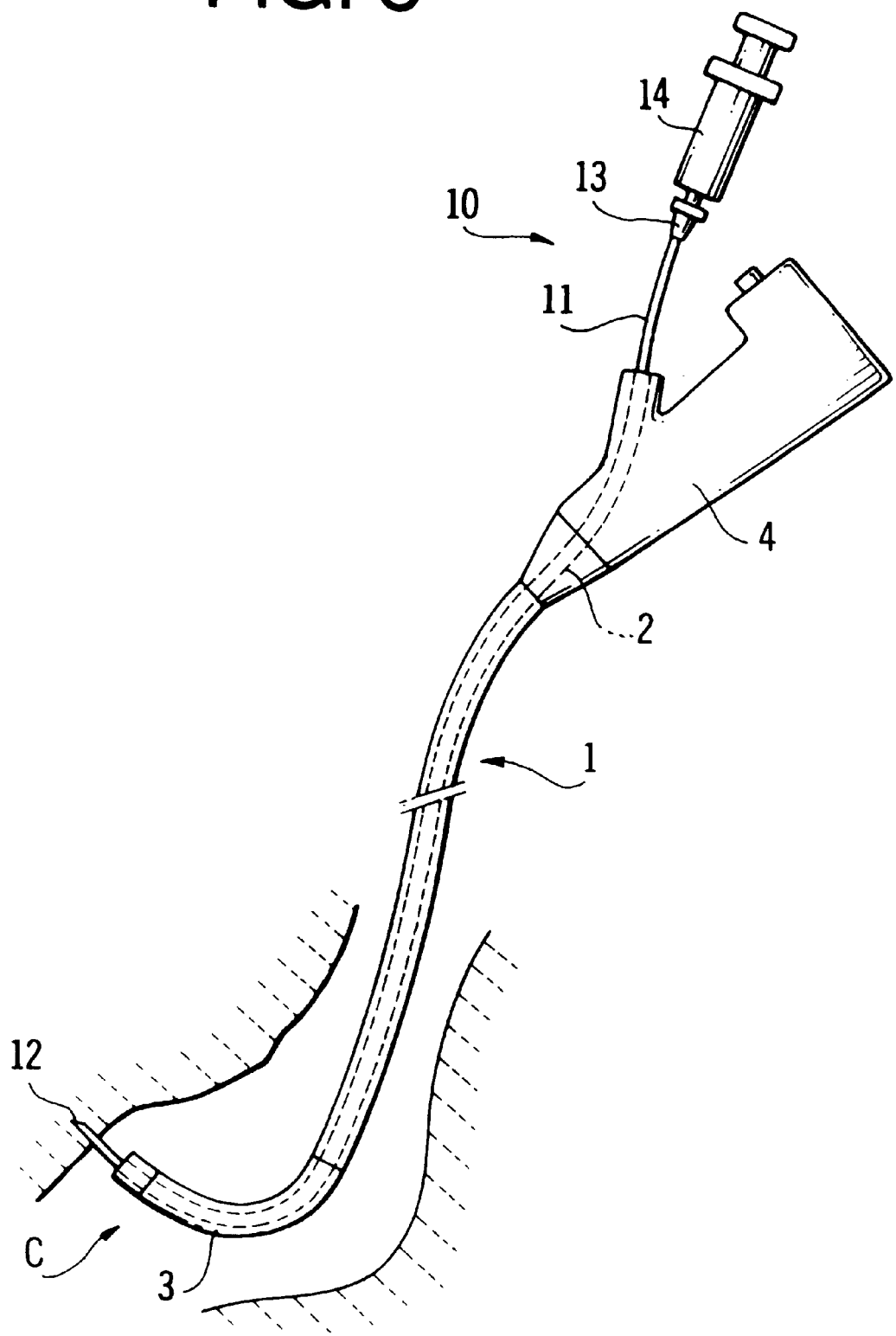
FIG. 3 is a side view of an endoscope having a forceps channel in which the injector instrument of FIG. 1 is inserted.

FIG. 1 shows a sectional side view of an injector instrument 10 according to a first embodiment of the invention. As shown in FIG. 3, in use, the injector instrument 10 is detachably connected to an injector 14 and is removably inserted through a forceps channel 2 of an endoscope 1 into a body cavity C.

The injector instrument 10 is made of a synthetic resin having a predetermined flexibility and a predetermined elasticity. Specifically, the injector instrument 10 may be made of polyimide resin, ETFE (ethylene-tetra-fluoroethylene copolymer) resin, or the like. It is noted that the synthetic resin used need only meet a certain condition regarding hardness described below and that alternatives may be available.

Figure 2:
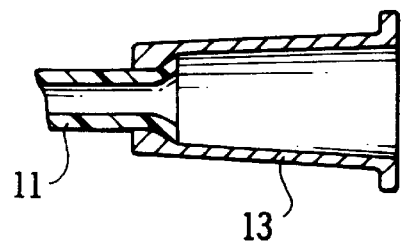
FIG. 2 is a sectional side view showing an alternative arrangement of the injector instrument according to the first embodiment of the invention.

The injector instrument 10 is integrally formed to include a fluid supply tube 11, a needle portion 12, formed for example, by cutting a distal end portion of the fluid supply tube 11 obliquely to form a sharp tip, and an infusion portion 13, formed at a proximal end portion of the fluid supply tube 11. It is noted that the infusion portion 13 may alternatively be formed separately from the fluid supply tube 11 and connected to the proximal end of the fluid supply tube 11 as shown in FIG. 2. Further, as described below with respect to FIG. 19 the needle portion 12 may also be formed separately form the fluid supply tube 11.

As described briefly above, in use, the injector instrument 10 is inserted through the forceps channel 2 of the endoscope 1 and the injector 14 is attached to the fluid supply portion 13. As shown in FIG. 3, the needle portion 12 is extended from the tip of an insertion portion of the endoscope 1, and stuck in the wall of the body cavity C. Then, fluid from the injector 14 is pushed into the fluid supply portion 13 and supplied through the fluid tube 11 to be injected into the wall of the body cavity C at the needle portion 12.

In this embodiment, the injector instrument 10 does not have a cover tube, such that even if the forceps channel has a relatively small diameter, the diameter of the fluid tube 11 can still be made sufficiently large that sufficient medical fluid can be injected easily.

As shown in FIG. 3, the endoscope 1 includes a bendable portion 3 which is bent in accordance with an operation of a manipulation portion 4. of course, when the bendable portion 3 is bent, the forceps channel 2 inside the bendable portion 3 is also bent, and, depending on the treatment being performed may have a very small radius of curvature.

Figure 4:
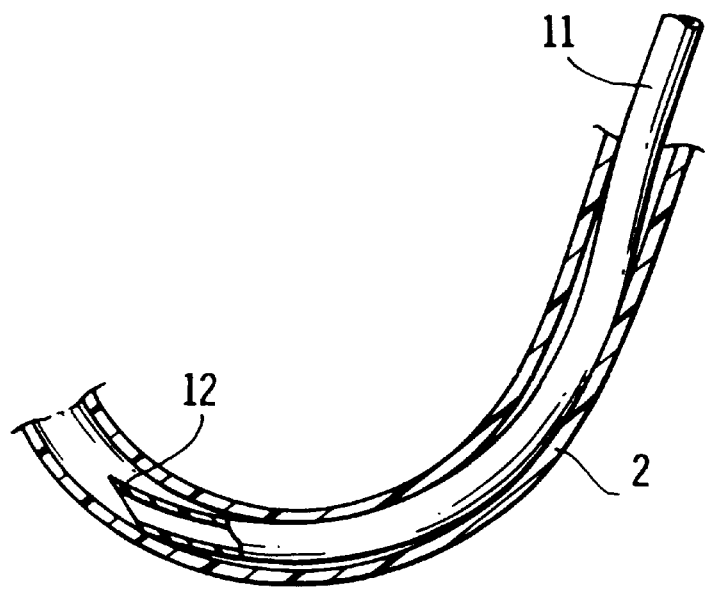
FIG. 4 is a schematic sectional view illustrating the feeding of the injector instrument of FIG. 1 through the forceps channel.

FIG. 4 shows the needle portion 12 passing through the bent forceps channel 2 that is inside the bendable portion 3. In this case, a sharp tip of the needle portion 12 is located on the inner side of the curvature, such that there is little chance that the sharp tip will stick in the forceps channel 2. Further, since both the fluid supply tube 11 and the needle portion 12 are formed of a flexible material, the needle portion 12 and the fluid supply tube change shape in accordance with the shape of the forceps channel 2, and pass through the forceps channel 2 easily. As shown in FIG. 3, the needle portion 12 and the portions of the fluid supply tube 11 that extend from the distal end of the forceps channel 2 elastically return to a straight shape and can therefore be stuck in the wall of the body cavity C.

Figure 5:
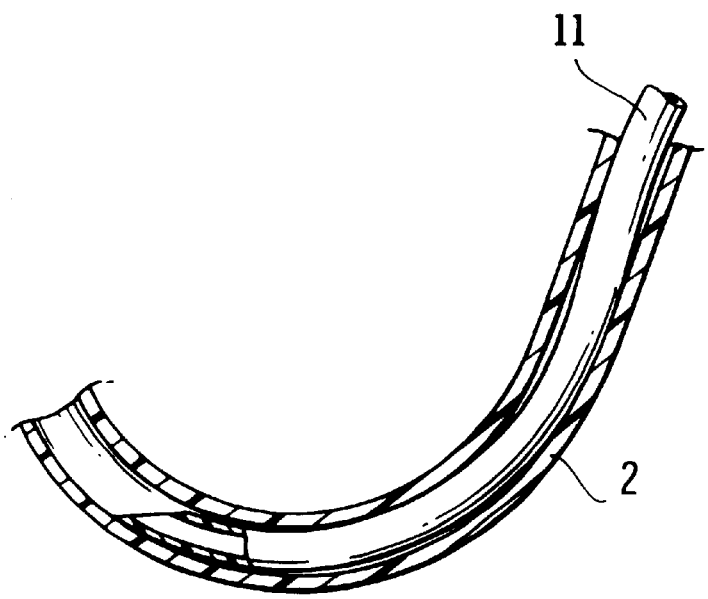
FIG. 5 is a schematic sectional view illustrating the feeding of the injector instrument of FIG. 1 through the forceps channel when in a different state.

FIG. 5 shows another configuration of the needle portion 12 passing through the bent forceps channel 2, in this case, the sharp tip of the needle portion 12 is located on the outer side of the curvature and the sharp tip may stick in and damage the inner wall of the forceps channel 2. However, the design of the injector instrument 10, as described below, is such that this problem will not occur.

Generally, the inner wall of the forceps channel is made of low density polyethylene (Shore hardness: D41–50), high density polyethylene (Shore hardness: D60–70), perfluoro alkoxy resin (PFA) (Shore hardness: D60–64), polytetra-fluoroethylene (PTFE) (Shore hardness: D50–56), or the like. In other words, the forceps channel (which is generally a tubular member) is made of a material having a hardness within a range of Shore hardnesses of D41–D70).

In the past it has been assumed that, only if the needle portion 12 is made of a material having a hardness that is less than the hardness of the wall of the forceps channel 2, the needle portion 12 will not stick in the wall of the forceps channel 2.

However, experiments described in detail below have shown that it is not necessary that the hardness of the needle portion 12 be less than the hardness of the wall of the forceps channel 2. The experiments show that even if the needle portion 12 is made of ethylene-tetra-fluoroethylene (ETFE) having Shore hardness D75, or polyimide having Rockwell hardness R129, both of which are apparently harder than the wall of the forceps channel 2, the needle portion 12 can be fed without sticking in the wall of the forceps channel 2.

Figures 6, 7, 8:
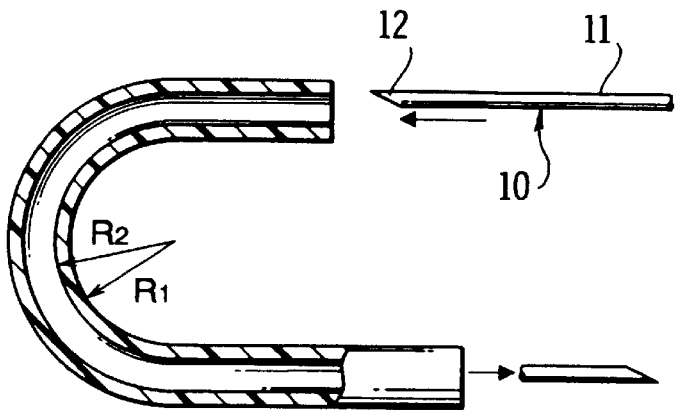
FIG. 6 is a schematic sectional view illustrating the conditions for an experiment regarding feeding of the injector instrument of FIG. 1 through the forceps channel.
FIG. 7 is a table showing the results of the experiment conducted according to FIG. 6.
FIG. 8 is a table showing the results of the experiment conducted according to FIG. 6 using different parameters.

FIG. 6 shows the condition of the experiments. In the experiment, the wall of the forceps channel 2 was made of perfluoro alkoxy resin (PFA) having Shore hardness of D60–64. The bendable portion 3 of the endoscope 1 was bent at a curvature radius R1 (outer wall) or R2 (inner wall). The needle portion 12 was made of polyimide (Rockwell hardness: R129). In all of the experiments, the needle point 12 was located on the outer side of the curvature.

FIG. 7 shows a table indicating the results for four different curvature radiuses when the inner/outer diameters of the forceps channel 2 were 2.2 mm/2.8 mm, and the inner/outer diameters of the needle portion 12 were 0.7 mm/1.25 mm. As indicated in the table, for each of the four different curvature radiuses, the needle portion 12 was fed without sticking in the wall of the forceps channel 2. Similar experiments conducted with standard metal needles resulted in the metal needles sticking in the wall of the forceps channel 2.

FIG. 8 shows another table when the inner/outer diameters of the channel 2 are 1.2 mm/1.7 mm, and the inner/outer diameters of the needle portion 12 are 0.7 mm/1.00 mm. As indicated in the table, for each of three different curvature radiuses, the needle portion 12 was fed without sticking in the wall of the forceps channel 2. Similar experiments were conducted with standard metal needles. It should be noted that the conventional injector instrument having a metal needle should be provided with a sheath. Accordingly, the experiments were conducted with an injector instrument which has a sheath (whose outer diameter is 1.75 mm) to which a metal needle is connected. The length of metal needle is 8 mm, the outer diameter of the needle is approximately 0.63 mm. Such experiments resulted in the metal needles sticking in the wall of the forceps channel 2.

As described above, even if the needle portion 12 has a hardness that is greater than that of the wall of the forceps channel 2, the needle portion 12 can proceed through the forceps channel 2 without sticking in the wall of the forceps channel 2. Although conclusive studies have not been performed, it appears that the reason that a metal needle will stick in a wall of a forceps channel but the needle portion 12 does not stick in the wall of the forceps channel 2 is due to differences between the hardnesses of the wall of the forceps channel and the needle, sliding friction and the like.

Figure 9:
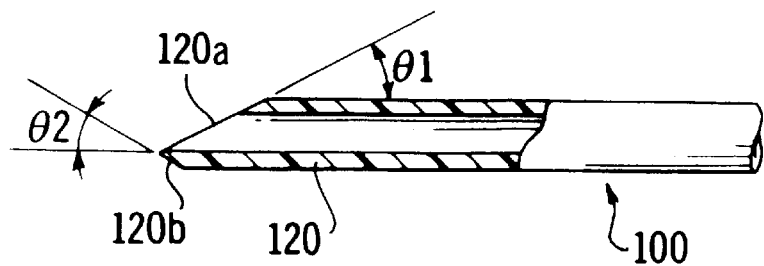
FIG. 9 is a sectional view of a distal end of an injector instrument according to a second embodiment of the invention.

FIG. 9 shows an injector instrument 100 according to a second embodiment wherein the tip of a needle portion 120 is formed having two slanted planes 120a and 120b. In this embodiment, the angles of the planes 120a and 120b with respect to the axis of the needle portion 120 is 30 degrees, such that the acute angle between the planes 120a and 120b is 60 degrees. However, it is noted that the angles need not be limited to 30 degrees.

Figure 10:
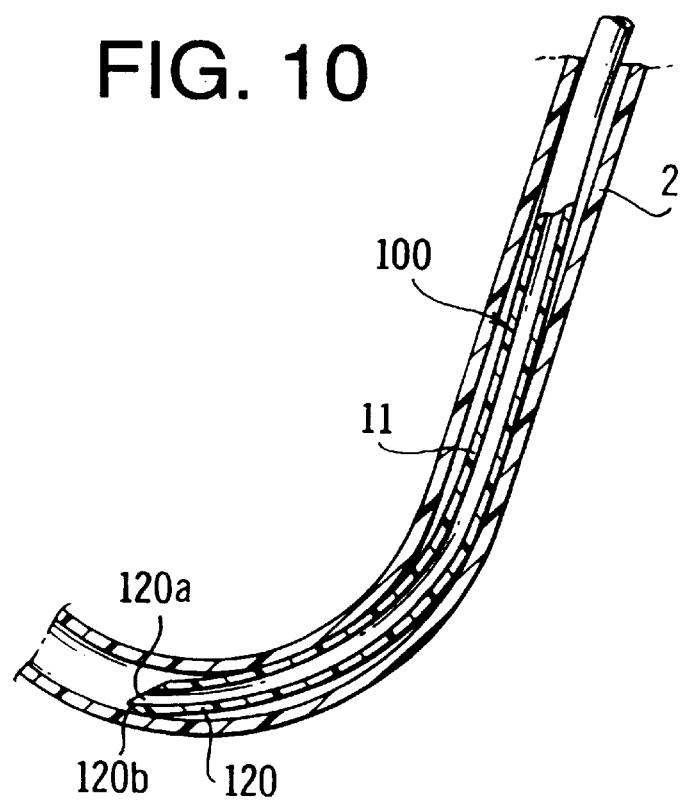
FIG. 10 is a schematic view illustrating the insertion of the injector instrument of FIG. 9 in the forceps channel.

If the tip of the needle portion 120 is formed having the slanted planes 120a and 120b as described above, when the channel is bent at a relatively small radius, as shown in FIG. 10, the tip of the needle portion 120 does not contact the wall of the channel 2, and the needle portion 120 proceeds without sticking in the wall of the forceps channel 2 even if a relatively hard material is used for the needle portion 120.

Figure 11:
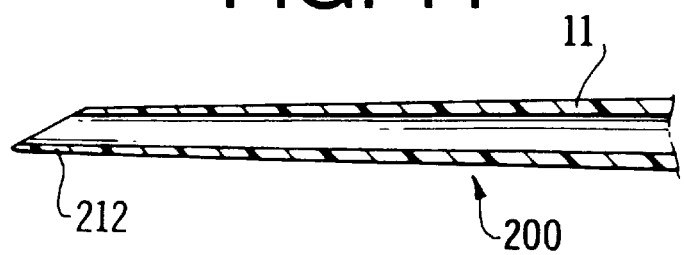
FIG. 11 is a sectional view of a distal end of an injector instrument according to a third embodiment of the invention.

FIG. 11 shows an injector instrument 200 according to a third embodiment in which a needle portion 212 is made thinner at the tip side (left-hand side in FIG. 11). With this structure, the needle portion 212 is more flexible at the tip side thereof and thus bends easier such that the needle portion 212 is less likely to stick in the wall of the forceps channel 2 even if a relatively hard material is used for the needle portion 120.

Figure 12:
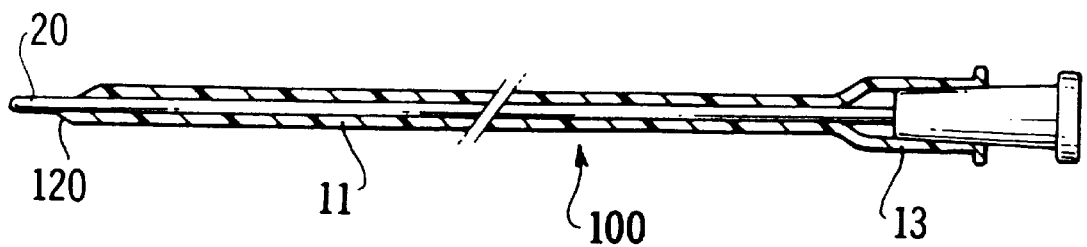
FIG. 12 is a schematic sectional view illustrating the injector instrument of FIG. 1 further provided with a mandrel member.

FIG. 12 shows the injector instrument 100 of the second embodiment being further provided with a mandrel member 20 having a rounded tip that is inserted through the fluid supply tube 11 during insertion of the injector instrument in the forceps channel 2. As shown in FIG. 12, the rounded tip of the mandrel member 20 is extended from the needle portion 12 before the injector instrument 10 is inserted in the forceps channel 2. Since the rounded tip of the mandrel member 20 contacts the wall of the forceps channel 2, even if the needle portion 12 is made of a relatively hard material, the needle portion 12 will not stick in the wall of the forceps channel 2. After installation of the injector instrument 100 is finished, the mandrel member 20 is pulled towards the proximal end of the fluid supply tube 11 and removed therefrom. Of course, the mandrel member 20 may be also be provided for use during insertion of injector instruments according to the other embodiments described herein.

Figure 13:
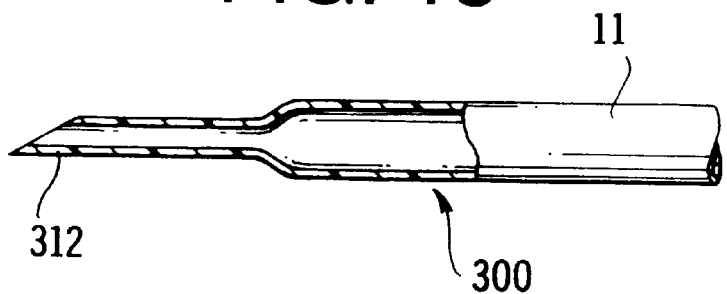
FIG. 13 is a sectional view of a distal end of an injector instrument according to a fourth embodiment of the invention.
Figure 14:
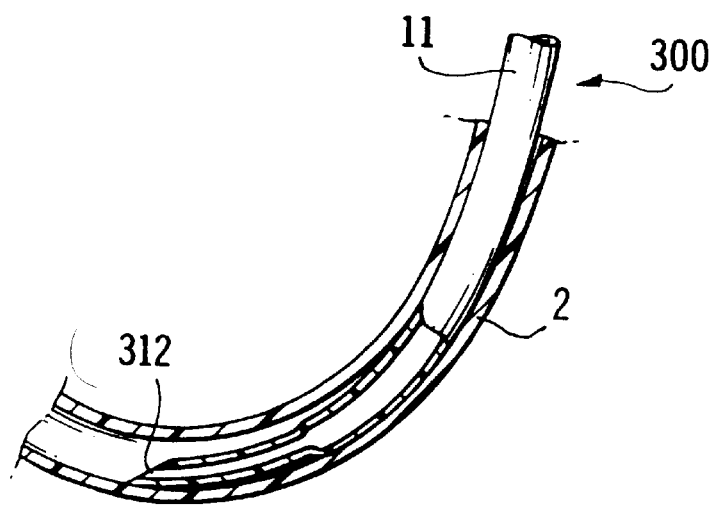
FIG. 14 is a schematic view illustrating the insertion of the injector instrument of FIG. 13 in the forceps channel.

FIG. 13 shows an injector instrument 300 according to a fourth embodiment. In the fourth embodiment, the front end portion (left-hand side portion in FIG. 13) of a needle portion 312 is formed to have a smaller diameter than the other portion of the needle portion 312. With this structure, the smaller diameter portion is more flexible and more easily bends to follow the curvature of the forceps channel 2 as shown in FIG. 14. Further, with this arrangement, the depth to which the needle portion 312 enters the wall of the body cavity C is restricted to the length of the smaller diameter portion, and accordingly the amount that the needle portion 312 sticks into the wall of the body cavity C can be set as desired. In this embodiment, the length and the diameter of the small diameter portion may be designed depending on the particular use or purpose of the injector instrument 300.

Figure 15:
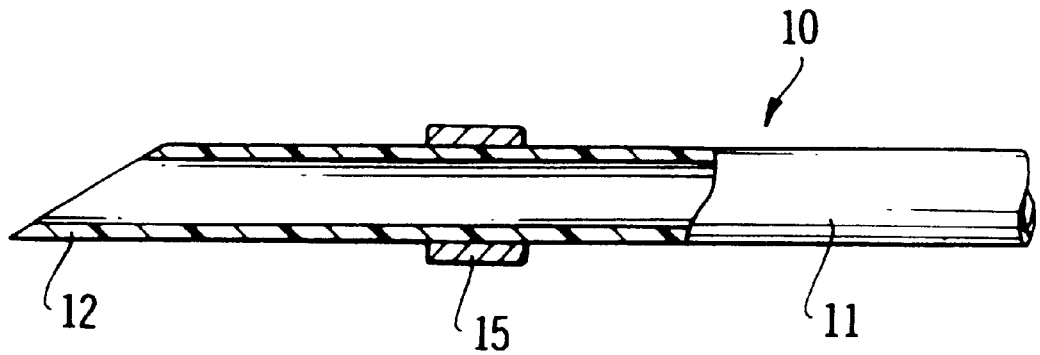
FIG. 15 is a schematic sectional side view of the injector instrument of FIG. 1 further provided with a ring-shaped protrusion.
Figure 16:
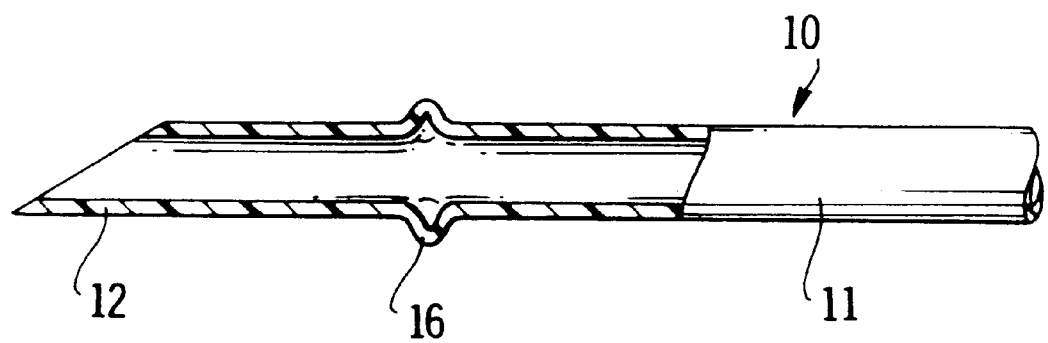
FIG. 16 is a schematic sectional side view of the injector instrument of FIG. 1 further provided with two protruded portions.
Figure 17:
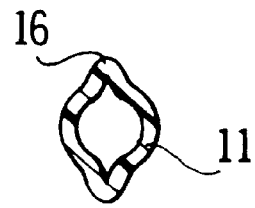
FIG. 17 is a schematic sectional end view of the injector instrument of FIG. 16.
Figure 18:
FIG. 18 is a sectional sectional end view of the injector instrument of FIG. 16 modified to include three protruded portions.

FIG. 15 shows the injector instrument 10 of the first embodiment modified in that the needle portion 12 is provided with a ring-shaped protrusion 15 which is fixed close to the tip of the needle portion 12. The ring-shaped protrusion 15 controls the depth to which the tip of the needle portion 12 enters into the wall of the body cavity C. FIG. 16 shows an alternative wherein the ring-shaped protrusion 15 described above is replaced with at least one protruded portion 16 (in FIG. 16, two protruded portions are shown) which is formed by heat processing of the needle portion 12 and which is appropriately positioned on the needle portion. A cross section of the protruded portions 16 is shown in FIG. 17. Further alternatively, additional protruded portions 16 may also be formed, for example, three protruded portions 16 may be formed as shown in FIG. 18. The modifications described with reference to FIGS. 15 through 18 could also be applied to the injector instruments 100, 200 according to the second and third embodiments.

Figure 19:
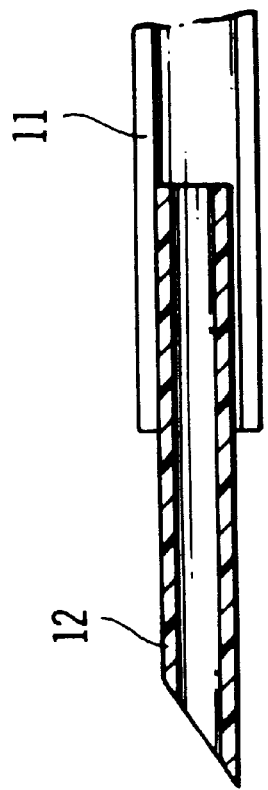
FIG. 19 is a sectional side view showing another alternative arrangement of the injector instrument according to the first embodiment of the invention.

FIG. 19 shows a further alternative structure of the injector instrument 10 according to the first embodiment described above. In this structure, the fluid supply tube 11 and the needle portion 12 are formed separately and attached, for example, by adhesion, such that the fluid supply tube 11 forms a ridge around the needle portion 12 that controls the depth to which the tip of the needle portion 12 enters into the wall of the body cavity C.

According to the above embodiments and alternatives, since the injector instrument is formed using a tube having a predetermined flexibility and elasticity and then cutting an end thereof to form a needle portion, the injector instrument can be fed into the forceps channel easily. Further, since the injector instrument has a single tube structure, even if the forceps channel is thin, the inner diameter of the fluid supply tube can be made sufficiently large to provide a sufficient amount of fluid flow. Further, the injector instrument can be easily washed and disinfected. Furthermore, since the injection device is relatively simple in construction, manufacturing costs can be reduced such that, if necessary, the injector instrument may be disposed of after a single use. Furthermore, the injector instrument may easily be provided with a restricting member which restricts the depth to which the needle portion is stuck in the wall of the body cavity.

Figure 20:
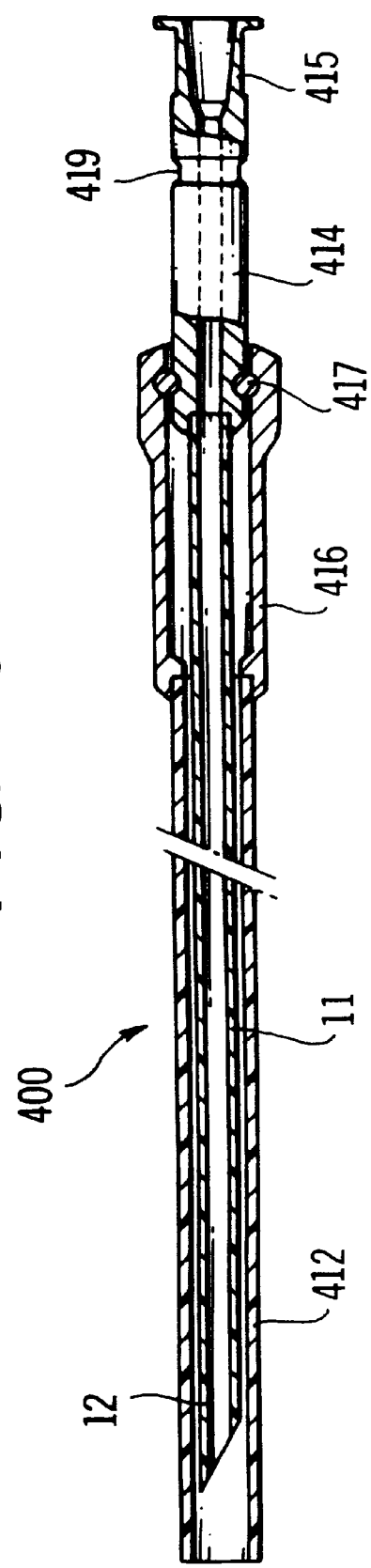
FIG. 20 is a sectional side view of an injector instrument according to a fifth embodiment of the invention.
Figure 22:
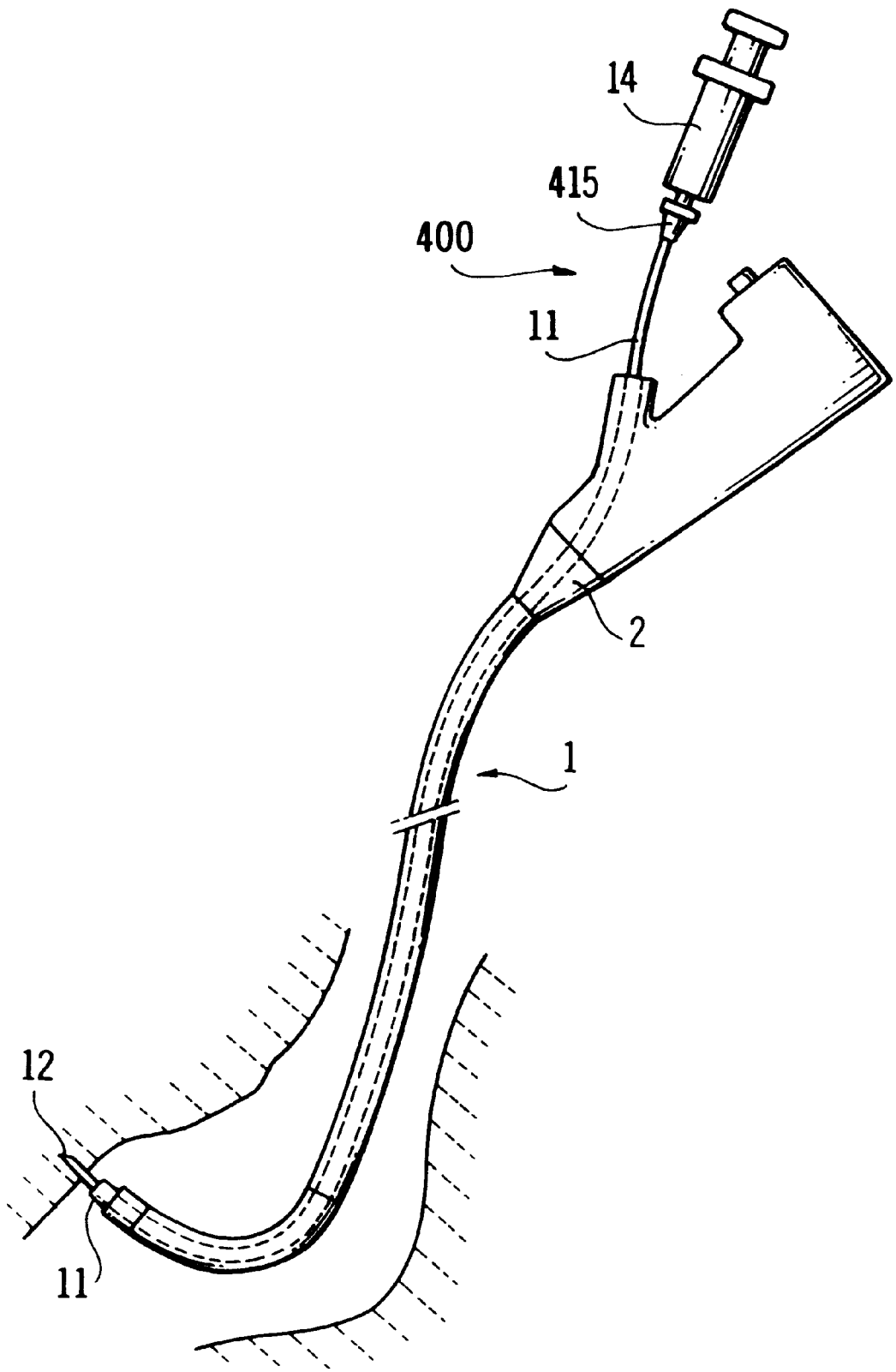
FIG. 22 is a side view of an endoscope having a forceps channel in which the injector instrument of FIG. 20 is inserted.

FIG. 20 shows an injector instrument 400 according to a fifth embodiment. The injector unit 400 is similar to the injector unit 10 of the first embodiment and common elements are provided with the same reference numbers. As shown in FIG. 22, in use, the injector instrument 400 is inserted through the forceps channel 2 of the endoscope 1.

As shown in FIG. 20, the injector instrument 400 includes a flexible cover tube 412 that covers the fluid supply tube 11. Both of the flexible cover tube 412 and the fluid supply tube 11 are made of a synthetic resin having predetermined flexibility and elasticity. As above, the distal end of the fluid supply tube 11 is cut obliquely to form the needle portion 12. Of course, the variations above may also be applied to this embodiment.

The proximal end of the fluid supply tube 11 is connected to an inner tube 414 which is formed with or connected to a mouth piece 415. The proximal end of the cover tube 412 is connected to an outer tube 416. The inner tube 414 is movable along its axis inside the outer tube 416.

An O-ring 417 is provided at the proximal side of the outer tube 416 on an inner surface thereof. The outer surface of the inner tube 414 is provided with, near both end thereof, first and second click grooves 418 and 419. The engagement of the O-ring 417 with either of the first or second click grooves 418 or 419, accurately positions the inner tube 414 relative to the outer tube 416.

In FIG. 20, the O-ring 417 is engaged with the first click groove 418. In this state, the needle portion 12 is retracted inside the cover tube 412. The injector instrument 400 is inserted in or removed from the forceps channel 2 in this state.

Figure 21:
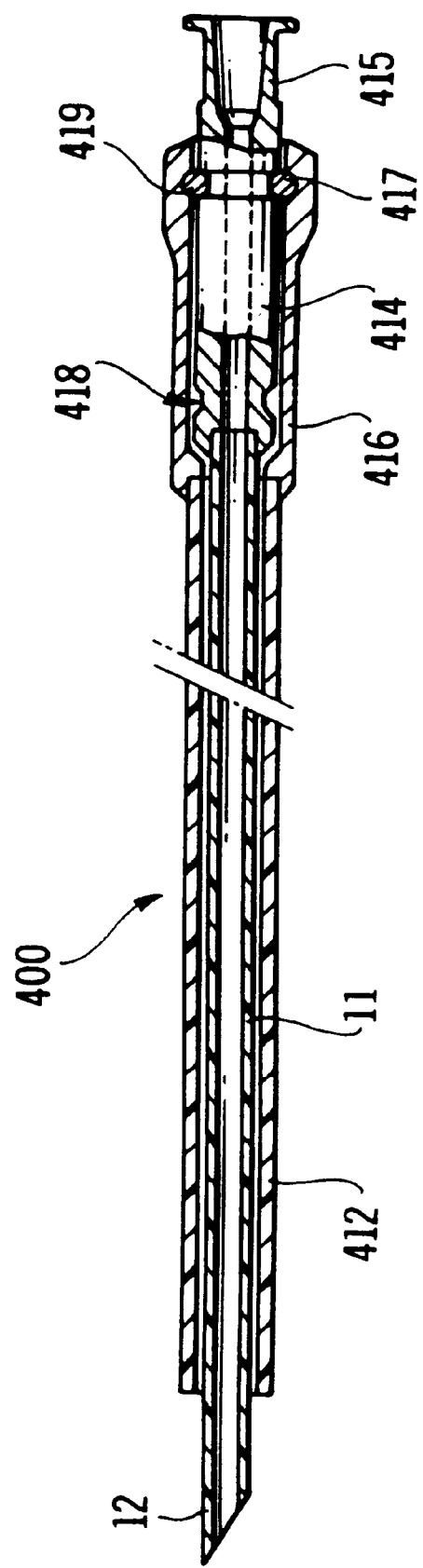
FIG. 21 is a sectional side view of the injector instrument of FIG. 20 in a different state.

In FIG. 21, the O-ring 417 is engaged with the second click groove 419 and the needle portion 12 projects from the cover tube 412 by a predetermined amount. The injection of a fluid into an affected part is done in this state.

As shown in FIG. 22, the injector instrument 400 is inserted in the forceps channel 2, the needle portion 12 is extended from the cover tube 412 as described above, and the needle portion 12 is stuck into the inner wall of the body cavity C. Then, an injector 14, is connected to the mouth piece 415, and is used to inject a medical fluid through the fluid supply tube 11.

Based on the experiments described above, the cover tube 412 may be made of, for example, tetra-fluoroethylene (PFA) having Shore hardness of D60–64 and the fluid supply tube 11 (in particular, the needle portion 12) may be made of, for example, polyimide (Rockwell hardness: R129) such that the needle portion 12 will not stick in the cover tube 412 when the needle portion 12 moves through the cover tube 412.

As described with respect to the experiments above, even if the needle portion 12 has a hardness that is greater than that of the cover tube 412, the needle portion 12 can proceed through the cover tube 412 without sticking in a wall of the cover tube 412.

Figure 23:
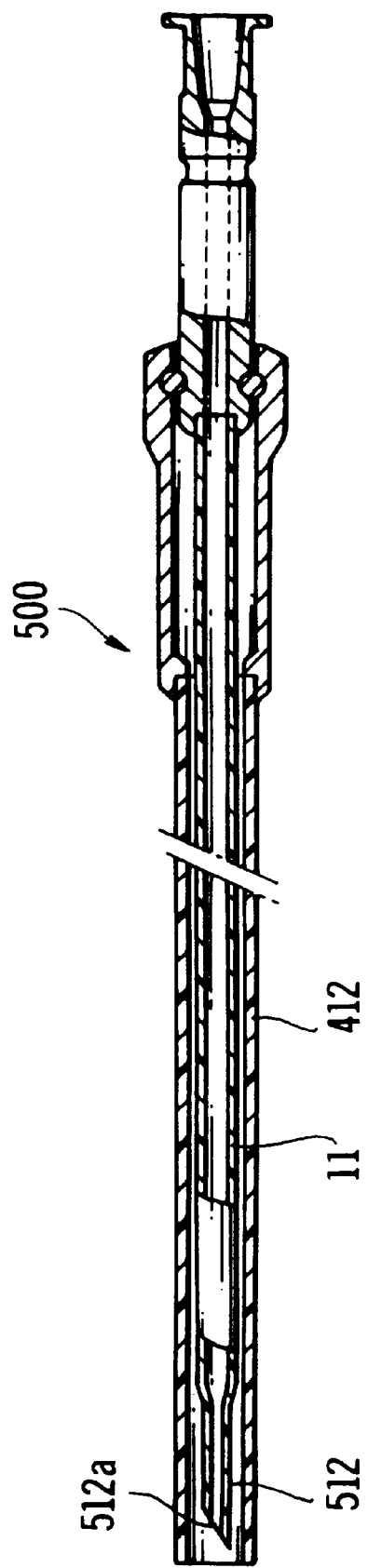
FIG. 23 is a sectional side view of an injector instrument according to a sixth embodiment of the invention.
Figure 24:
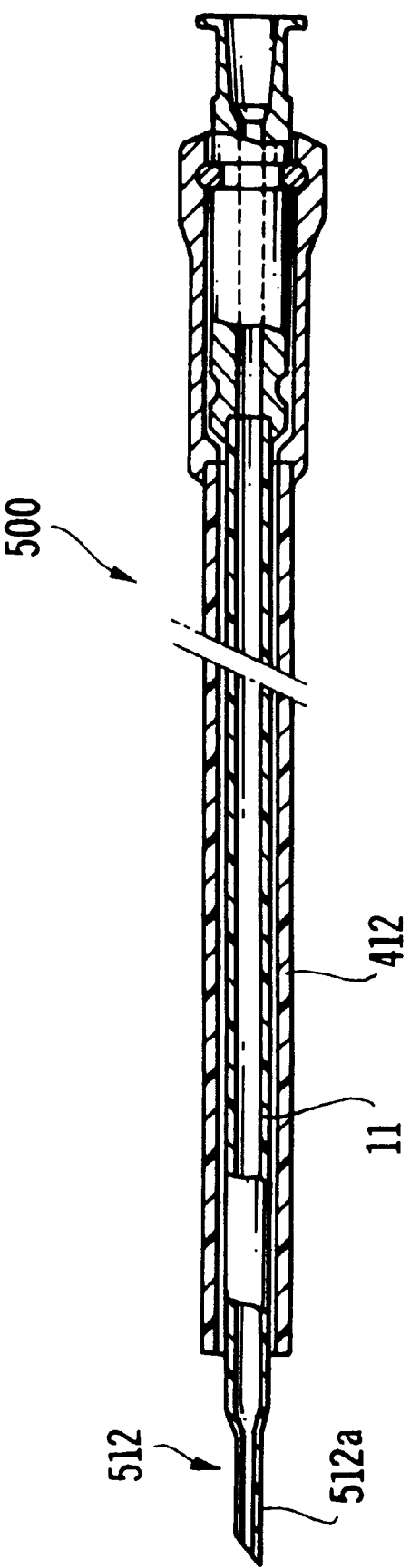
FIG. 24 is a sectional side view of the injector instrument of FIG. 23 in a different state.

FIGS. 23 and 24 show an injector instrument 500 according to a sixth embodiment. In the sixth embodiment, a needle portion 512 is formed to have a smaller diameter portion 512a similar to the needle portion 312 of the fourth embodiment described above. With this structure, the smaller diameter portion is more flexible and more easily bends to follow the curvature of the cover tube 412. Further, with this arrangement, the depth to which the needle portion 512 enters the wall of the body cavity C is restricted to the length of the smaller diameter portion 512a, and accordingly the amount that the needle portion 512 sticks into the wall of the body cavity C can be set as desired. In this embodiment, the length and the diameter of the small diameter portion 512a may be designed depending on the particular use or purpose of the injector instrument 500.

Of course, relevant modifications and variations described with regard to other embodiments herein may be applied to the fifth and sixth embodiments.

FIG. 25 shows a schematic sectional view of an injector instrument 600 according to a seventh embodiment of the invention. The injector instrument 600 is similar to the injector instrument 10 of the first embodiment, except that a fluid supply tube 611 of the injector instrument 600 is provided, at a distal end portion thereof, with a gently curved portion 611a. Since the fluid supply tube 611 is made of a synthetic resin the curved portion 611a may be easily formed.

Alternatively, the curved portion 611a may include the needle portion 12. Further, the positional relationship between an end side plane of the needle portion 12 and the direction of curvature of the curved portion 611a is not necessarily as shown in FIG. 25. FIG. 26 shows an alternative arrangement in which the positional relationship between the end side plane of the needle portion 12 and the direction of curvature of the curved portion 611a is opposite to the case shown in FIG. 25.

Figure 27:
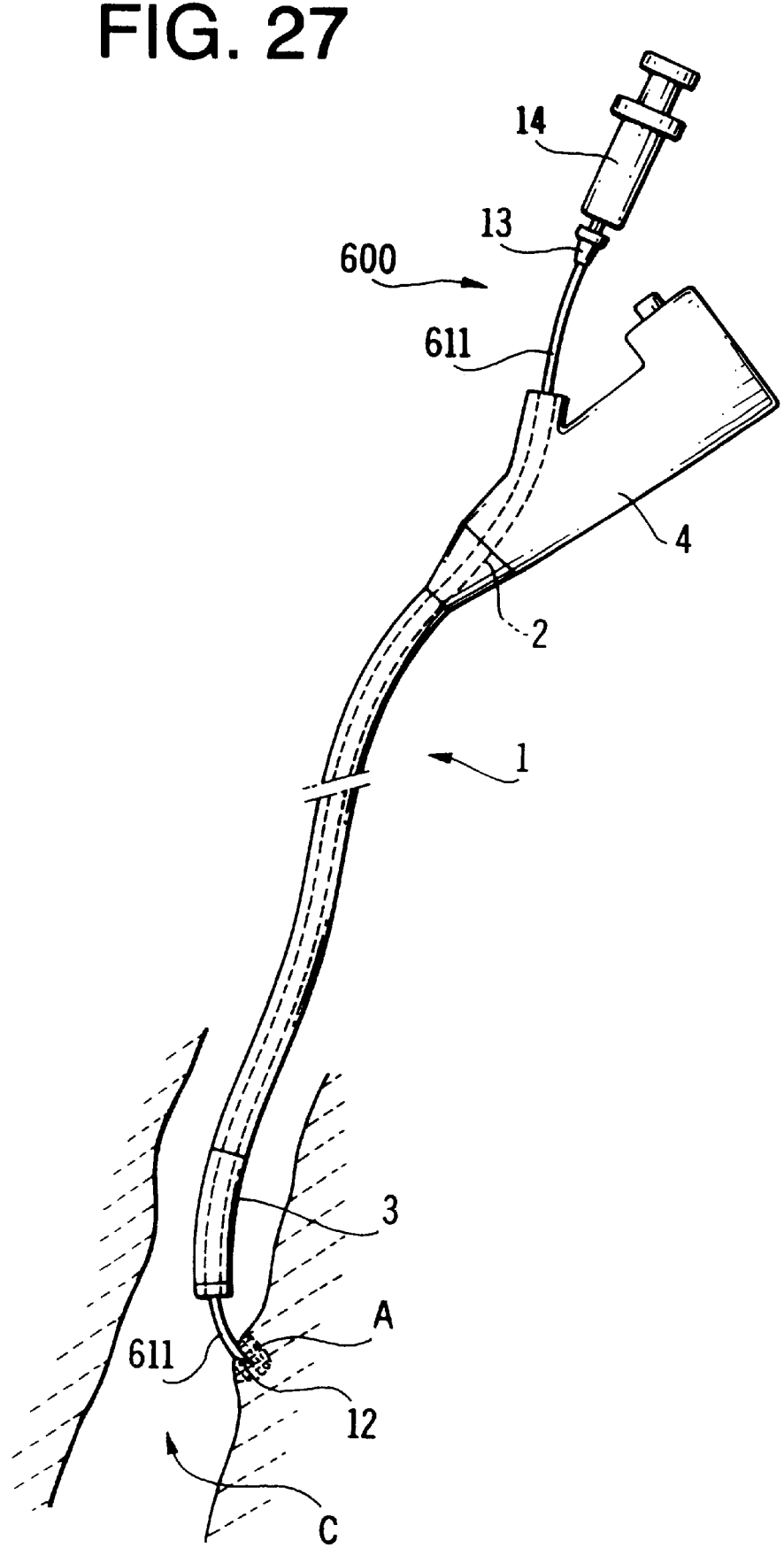
FIG. 27 is a side view of an endoscope having a forceps channel in which the injector instrument of FIG. 25 is inserted.

As shown in FIG. 27, the injector instrument 600 is inserted through the forceps channel 2 of the endoscope 1. The fluid supply tube 611 and the needle portion 12 are projected from the distal tip of the endoscope 1 and stuck in an affected part A of the wall of the body cavity C. Then, from the injector 14 connected to the fluid supply portion 13, fluid is supplied through the fluid supply tube 611 to the affected part A.

Since the fluid tube 611 is provided with the curved portion 611a, the needle portion 12 can be more easily positioned at closer to a right angle with respect to the affected part A prior to insertion. In other words, the angle at which the needle portion 12 enters the affected part A is greater than an angle formed between the fluid tube 611 and the wall of the body cavity C. Thus, without the need for any remote operation for bending the needle portion 12, the attitude of the needle portion 12 with respect to the affected part A is easily set appropriately.

In this embodiment the injector instrument 10 does not have a cover tube, such that even if the forceps channel has a relatively small diameter, the diameter of the fluid tube 611 remains sufficiently large that a sufficient amount of medical fluid can be injected easily.

As shown in FIG. 27, the endoscope 1, includes a bendable portion 3 which is bent arbitrarily in accordance with an operation of a manipulation portion 4. When the bendable portion 3 is bent as shown in FIG. 27, prior to extending the curved portion 611a from the forceps channel 2, the curved portion 611a follows the curvature of the bendable portion 3 due to the elastic force driving the curved portion 611a to return to a neutral curved state. That is, the fluid supply tube 611 rotates inside the forceps channel 2 so that the curved direction of the curved portion of the fluid tube 611 coincides with the curved direction of the bendable portion 3.

All other aspects of the seventh embodiment are the same as those of the first embodiment and the modifications and alternative structures described with regard to the first embodiment may be applied to the seventh embodiment. Further, a curved portion (not shown) similar to the curved portion 611a of the seventh embodiment may be applied to any of the second, third, and fourth embodiments in a similar way.

Figure 28:
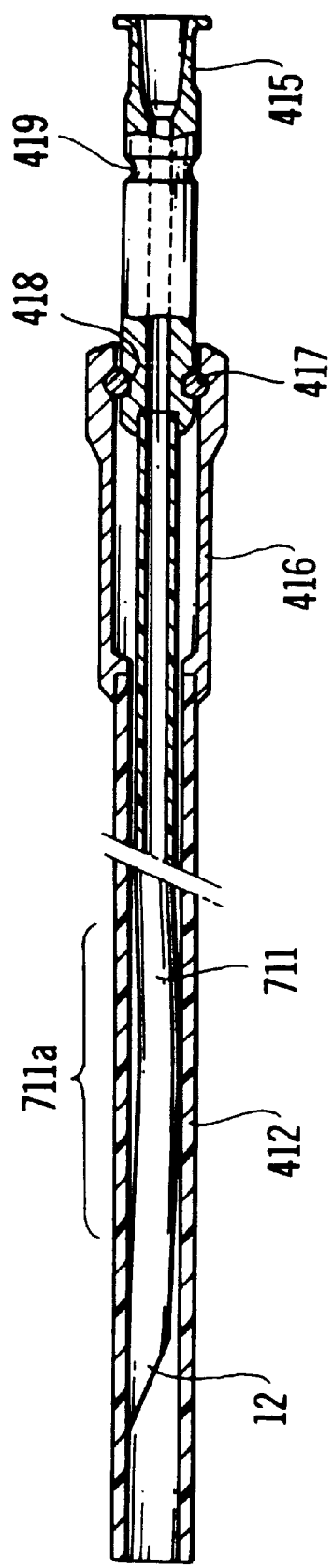
FIG. 28 is a sectional side view of an injector instrument according to an eighth embodiment of the invention.

FIG. 28 shows an injector instrument 700 according to an eighth embodiment. The injector instrument 700 is similar to that of the fifth embodiment except that a distal end portion of the fluid tube 711 is provided with a curved portion 711a that is similar to the curved portion 611a of the seventh embodiment.

Figure 29:
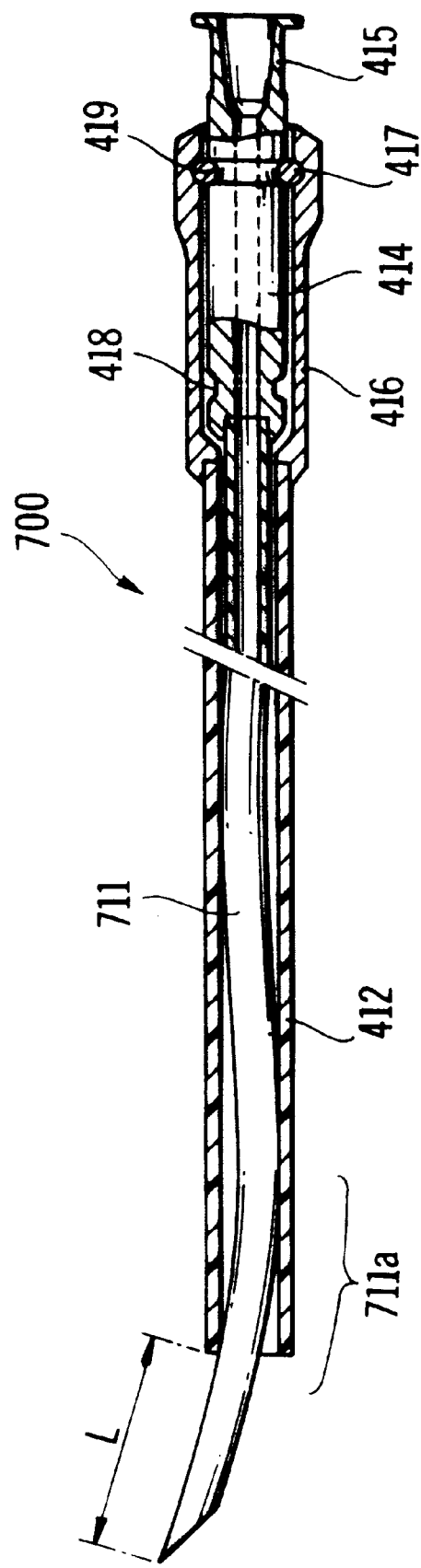
FIG. 29 is a sectional side view of the injector instrument of FIG. 28 when a needle portion is extended.

FIG. 29 shows the injector instrument 700 when the needle portion 12 is extended from the cover tube 412 by a distance L. As is shown in FIG. 29, the fluid tube 711 elastically returns to a neutral curved state when extended from the cover tube 412.

Figure 30:
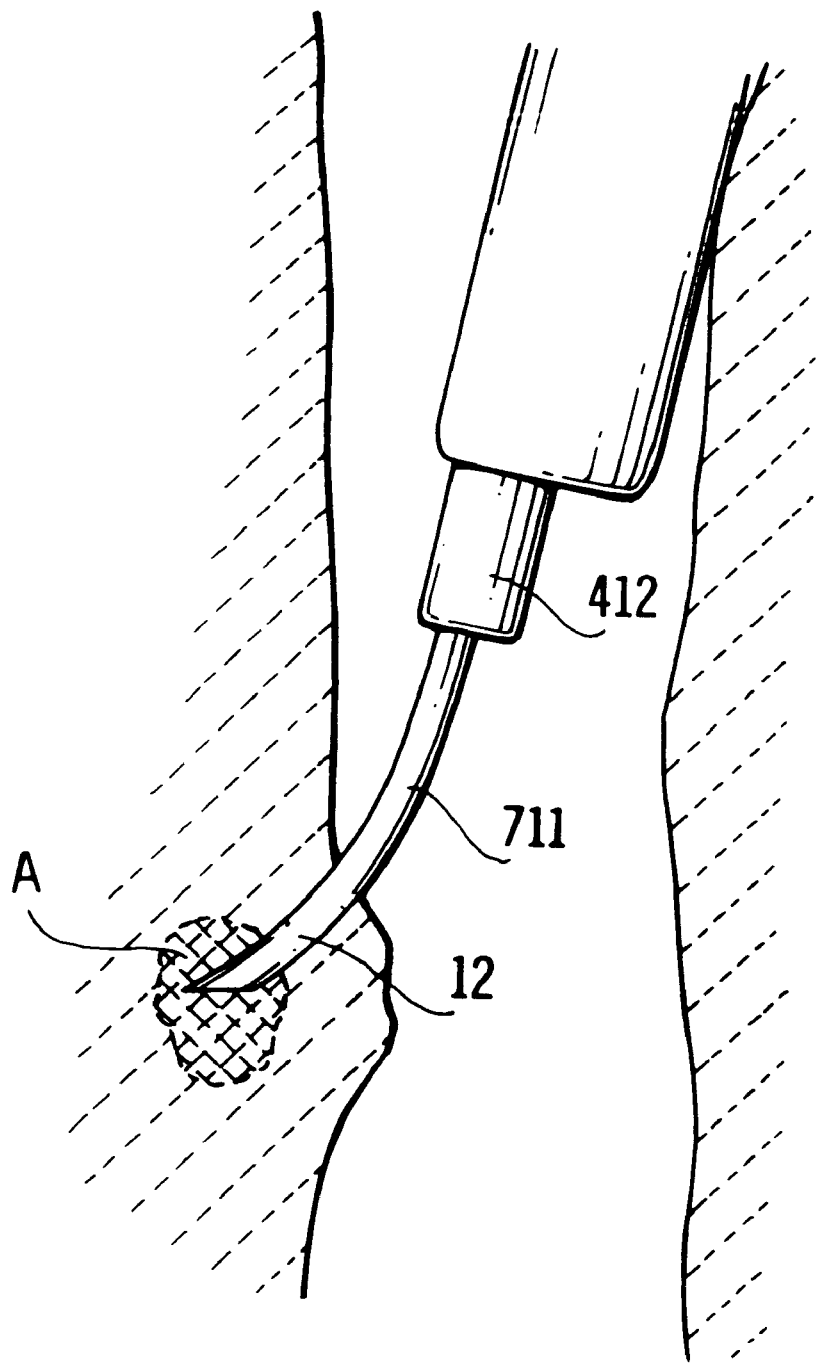
FIG. 30 is a schematic view illustrating the use of the injector instrument of FIG. 28.

FIG. 30 shows a situation where the injector instrument 700 is used. The cover tube 412 is inserted through the forceps channel 2 of the endoscope 1. The needle portion 12 is projected from the cover tube 412. Since the fluid supply tube 711 is provided with the curved portion 711a, the needle portion 12 may be inserted in the affected part A from a more appropriate angle. After the needle portion 12 is stuck in the affected part A, the medical fluid is supplied through the fluid supply tube 711.

All other aspects of the eighth embodiment are the same as those of the fifth embodiment and the modifications and alternative structures described with regard to the fifth embodiment may be applied to the eighth embodiment. Further, a curved portion (not shown) similar to the curved portion 711a of the eighth embodiment may be applied to the sixth embodiment in a similar way.

Figure 31:
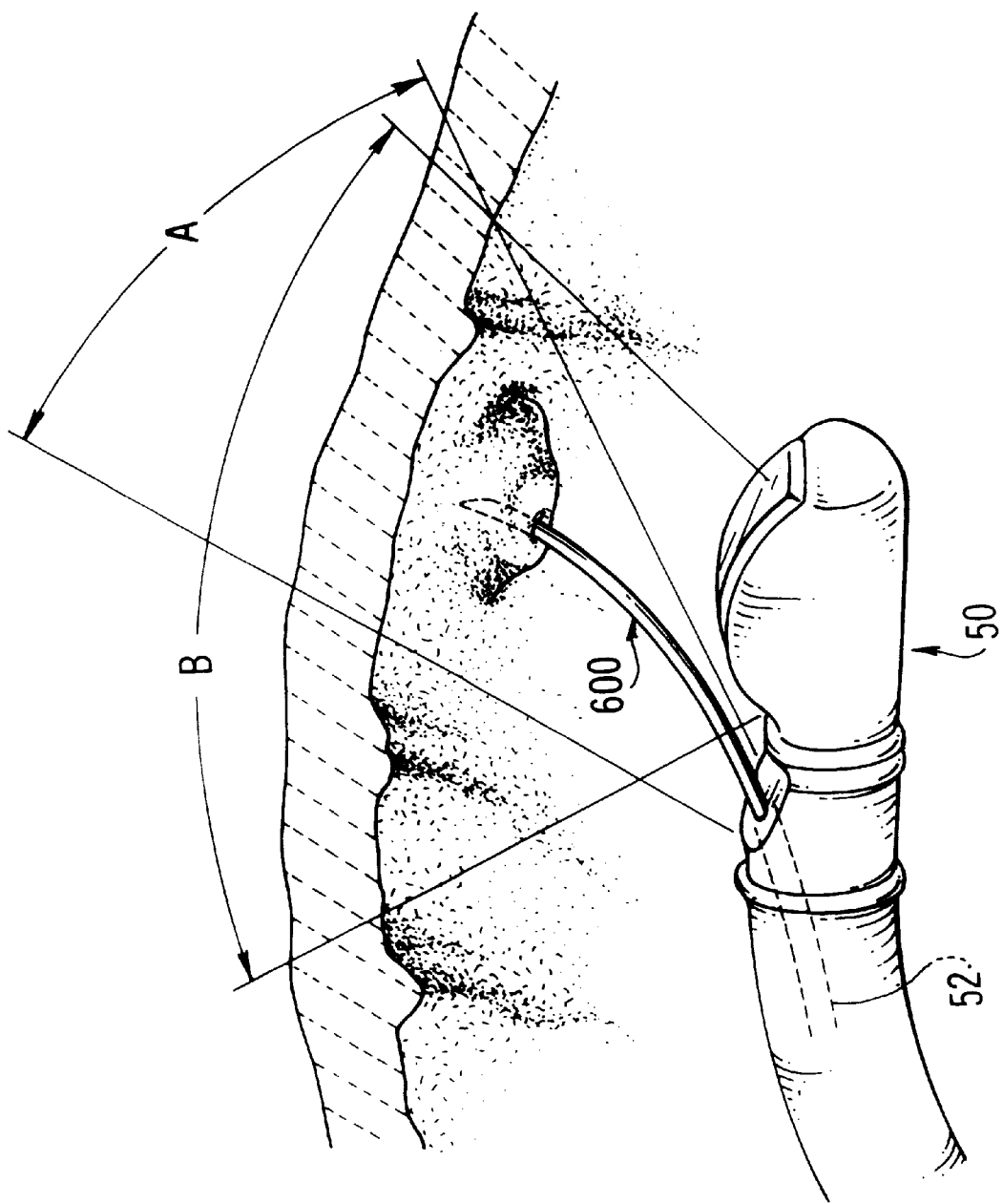
FIG. 31 is a schematic view illustrating the use of the injector instrument of FIG. 25 with an ultrasonic endoscope.
Figure 32:
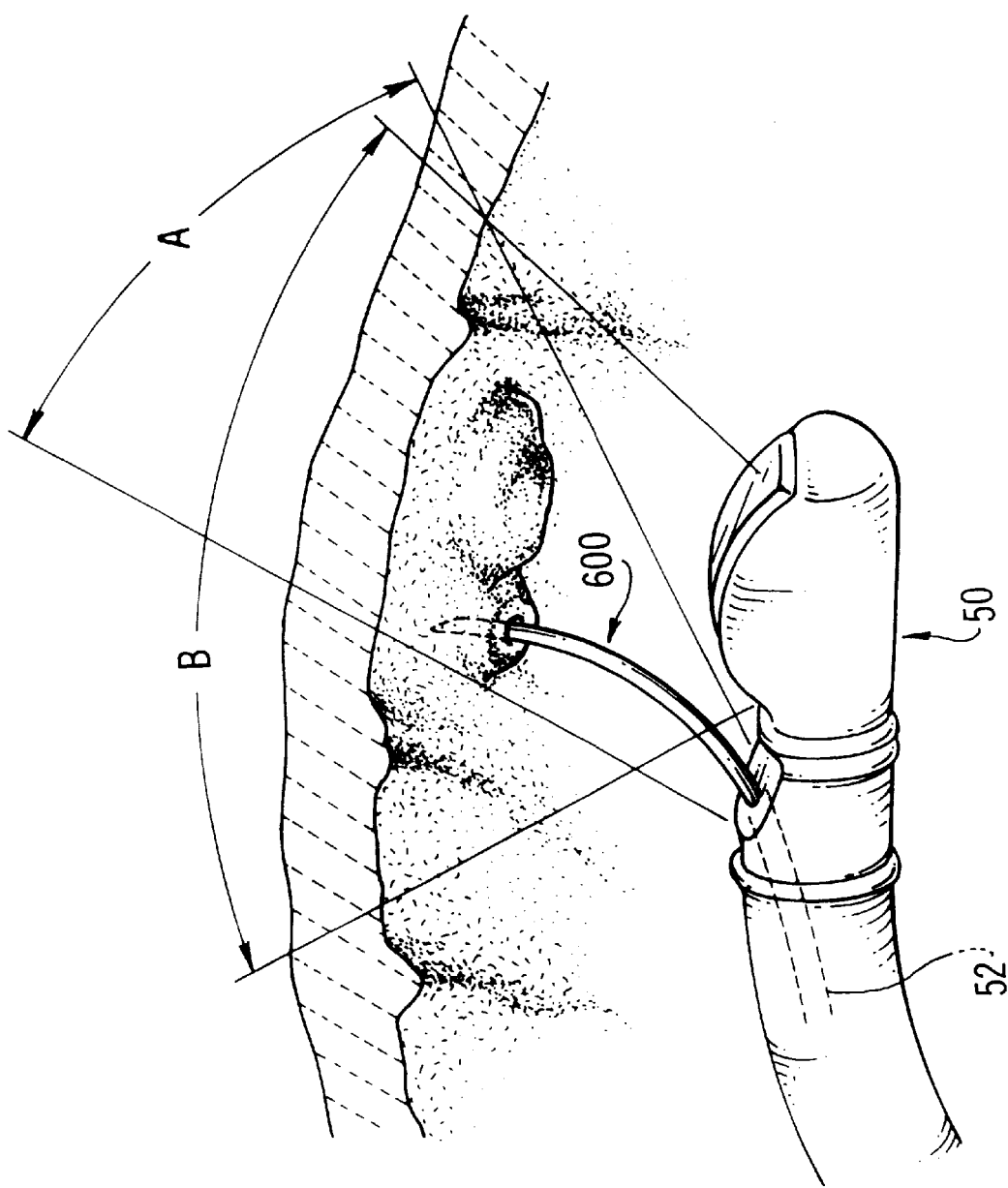
FIG. 32 is a schematic view illustrating the use of a variation of the injector instrument of FIG. 25 with the ultrasonic endoscope.

FIG. 31 shows a situation where the injector instrument 600 according to the seventh embodiment is inserted in a forceps channel 52 of an ultrasonic endoscope 50. In this case, the needle portion 12 of the injector instrument 600 is positioned within a visually observable range A, and further located at about the center of an ultrasonic sectional image observable range B. Thus, appropriate treatment can be administered. In this case, preferably, the radius of curvature of the curved portion 611a of the injector instrument 600 is made smaller, as shown in FIG. 32, so that the needle portion 12 may be more closely centered in the central area of the ultrasonic sectional image observable range B. Similar considerations apply with regard to the injector instrument 700 according to the eighth embodiment.

In the seventh and eighth embodiments, since the distal end portion of the injector instrument is formed to have a curved portion, the needle portion can be inserted in the affected part from an appropriate angle. Further, the injector instrument does not require any additional mechanism for bending the injector instrument and thus has a simple structure providing durability and low-cost manufacturing.

Figure 33:
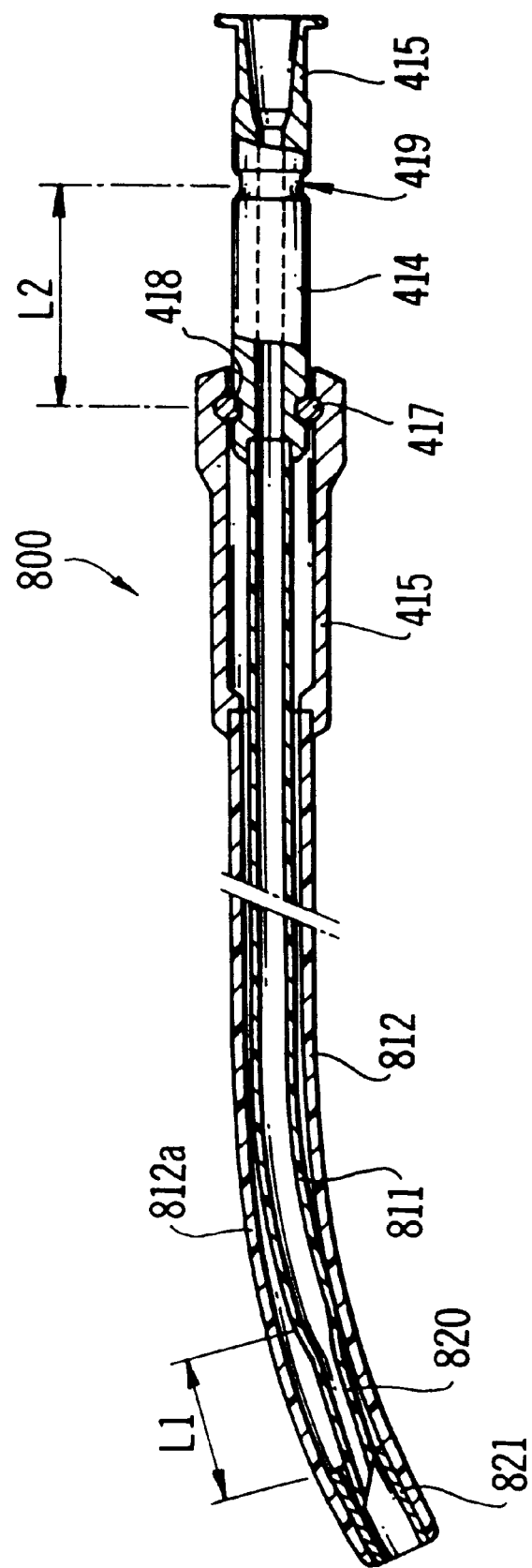
FIG. 33 is a sectional side view of an injector instrument according to an ninth embodiment of the invention.

FIG. 33 shows an injector instrument 800 according to a ninth embodiment of the invention.

The injector instrument 800 is provided with a cover tube 812 which is formed by closely winding stainless steel wire at a predetermined diameter.

A fluid tube 811 is slidably inserted inside the cover tube 812. The fluid tube 811 is a flexible tube made of synthetic resin, having a predetermined elasticity. The distal end portion of the fluid tube 811 is formed as a needle portion 820 having a length L1 having a smaller diameter and the tip of the needle portion 820 is obliquely cut to form a point. The fluid tube 811 is neutrally straight.

When the cover tube 811 is made (i.e., the stainless steel wire is wound), a preload is applied, such that the main part of the cover tube 811 is neutrally straight but bent portion 812a at the distal end portion thereof is provided with a slight bend. That is, the shape of the cover tube 812 in a neutral condition is as shown in FIG. 33. In FIG. 33, the fluid tube 811 is also bent, however, this is due to the curvature of the cover tube 812.

Figure 34:
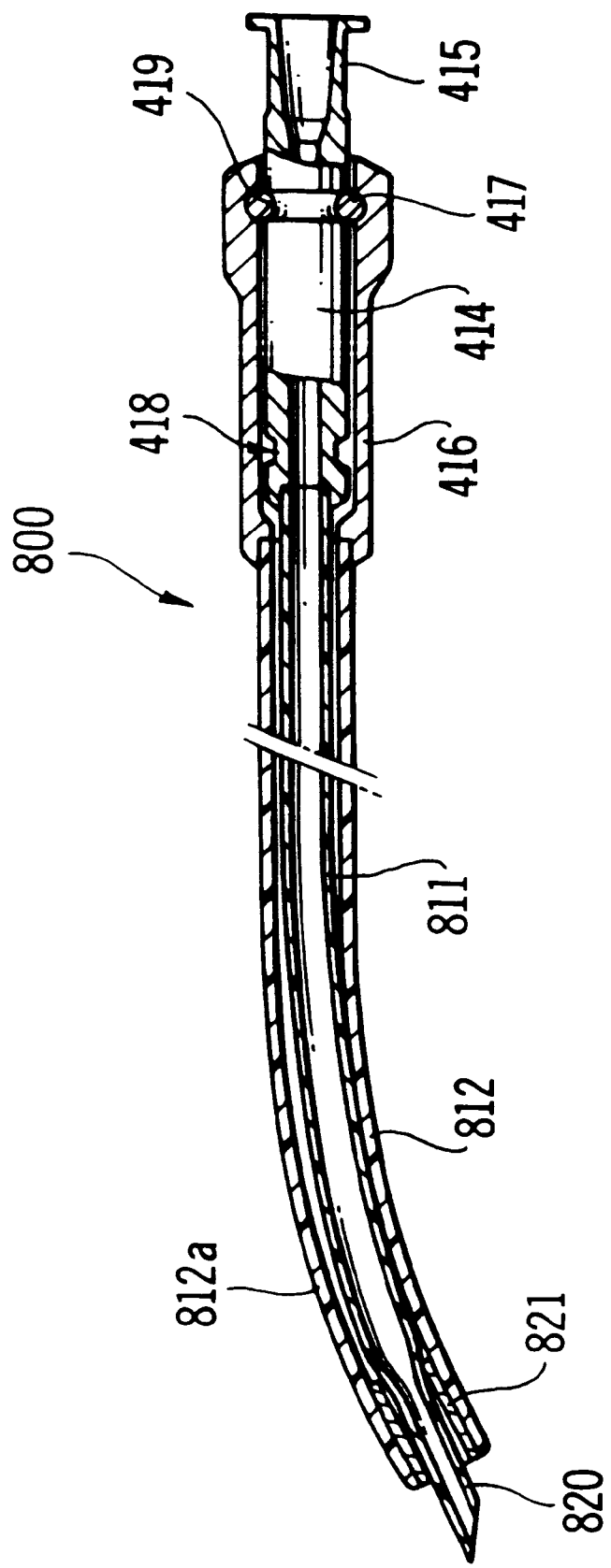
FIG. 34 is a sectional side view of the injector instrument of FIG. 33 when a needle portion is extended.

At the distal end of the cover tube 812, a stopper 821 is provided. The stopper 821 has an opening formed to allow the needle portion 820 to pass through but prevent the fluid tube 811 from passing through. The stopper 821 functions when the needle portion 820 is extended from the cover tube 812, and the amount of the needle portion 820 extending from the cover tube 812 is a constant, as shown in FIG. 34. The stopper 821 may be fixed to the cover tube by, for example, an ultrasonic welding method.

The cover tube 812 and the fluid tube 811 may be formed in a similar manner to related elements in the above embodiments and may have relevant modified or alternative structures applied accordingly.

Figure 35:
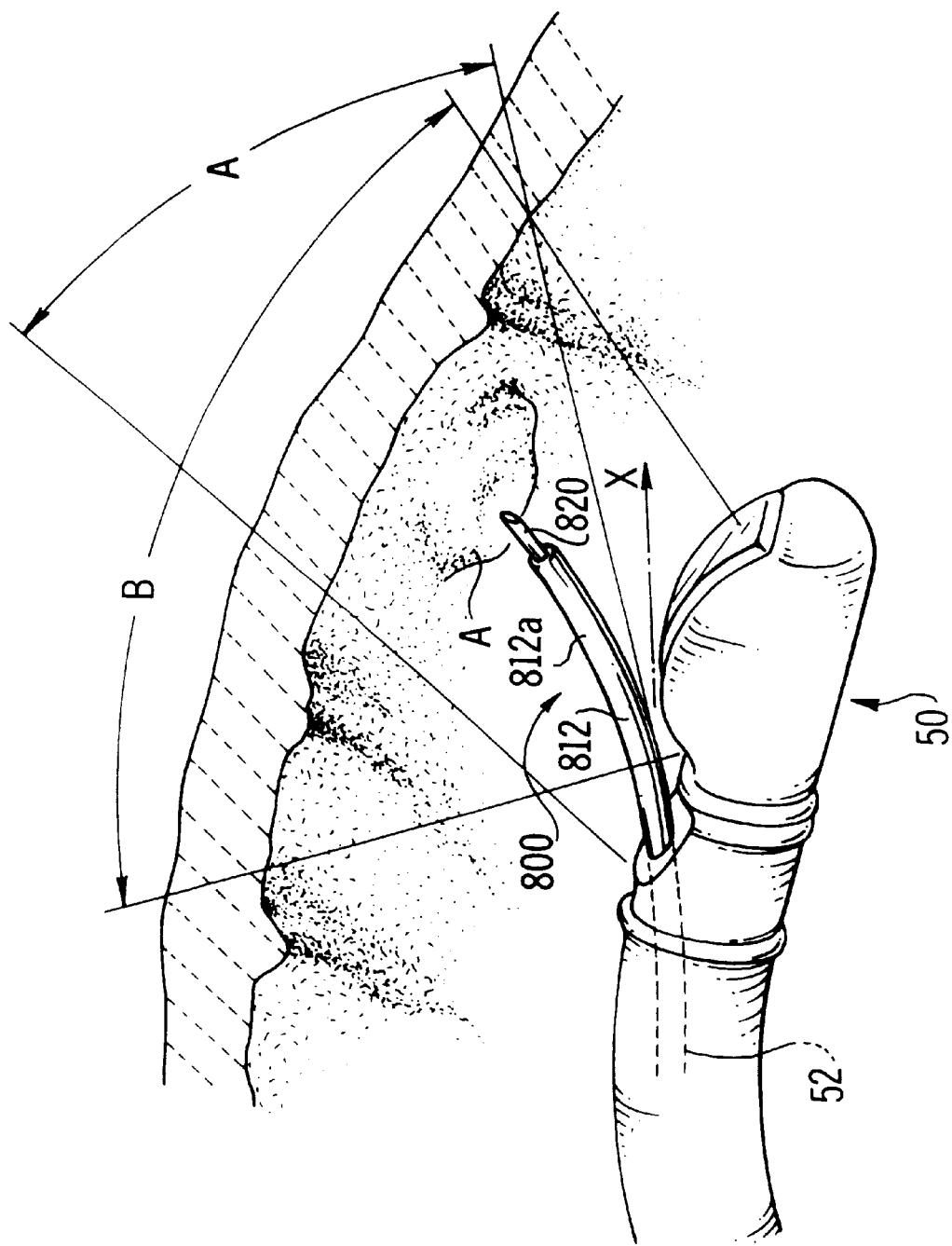
FIG. 35 is a schematic view illustrating the use of the injector instrument of FIG. 33 with the ultrasonic endoscope.

FIG. 35 shows the injector instrument 800 when inserted in the forceps channel 52 of the ultrasonic endoscope 50. The needle portion 820 is inserted in the wall of the human cavity, and a medical fluid from an injector (not shown) connected to the mouth piece 415 is supplied through the fluid tube 811 to the affected part A.

In FIG. 35, if the cover tube 812 were not provided with the curved portion 812a, the needle portion 820 would extend in the direction indicated by the arrow X. However, since the cover tube 812 is provided with the curved portion 812a, it is possible to insert the needle portion 820 into the affected part A at a larger angle and in a position which is located at about a central position with respect to the optically observable area A as well as with respect to the ultrasonic scanning area B.

Figure 36:
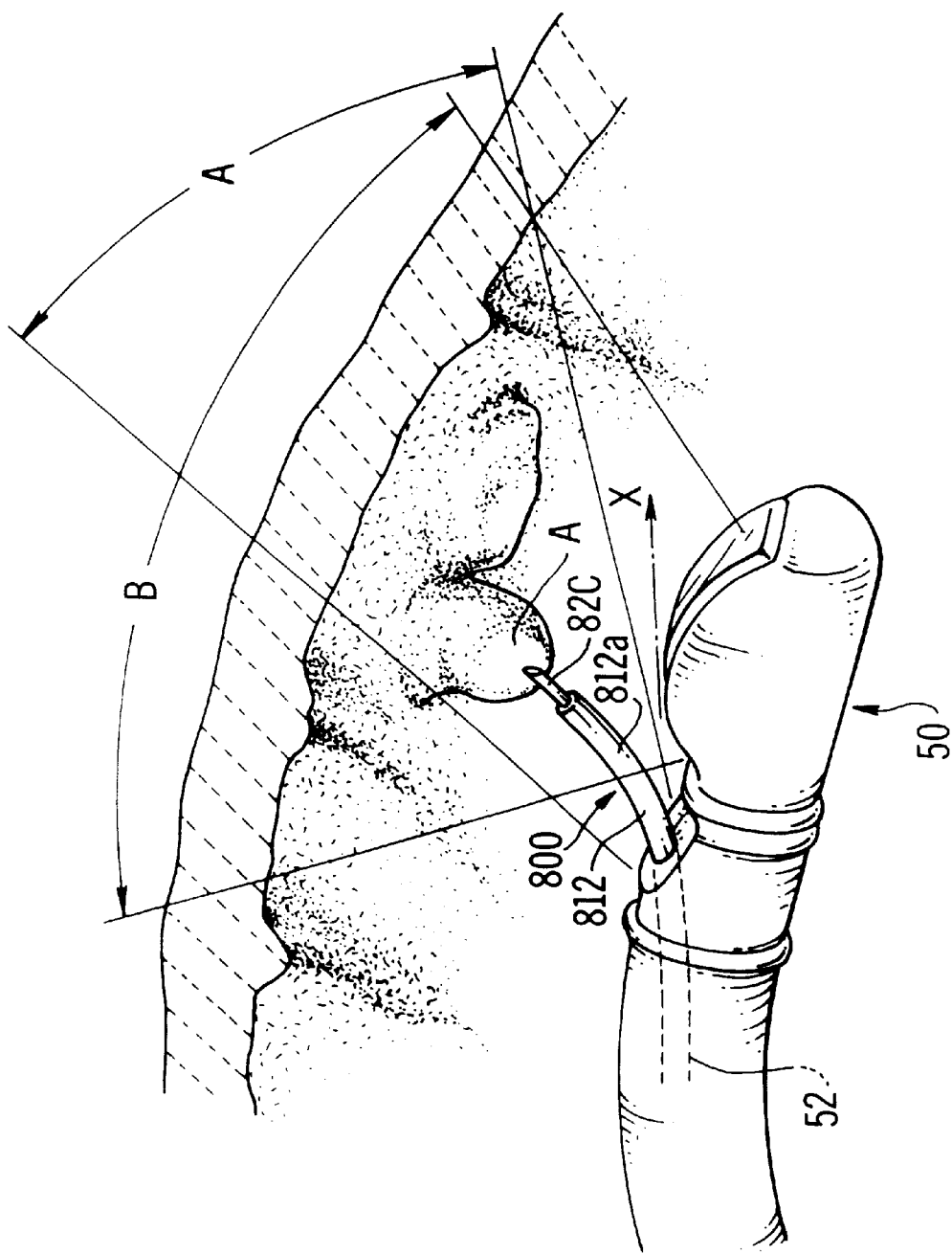
FIG. 36 is a schematic view illustrating the use of a variation of the injector instrument of FIG. 33 with the ultrasonic endoscope.

As shown in FIG. 36, if the curved portion 812a is curved more, even if the affected part A is in a narrower body cavity and therefore closer to the ultrasonic endoscope 50, the needle portion 820 can be inserted in the affected part A at about a central portion with respect to the optically observable area A as well as with respect to the ultrasonic scanning area B at an appropriate angle.

Figure 37:
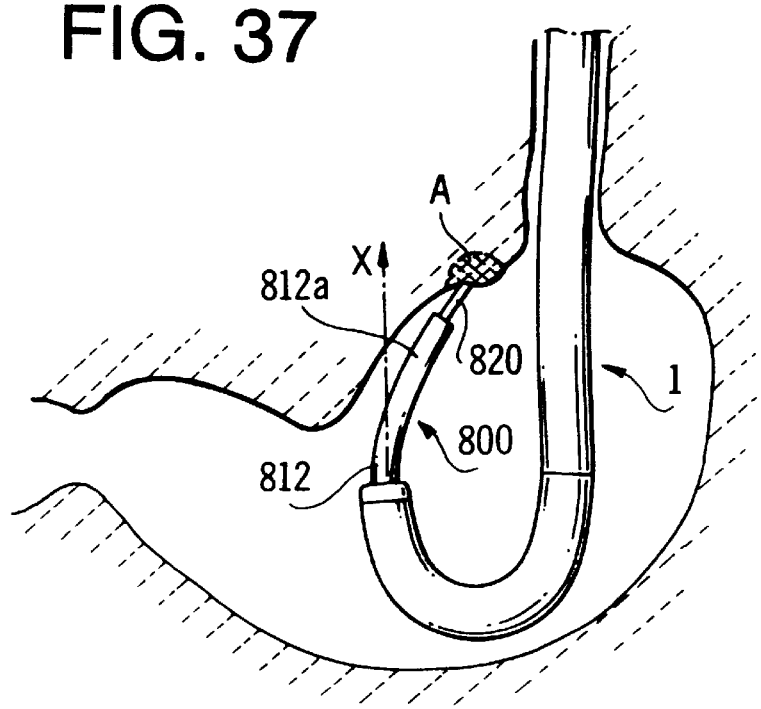
FIG. 37 is a schematic view illustrating the use of the injector instrument of FIG. 33 in the endoscope in a gastrointestinal tract.

FIG. 37 shows an example where the injector instrument 800 is used in an endoscope 1 for a gastrointestinal tract. As shown in FIG. 37, if the injector instrument 800 is provided with a curved portion 812a having an appropriate length and curvature, the needle portion 820 can be inserted in the affected part A at an appropriate angle. In FIG. 37, the arrow X represents the direction in which the cover tube 812 would extend if the curved portion 812a were not provided.

FIGS. 38 through 41 show modifications of the cover tube 812. In FIGS. 38 through 41, a modified cover tube 812' is further provided with an easy-to-bend (ETB) portion 812b. The ETB portion 812b is located at the bendable portion 3 of the endoscope 1 when the curved portion 812a is extended from the forceps channel 2 of the endoscope 1. In these examples, the ETB portion 812b bends easily at a greater radius of curvature than the curved portion 812a.

Figure 38:
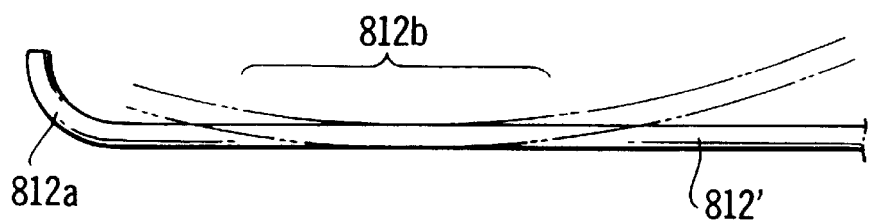
FIG. 38 is a side view of a modified cover tube of the injector instrument of FIG. 33.
Figure 39:
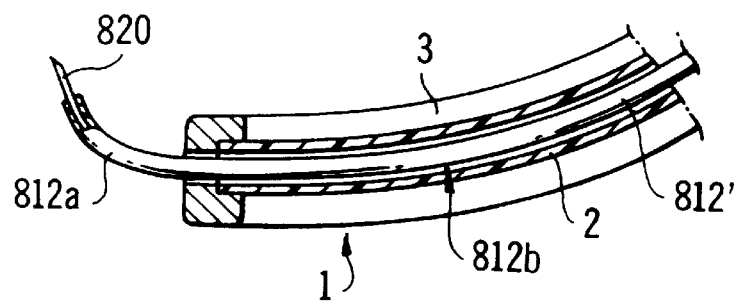
FIG. 39 is a schematic view showing the modified cover tube of FIG. 38 in the forceps channel.

In FIG. 38, the curved portion 812a and the ETB portion 812b are curved in the same direction. As shown in FIG. 39, when the cover tube 812' is inserted in the endoscope 1, the cover tube 812' rotates inside the forceps channel 2 of the endoscope 1 so that the ETB portion 812b follows the curvature of the bendable portion 3. In this example, accordingly, the needle portion 820 is directed in the direction in which the bendable portion 3 of the endoscope 1 is curved.

Figure 40:
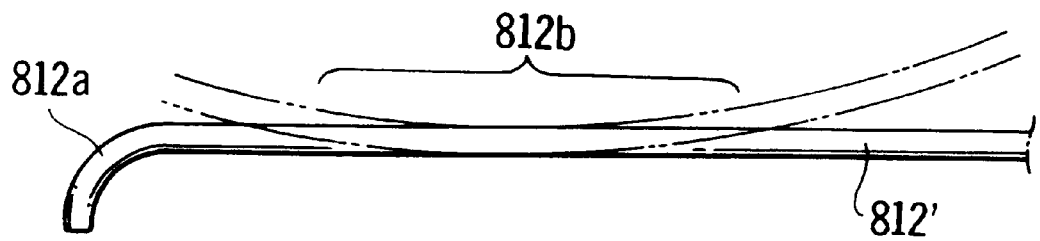
FIG. 40 is a side view of an alternative structure for the modified cover tube of FIG. 38.
Figure 41:
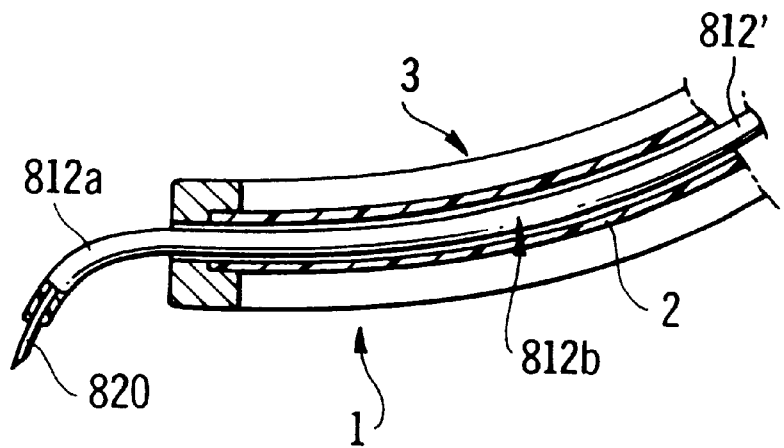
FIG. 41 is a schematic view showing the alternative modified cover tube of FIG. 40 in the forceps channel.

In FIG. 40, the curved portion 812a and the ETB portion 812b curve in opposite directions. Accordingly, as shown in FIG. 41, the needle portion 820 is directed in an opposite direction to that in which the bendable portion 3 is curved.

FIGS. 42 and 43 show an alternative modification of the cover tube 812. In FIGS. 42 and 43, a modified cover tube 812" is further provided with a second curved portion 812b'. The second curved portion 812b' is located at the bendable portion 3 of the endoscope 1 when the curved portion 812a is extended from the forceps channel 2 of the endoscope 1. In these examples, the second curved portion 812b' is pre-bent at a greater radius of curvature than the curved portion 812a.

In FIG. 42, the curved portion 812a and the second curved portion 812b' are curved in the same direction and in FIG. 43, the curved portion 812a and the second curved portion 812b' curve in opposite directions.

FIG. 44 shows an example where the injector instrument 800 having, in this example, a modified cover tube 812' as described above is used in an endoscope 1 for a large intestine. As shown in FIG. 44, the cover tube 812' rotates in the forceps channel 2 such that the ETB portion 812b matches with the bendable portion 3 of the endoscope 1 and the curved portion 812a directs the needle portion 820 for insertion in the affected part A at an appropriate angle. In FIG. 44, the arrow X represents the direction in which the cover tube 812' would extend if the curved portion 812a were not provided.

Figure 45:
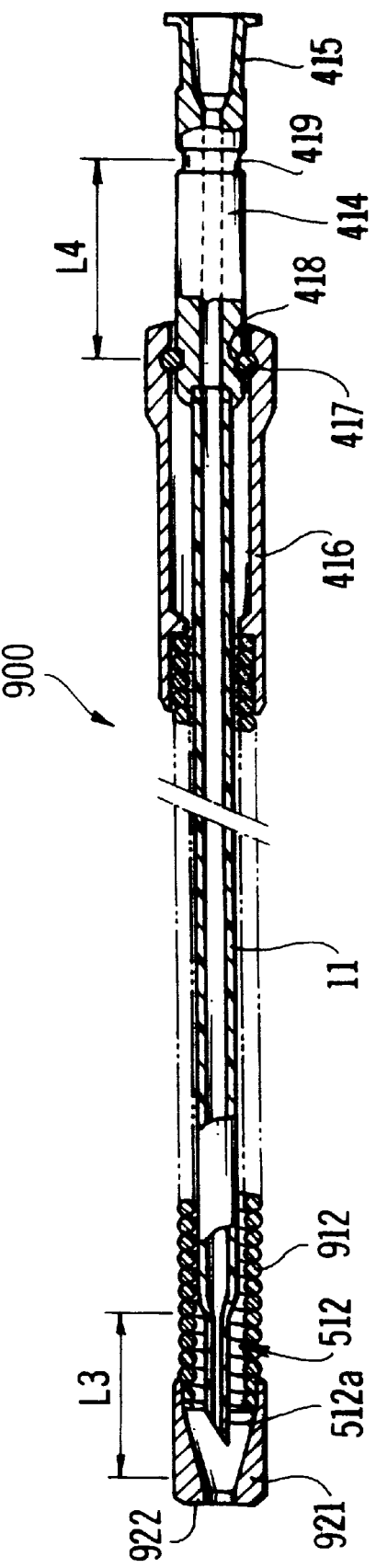
FIG. 45 is a sectional side view of an injector instrument according to a tenth embodiment of the invention.

FIG. 45 shows an injector instrument 900 according to a tenth embodiment of the invention. The injector instrument 900 is similar to the injector instrument 500 of the sixth embodiment, except that the injector instrument 900 is provided with a cover tube 912 which is formed by closely winding stainless steel wire at a predetermined diameter. When the cover tube 912 is made (i.e., the stainless steel wire is wound), a preload is applied. Therefore, the cover tube 911 neutrally extends straight.

As in the sixth embodiment, the fluid tube 11 is a flexible tube made of synthetic resin having a predetermined elasticity. The distal end portion of the fluid tube 11 is formed as the needle portion 512 having the smaller diameter portion 512a.

Similar to related embodiments described herein, the fluid tube 11 may be made of nylon (Rockwell hardness: R106–120), polypropylene (Rockwell hardness: R80–110), polyimide resin (Rockwell hardness: R129), or the like. In accordance with necessity, harder or softer materials may also be used. For example, the fluid tube 11 may also be made of superpolymer polyethylene (Rockwell hardness: R50), polypropylene (R80–R102), or polyamide (R119). Thus, it is preferable that the fluid tube 11 as well as the needle portion 12 is made of material which has a hardness within a range of Rockwell hardnesses of R50–R129.

Similar to that described above with regard to the fifth embodiment, the proximal end of the fluid tube 11 is connected to the end of the inner tube 414. The other end of the inner tube 414 is provided with the fluid receiving mouth piece 415. The inner tube 414 is movable along its axis within an outer tube 416, which is connected to the proximal end of the cover tube 912.

On the inner surface of the outer tube 416, at the proximal end thereof, an O-ring 417 is engaged. On the outer surface of the inner tube 414, first and second click grooves 418 and 419 are formed. By engaging the O-ring 417 with either one of the first or second click grooves 418 or 419, the relative position of the inner tube 414 and the outer tube 416 may be adjusted accurately. A predetermined stroke L4 is provided between the first and second click grooves 418 and 419.

In FIG. 45, the O-ring 417 is engaged with the first click groove 418, and the needle portion 13 is retracted inside the cover tube 912. The injector instrument 900 is inserted in or removed from the forceps channel 2 in this condition.

Figure 46:
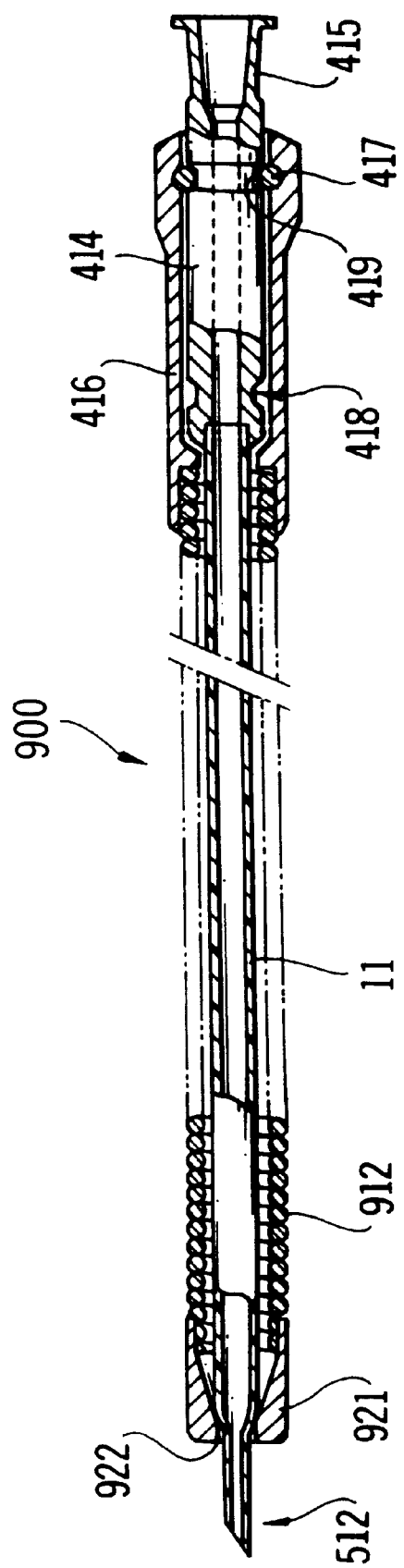
FIG. 46 is a sectional side view of the injector instrument of FIG. 45 when a needle portion is extended.

In FIG. 46, the O-ring 417 engages with the second click groove 419, and the needle portion 413 extends from the end of the cover tube 912 by a predetermined amount. The needle portion 512 is stuck into the affected portion in this condition.

At the distal end of the cover tube 912, a metal tip 921 is fixedly provided. The metal tip 921 is formed such that the needle portion 512 can pass through. In particular, an inner surface of the metal tip 921 is formed to be a gently flared tapered surface leading to an opening 922 formed at the distal end of the metal tip 921.

The inner diameter of the opening 922 is less than the outer diameter of the fluid tube 11. Accordingly, if the fluid tube 11 is pushed forward, the portion of the fluid tube 11 where the needle portion 512 starts contacts the tapered surface and further movement is prohibited.

In this embodiment, a stroke (i.e., a movable amount) L3 of the needle portion 512 is arranged to be slightly less than the stroke L4 of the inner tube 414 such that, even if the injector instrument 900 (i.e., the fluid tube 11) is bent inside the forceps channel 2, the fluid tube 11 can be moved until the portion of the fluid tube 11, where the needle portion 512 starts, contacts the edge of the opening 922. Accordingly, the extension amount of the needle portion 512 (shown in FIG. 46) is constant. Further, since the needle portion 512 is biased by the fluid tube 11 to extend from the metal tip 921, when the needle portion 512 is stuck in the affected part A, the position of the needle portion 512 is maintained.

Figure 47:
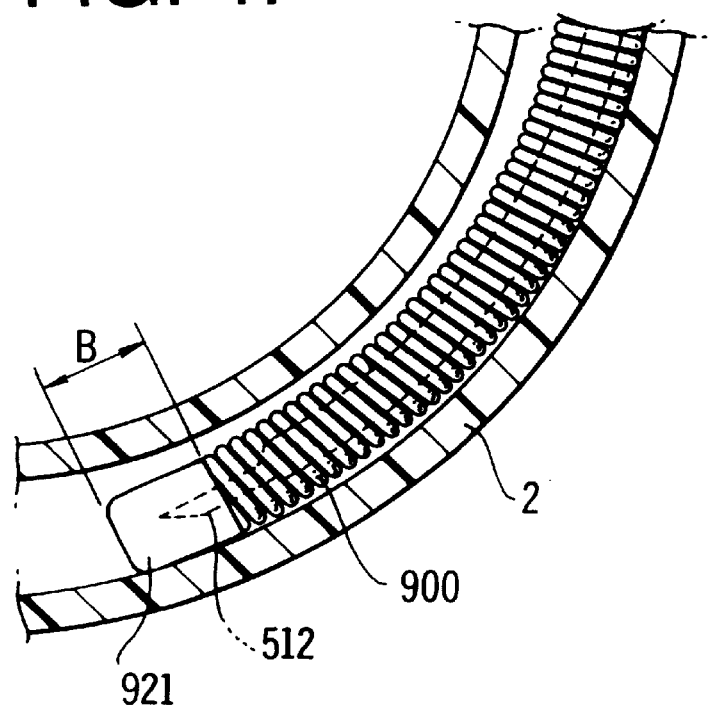
FIG. 47 is a schematic view illustrating the insertion of the injector instrument of FIG. 45 in the forceps channel.
Figure 48:
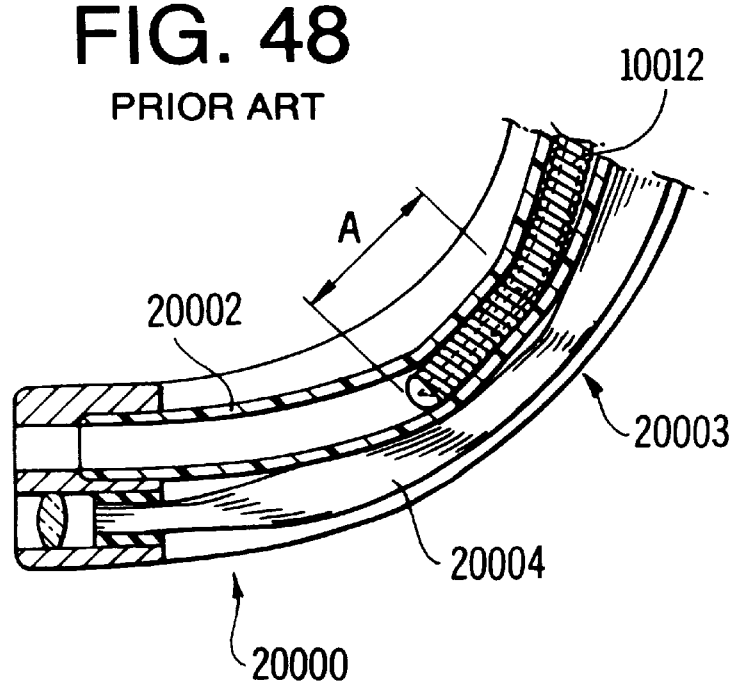
FIG. 48 is a schematic view illustrating the insertion of a conventional injector instrument in a forceps channel.

As shown in FIG. 47, the injector instrument 900 is inserted through the forceps channel 2. At a curved portion of the endoscope 1, the forceps channel 2 may curve in a relatively small radius but the needle portion 512 must still pass through. In this case, since the needle portion 512 is made of a synthetic resin having a certain elasticity and only the tip 921 is made of metal, but has a relatively small length B, the injector instrument 900 is less likely to break through or bind against the wall of the forceps channel 2 even at a curved portion. Accordingly, the injector instrument 900 according to the embodiment does not damage any other elements in the endoscope 1 such as optical fiber or the like, and proceeds inside the forceps channel 2 smoothly.

Figure 49:
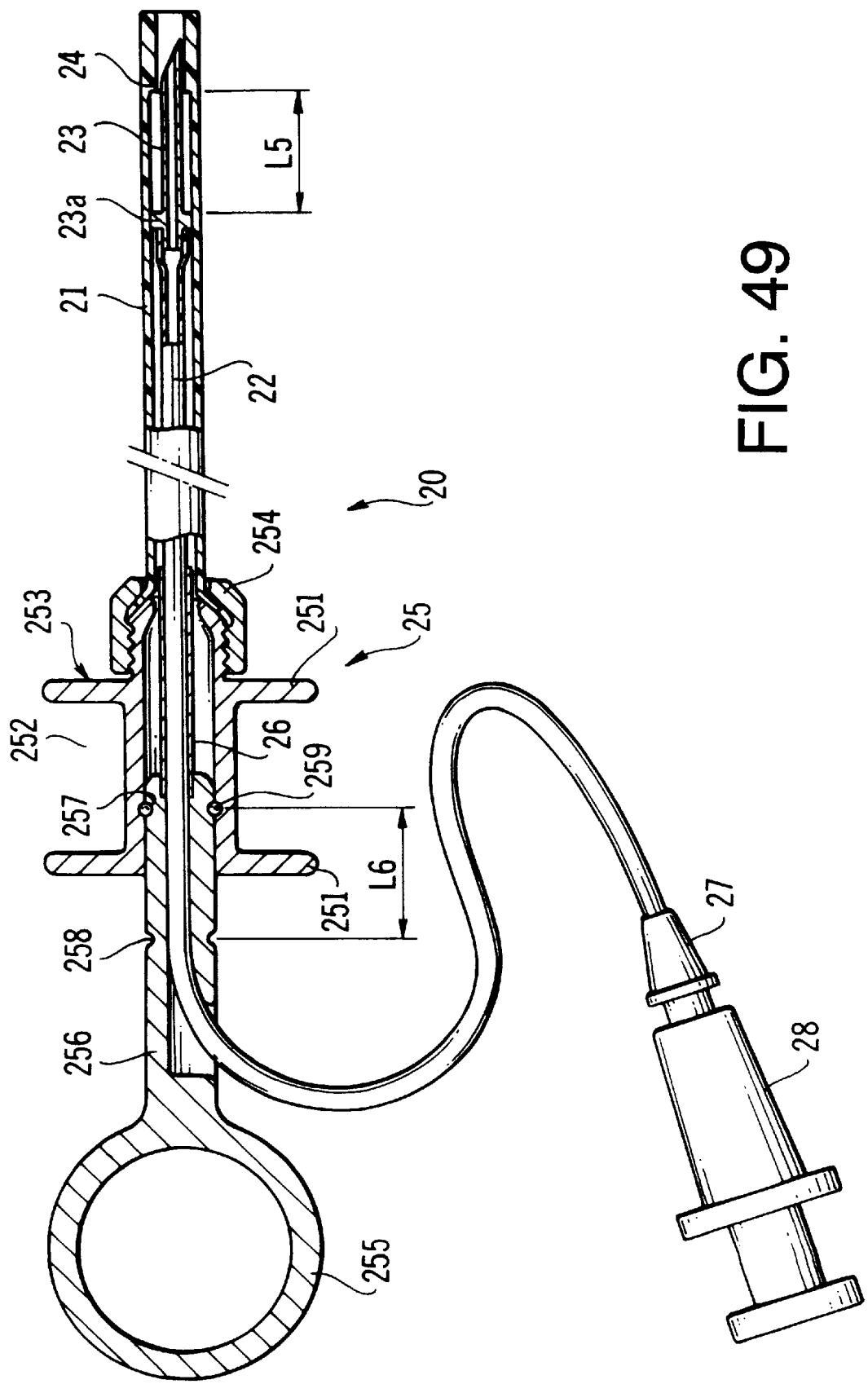
FIG. 49 is a sectional side view of an injector instrument according to an eleventh embodiment of the invention.

FIG. 49 shows an injector instrument 20 according to an eleventh embodiment. The injector instrument 20 is provided with a cover tube 21. The cover tube 21 is a flexible tube made of, for example, TFE resin, and is slidably and detachably inserted in the forceps channel 2 of the endoscope 1 (see FIG. 51). Note that the cover tube 21 is not necessarily a synthetic resin tube, and may be a metal coil tube or the like.

Inside the cover tube 21, a flexible inner tube 22 is inserted. The inner tube 22 is movable along its axis within the cover tube 21. At the tip of the inner tube 22, an injector needle 23 is fixedly connected. By moving the inner tube 22 inside the cover tube 21, the needle 23 is extended from or retracted into the cover tube 21.

Figure 50:
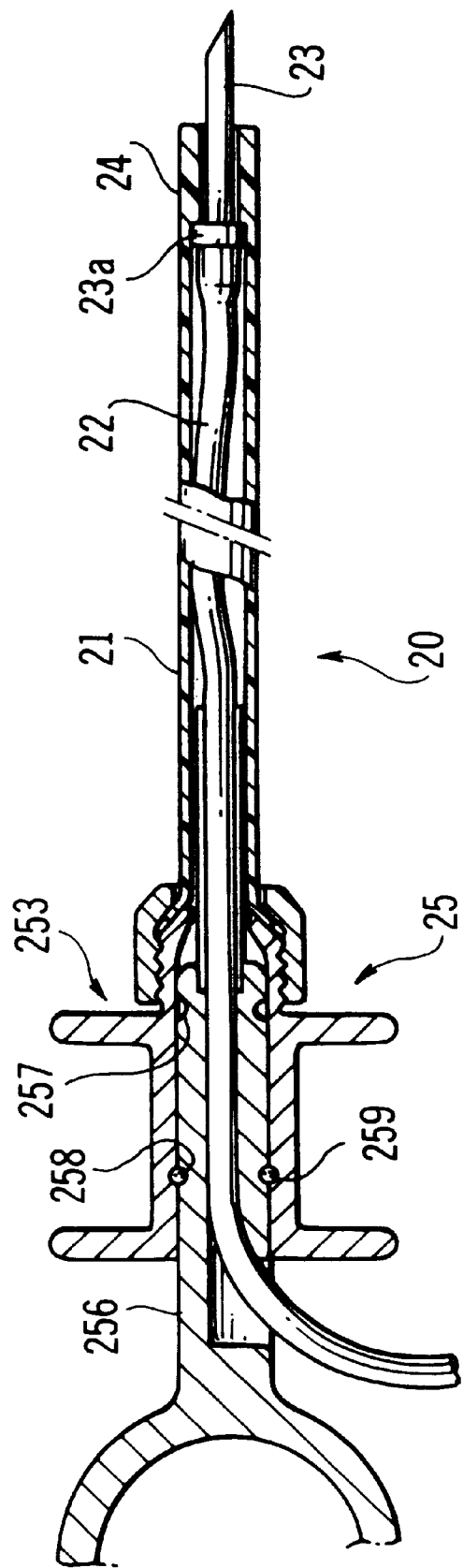
FIG. 50 is a sectional side view of the injector instrument of FIG. 49 when a needle is extended.

On an inner surface of the tip of the cover tube 21, a stopper 24 for restricting the needle 23 from extending more than a predetermined amount is provided. When a flange portion 23a, which is formed at the proximal end side of the needle 23, contacts the stopper as shown in FIG. 50, the needle 23 extends from the end of the cover tube 21 by a predetermined amount and is prevented from extending any further. The amount of movement of the needle 23 is referred to as the needle stroke L5.

As shown in FIG. 49, the injector instrument 20 also includes a manipulation portion 25 for sliding the inner tube 22 along its axis. The manipulation portion 25 is provided with a main body 253 having a pair of flange members 251, which define a first finger hook 252. The proximal end of the cover tube 21 is connected to the main body 253 by a pressure nut 254.

The main body 253 is formed to have a cylindrical hollow portion in which a slider 256 is slidably fitted. At the proximal end of the slider 256, a second finger hook 255 is formed.

The outer surface of the inner tube 22 is fixed to the slider 256. Inside the main body 253, a strengthening pipe 26 is provided. The strengthening pipe 26 surrounds the inner tube 22 and an end of the strengthening pipe 26 is fixedly connected to the slider 256 while the other end is partially inserted in the cover tube 21.

On the outer surface of the slider 256, a pair of circumferential grooves 257 and 258 are formed. The distance between the grooves 257 and 258 along the axis of the slider 256 is defined as the slider stroke L6. On the inner surface of the main body 253, an O-ring 259, which is to engage with one of the grooves 257 and 258, is provided.

By operating the slider 256 to slide with respect to the main body 253, when the O-ring 259 engages with either the groove 257 or 258, the slider 256 is temporarily fixed with respect to the main body 253 with a certain force.

In other words, the slider 256 moves within a range between a position where the O-ring 259 engages with the groove 257 and another position where the O-ring 259 engages with the groove 258 throughout the slider stroke L6.

The slider stroke L6 is set greater than the needle stroke L5. Accordingly, when the slider 256 is inserted into the main body 253, the flange portion 23a contacts the stopper 24 before the O-ring 259 engages with the groove 258. Therefore, even if the cover tube 21 is bent when the needle 23 is to be stuck in (see FIG. 50), the needle 23 is securely extended a predetermined length from the end of the cover tube 21. Further, since the needle 23 is slightly biased to extend straight by the inner tube 22, the needle 23 is securely inserted in the affected part A.

The proximal end portion of the inner tube 22 extends from the slider 256. At the proximal end of the inner tube 22, an injector receiving mouth piece 27 is attached. By coupling an injector 28 to the mouth piece 27, and injecting medical fluid into the inner tube 22, the medical fluid is injected through the needle 23.

Figure 51:
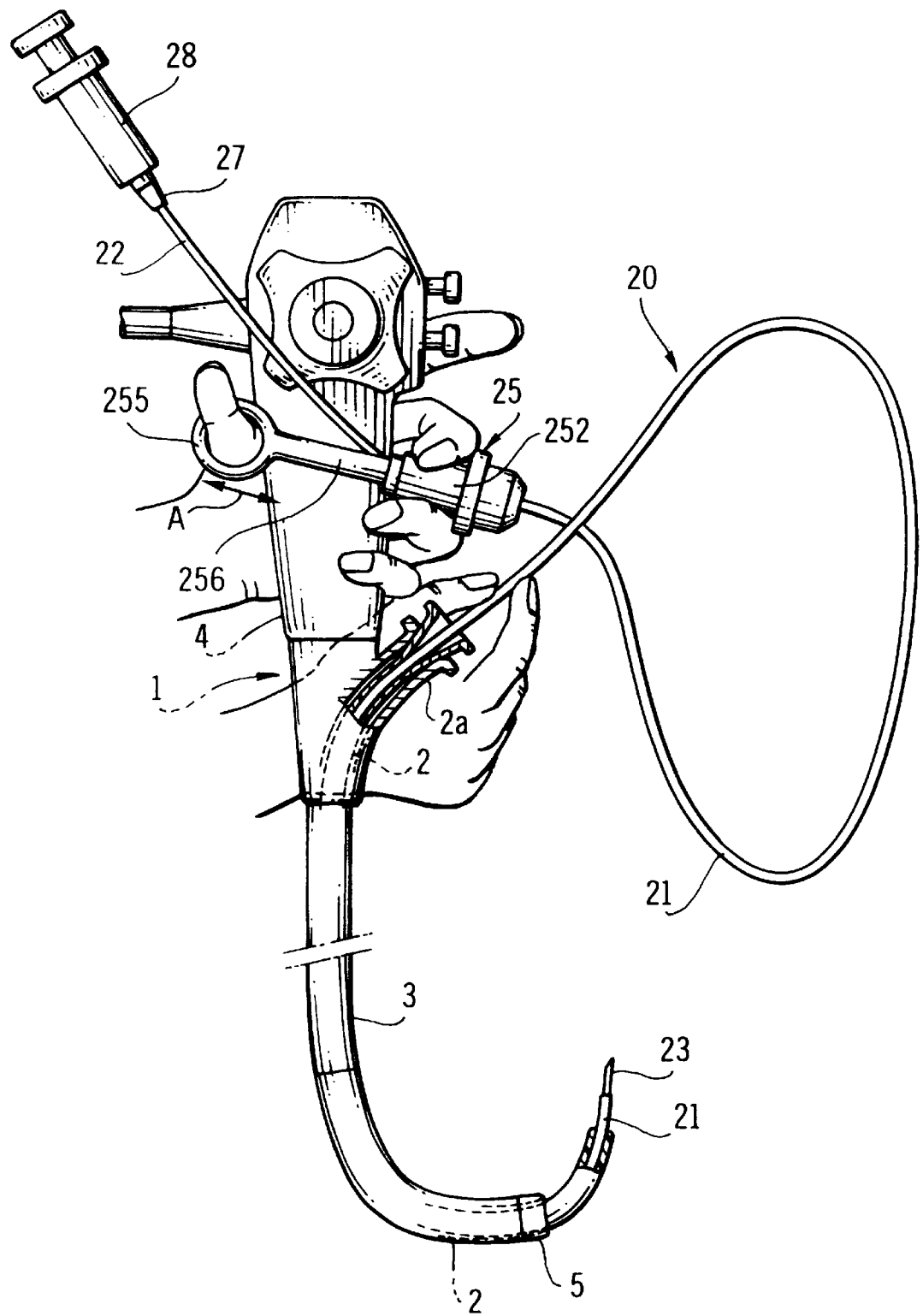
FIG. 51 is a schematic view illustrating the operation of the injector instrument of FIG. 49 in the endoscope.

FIG. 51 shows an example where the injector instrument 20 is inserted in an endoscope 1. In this example, a guide tube is inserted in the forceps channel 2 of the endoscope 1, and the injector instrument 20 is inserted in the guide tube. The endoscope 1 is provided with the insertion portion (bendable portion) 3, the manipulation portion 4, and a tip 5 in which an objective, optical system is accommodated.

As shown in FIG. 51, the manipulation portion 4 is grasped by, for example, a left hand of an operator. While grasping the manipulation portion 4, the manipulation portion 25 of the injedtor instrument 20 can also be held. With a finger and thumb hooked on the first and second finger hooks 252 and 255 respectively, the slider 256 can be moved in the direction indicated by an arrow "A" in FIG. 51 so that the needle 23 is extended from or retracted inside the cover tube 21.

Further, the cover tube 21 can be moved in relation to the endoscope 1 with, in this example, a right hand as shown in FIG. 51. Accordingly, when the injector instrument 20 according to the embodiment is used, an assistant is required only to operate the injector 28 to inject the medical fluid.

Specifically, when the injector instrument 20 is used, the operator first grasps the manipulation portion 4 of the endoscope 1 with one hand (in this example, the left hand) and inserts the injector instrument 20 into the guide tube with the other hand (in this example, the right hand). During this stage, the needle 23 is retracted inside the cover tube 21.

Figure 52:
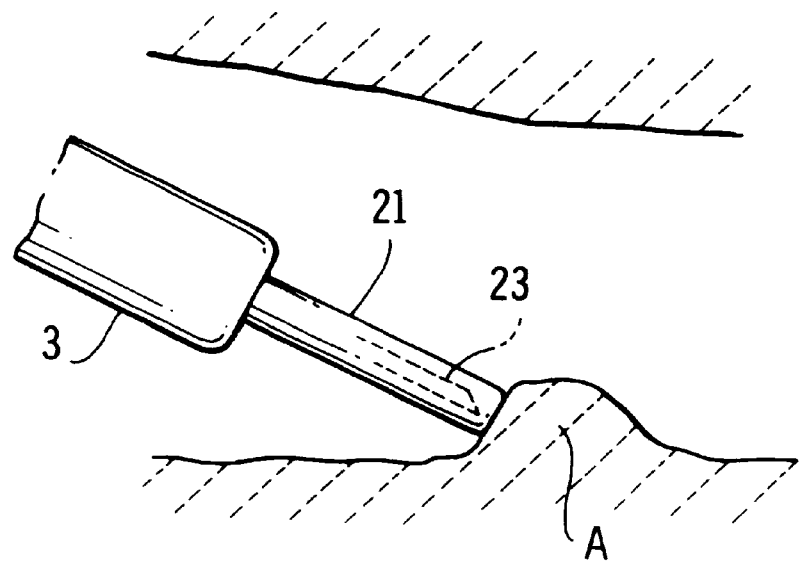
FIG. 52 is a schematic view illustrating press contacting the injector instrument of FIG. 49 on an affected part.

Thereafter, when the tip end of the injector instrument 20 enters an observing area at the distal tip of the endoscope 1, the cover tube 21 is press contacted onto the affected part A as shown in FIG. 52 using the right hand.

Figure 53:
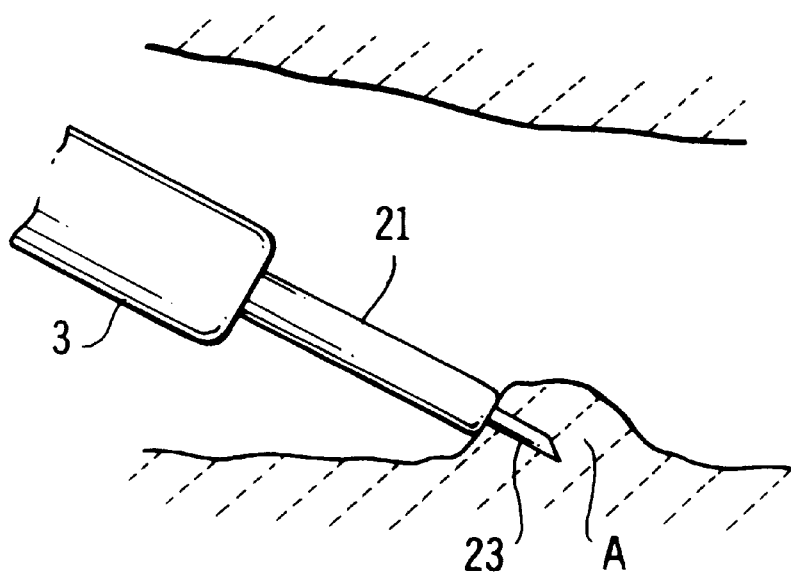
FIG. 53 is a schematic view illustrating the use of the injector instrument of FIG. 49 on the affected part.

Then, as shown in FIG. 53, the needle 23 is extended from the cover tube 21 to stick in the affected part A by operating the manipulation portion 25 of the injector instrument 20 with the left hand.

Thus, the operator is able to perform the series of operations individually. When the needle 23 has been inserted in the affected part A, the assistant operates the injector 28 to supply medical fluid in accordance with the instructions of the operator.

After injecting the medical fluid into the affected part A is completed, the operator retracts the needle 23 inside the cover tube 21 with the left hand, and then removes the injector instrument 20 from the endoscope 1 (i.e., from the forceps channel 3) with the right hand, or alternatively, the removal of the injector instrument 20 may be done by the assistant.

Figure 54:
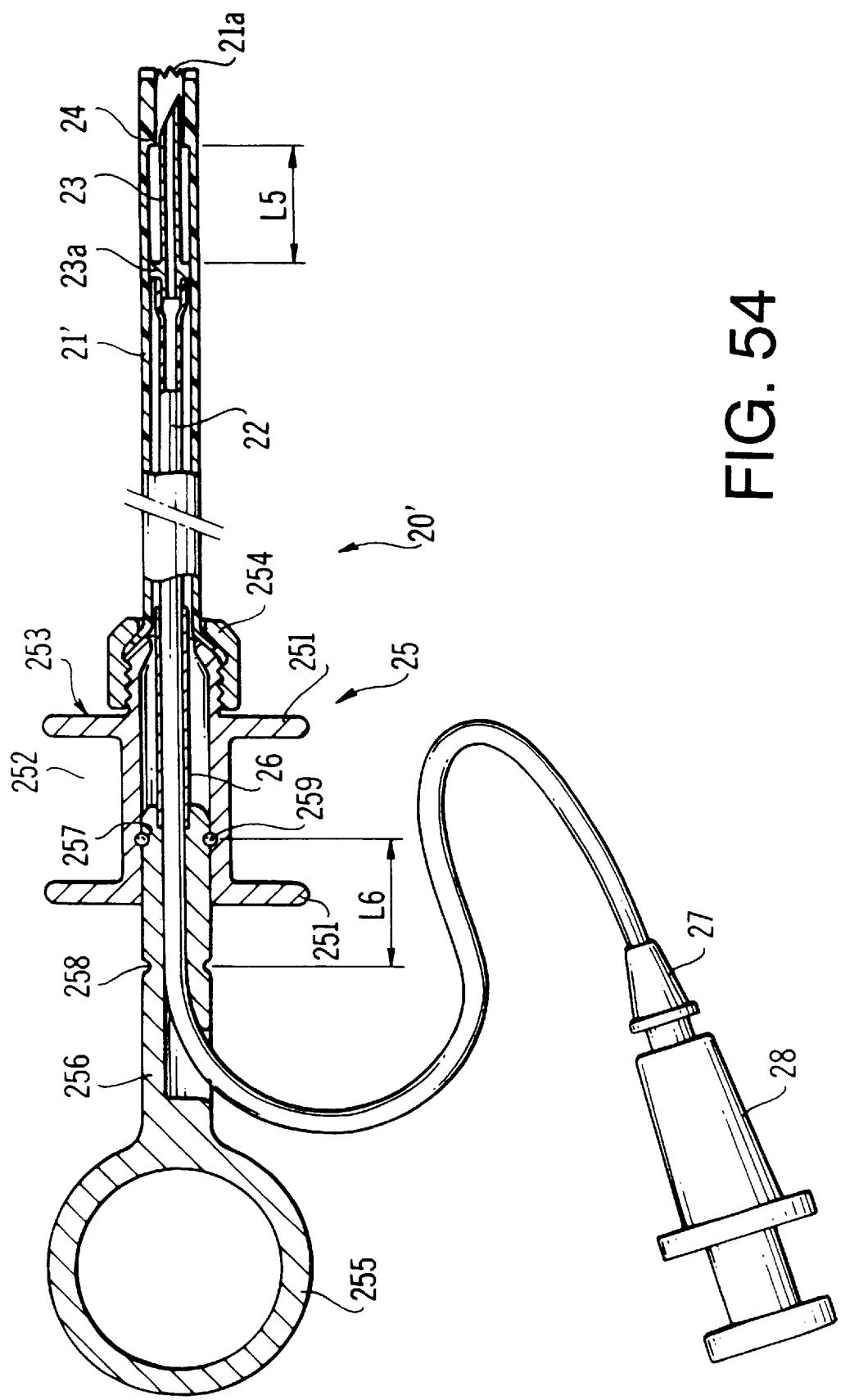
FIG. 54 is a sectional side view of a modification of the injector instrument of FIG. 49.

FIG. 54 shows an injector instrument 20' that is a modification of the injector instrument 20. In the injector instrument 20', the distal end 21a of a cover tube 21' is formed to have a saw-tooth shape so that the distal end 21a of the cover tube 21' digs into the affected part A firmly when the cover tube 21' is press contacted thereto.

Figure 55:
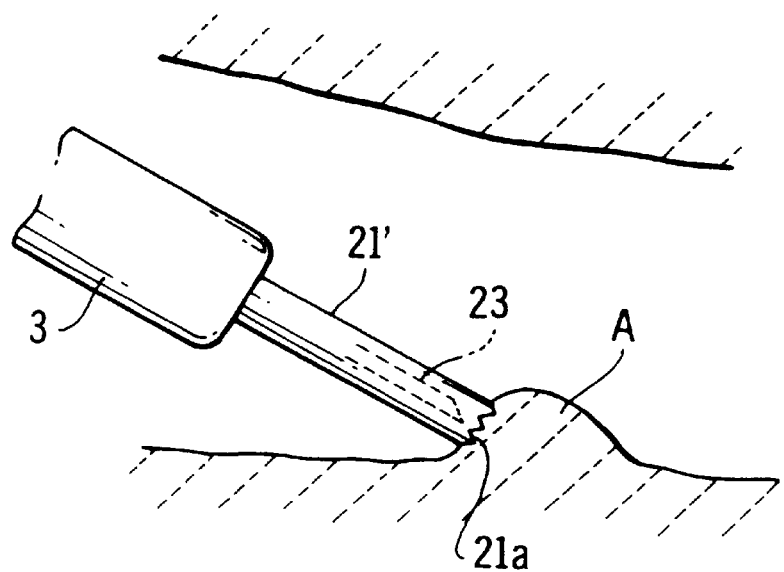
FIG. 55 is a schematic view illustrating press contacting the injector instrument of FIG. 54 on an affected part.
Figure 56:
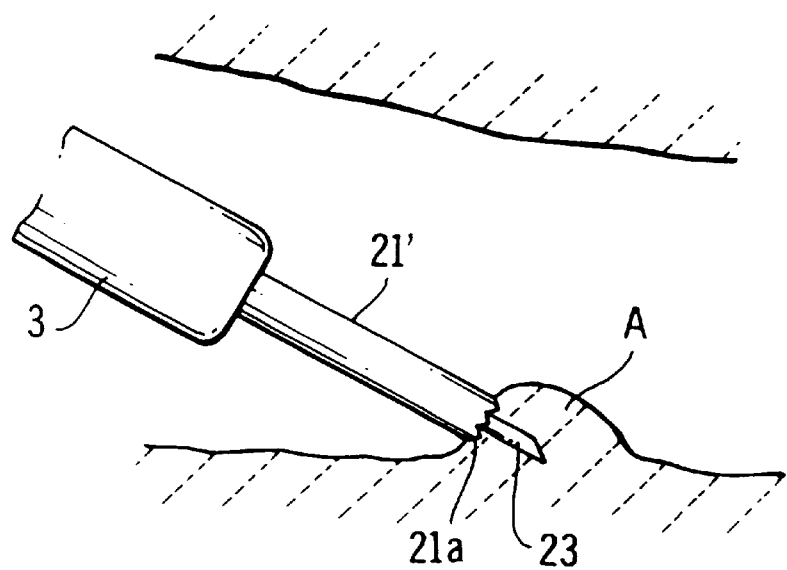
FIG. 56 is a schematic view illustrating the use of the injector instrument of FIG. 54 on the affected part.

With this structure, when the distal end 21a of the cover tube 21' is pressed against the affected part A (as shown in FIG. 55) and the needle 23 is extended from the cover tube 21' (as shown in FIG. 56), the cover tube 21' does not slip on the surface of the affected part A, and the needle 23 is inserted into the desired portion accurately.

Figure 57:
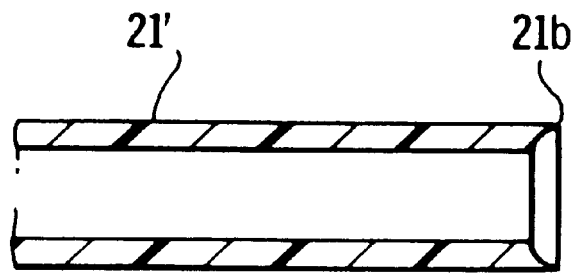
FIG. 57 is a sectional side view of a distal end of a variation of a cover tube of the injector instrument of FIG. 54.
Figure 58:
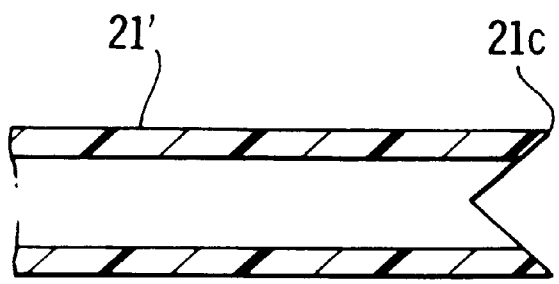
FIG. 58 is a sectional side view of a distal end of another variation of a cover tube of the injector instrument of FIG. 54.
Figure 59:
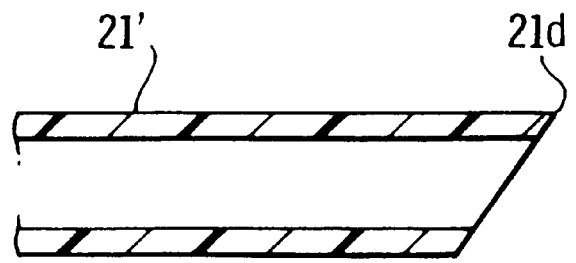
FIG. 59 is a sectional side view of a distal end of yet another variation of a cover tube of the injector instrument of FIG. 54.

It should be noted that the distal end 21a of the cover tube 21' may alternatively be formed to have a ring shaped blade 21b as shown in FIG. 57, a V-cut 21c as shown in FIG. 58, or may be obliquely cut 21d as shown in FIG. 59.

Figure 60:
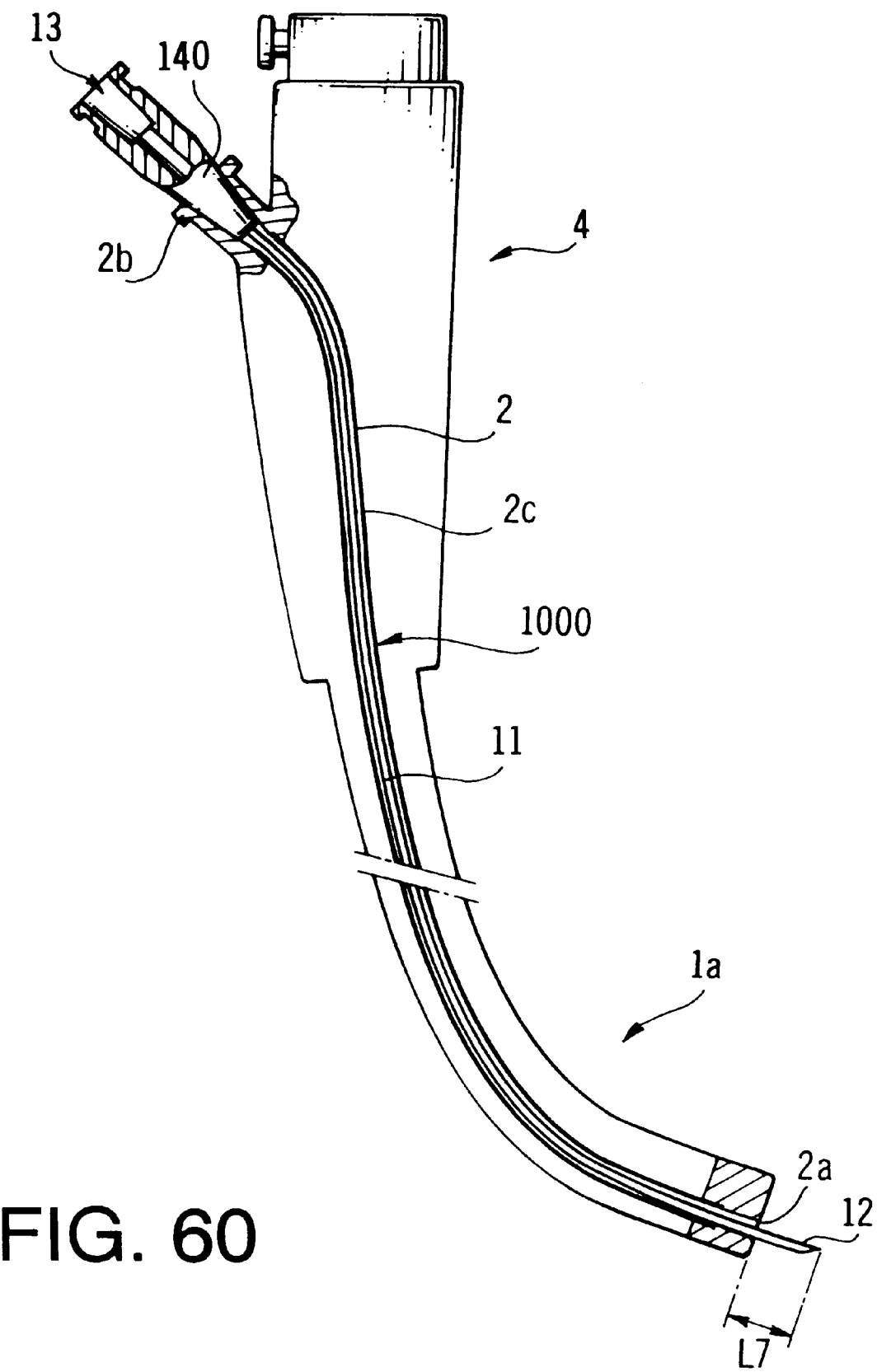
FIG. 60 is a sectional side view of an injector instrument according to a twelfth embodiment of the invention inserted in the forceps channel of the endoscope.

FIG. 60 shows the endoscope 1 and an injector instrument 1000 according to a twelfth embodiment. The injector instrument 1000 is similar to the injector instrument 10 of the first embodiment and common elements are assigned common reference numbers. The endoscope 1 includes the forceps channel 2 in which the injector instrument 1000 is inserted.

The forceps channel 2 is formed such that an opening 2a is provided at the distal end of an insertion portion 1a of the endoscope 1, and a mouth opening 2b is formed at an angle on a manipulation portion 4 of the endoscope 1 at the proximal side end of the forceps channel 2. An inner surface of the mouth opening 2b is formed as a tapered hole having a smaller diameter within the forceps channel 2.

The opening 2a and the mouth opening 2b are connected by a channel 2c, which is a flexible tube made of, for example, a synthetic resin such as polytetra-fluoroethylene resin (PTFE).

The injector instrument 1000 is made of a flexible tube having a predetermined elasticity for example, a synthetic resin such as polyimide resin, PTFE resin, or the like. The injector instrument includes the fluid tube 11 and the needle portion 12. The fluid tube 11 is slidably and removably inserted in the forceps channel 2.

The needle portion 12 is formed at the distal end of the fluid tube 11, for example, by cutting the tip of the fluid tube 11 obliquely. The injector instrument further includes a fluid injector 13 connected at the proximal end of the fluid tube 11.

In this embodiment, a fixing tube 140 is formed unitary with the fluid injector 13. The outer surface of the fixing tube 140 is formed to fit in the mouth opening 2b.

The fixing tube 140 is temporarily fixed onto the mouth opening 2b by applying force when inserting the fixing tube 140 in the mouth opening 2b. Under this condition, the needle portion 12 is projected from the opening 2a of the forceps channel 2 by a predetermined length L7. The fixing tube 140 can be removed from the mouth opening 2b by pulling with sufficient force.

As an example, the length L7 may be approximately 2 to 20 mm. The length may be varied depending on the purpose of the injector instrument 1000. For example, if the injector instrument 1000 is used for a liver or pancreas, the length L7 may be set to approximately 40 mm.

It should be noted that the engagement of the fixing tube 140 with the mouth opening 2b is not limited to the above-described structure. As long as the fixing tube 140 is freely engageable and disengageable with the mouth opening 2b, any structure may be employed. For example, a Luer-Lok type mouth piece may be used.

As described above, when the fixing tube 140 is fitted in the mouth opening 2b, the needle portion 12 protrudes from the opening 2a by the length L7. In use, while observing the affected part through the endoscope 1, the needle portion 12 is inserted in the affected portion A. Then, a medical fluid is injected from a fluid container (not shown) which is connected to the fluid injector 13. Alternatively, material may be collected from the affected area as in a suction biopsy.

Since the injector instrument 1000 does not have a cover tube, or a sheath, the outer diameter of the injector instrument 1000 can be reduced while maintaining the inner diameter at a level that a sufficient amount of fluid can be supplied therethrough. Accordingly, even if the endoscope 1 has a thin insertion portion 1a, i.e., a thin forceps channel 2, the injector instrument 1000 can be inserted, and a sufficient amount of medical fluid can be supplied to the affected part A.

After treatment with use of the injector instrument 1000 is completed, the fixing tube 140 is removed from the mouth opening 2b and the injector instrument 1000 is pulled out of the forceps channel 2. Then, after the treated portion is observed, the endoscope 1 is removed from the human cavity.

Figure 61:
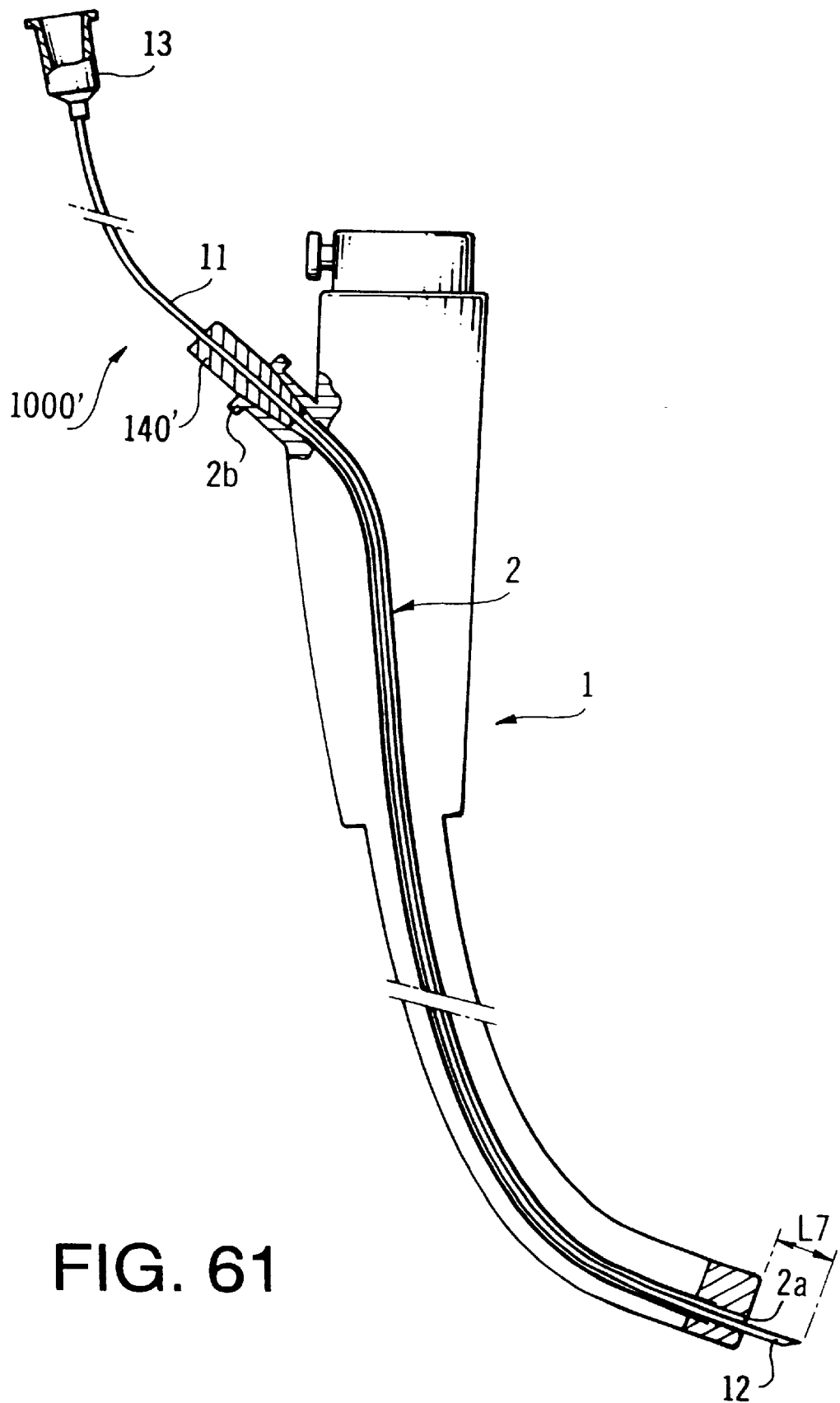
FIG. 61 is a sectional side view of a modification to the injector instrument of FIG. 60 inserted in the forceps channel of the endoscope.

FIG. 61 shows a variation of the twelfth embodiment in which the fluid tube 11 is made longer such that the fluid tube 11 extends beyond a fixing tube 140', and the fluid injecting portion 13 is fixed onto the proximal end of the fluid tube 11 apart from the fixing tube 140'. This structure is advantageous in that the medical fluid can more conveniently be supplied from the injecting portion 13.

As described above, the position of the fluid tube 11 where the fixing tube 140' is fixed is determined such that when the fixing tube 140' is coupled to the mouth opening 2b, the needle portion 12 protrudes from the opening 2a by a length L7.

Figure 62:
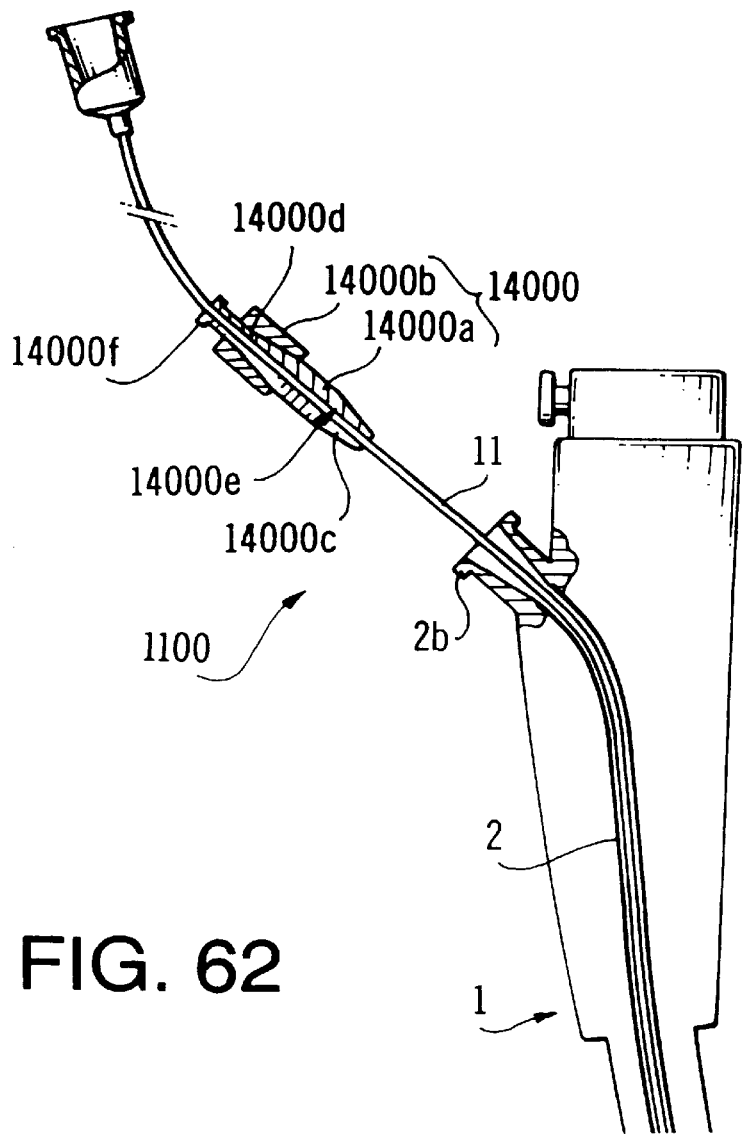
FIG. 62 is a sectional side view of an injector instrument according to a thirteenth embodiment of the invention inserted in the forceps channel of the endoscope.

FIG. 62 shows an injector instrument 1100 according to a thirteenth embodiment of the invention. The injector instrument 1100 is similar to the injector instrument of the twelfth embodiment, however, instead of the fixing tube 140, there is provided a fixing tube 14000 that includes a slidable tube 14000a having a through opening, fitted on the outer surface of the fluid tube 11, and a tapered tube 1400b used for fixing the slidable tube 14000a at a variable position on the fluid tube 11.

Figure 63:
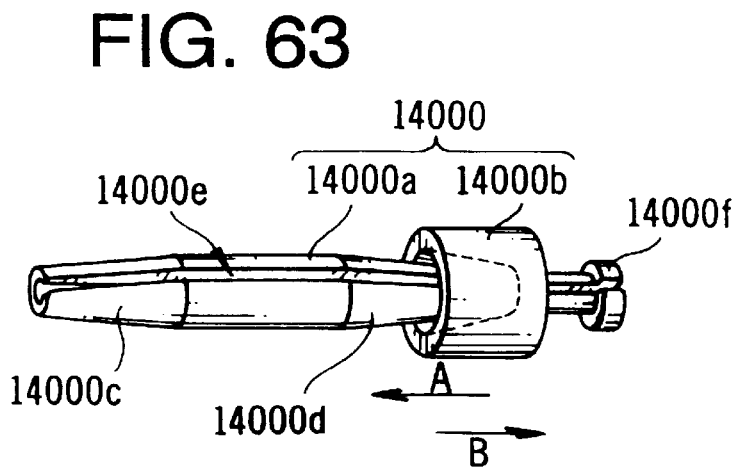
FIG. 63 is a perspective view of a fixing tube of the injector instrument of FIG. 62.

FIG. 63 shows an enlarged view of the fixing tube 14000. On the outer surface of the slidable tube 14000a, at one end thereof, a tapered surface 14000c which fits in the mouth opening 2b is formed. The other end of the slidable tube 14000a has another tapered surface 14000d which is tapered in the opposite direction. A slit 14000e is formed parallel to the axis of and through the whole length of the slidable tube 14000a. The tapered tube 14000b is fitted on the tapered surface 14000d. A stopper portion 14000f is formed at the end of the slidable tube 14000a to prevent the tapered tube 14000b from falling off.

If the tapered tube 14000b is slid in the direction "A", the slidable tube 14000a deforms in the direction where the width of the slit 14000e is reduced. Then, the inner surface of the slidable tube 14a press contacts the outer surface of the fluid tube 11, and thus the fixing tube 14000 is fixed in position on the fluid tube 11.

If the tapered tube 14000b is slid in the direction "B", the slidable tube 14000a returns its neutral shape, and accordingly the fixing tube 14000 can slide relative to the fluid tube 11. Therefore, according to the thirteenth embodiment, the position of the fixing tube 14000 can be set arbitrarily, and the projected length L7 of the needle portion 12 can be adjusted to a desired length.

According to the twelfth and thirteenth embodiments, the injector instrument 1000, 1100 can be used for an endoscope 1 having a relatively thin forceps channel, and a sufficient amount of fluid can be injected. Further, the amount of the needle portion 12 stuck in the affected part A can be adjusted accurately.

Figure 64:
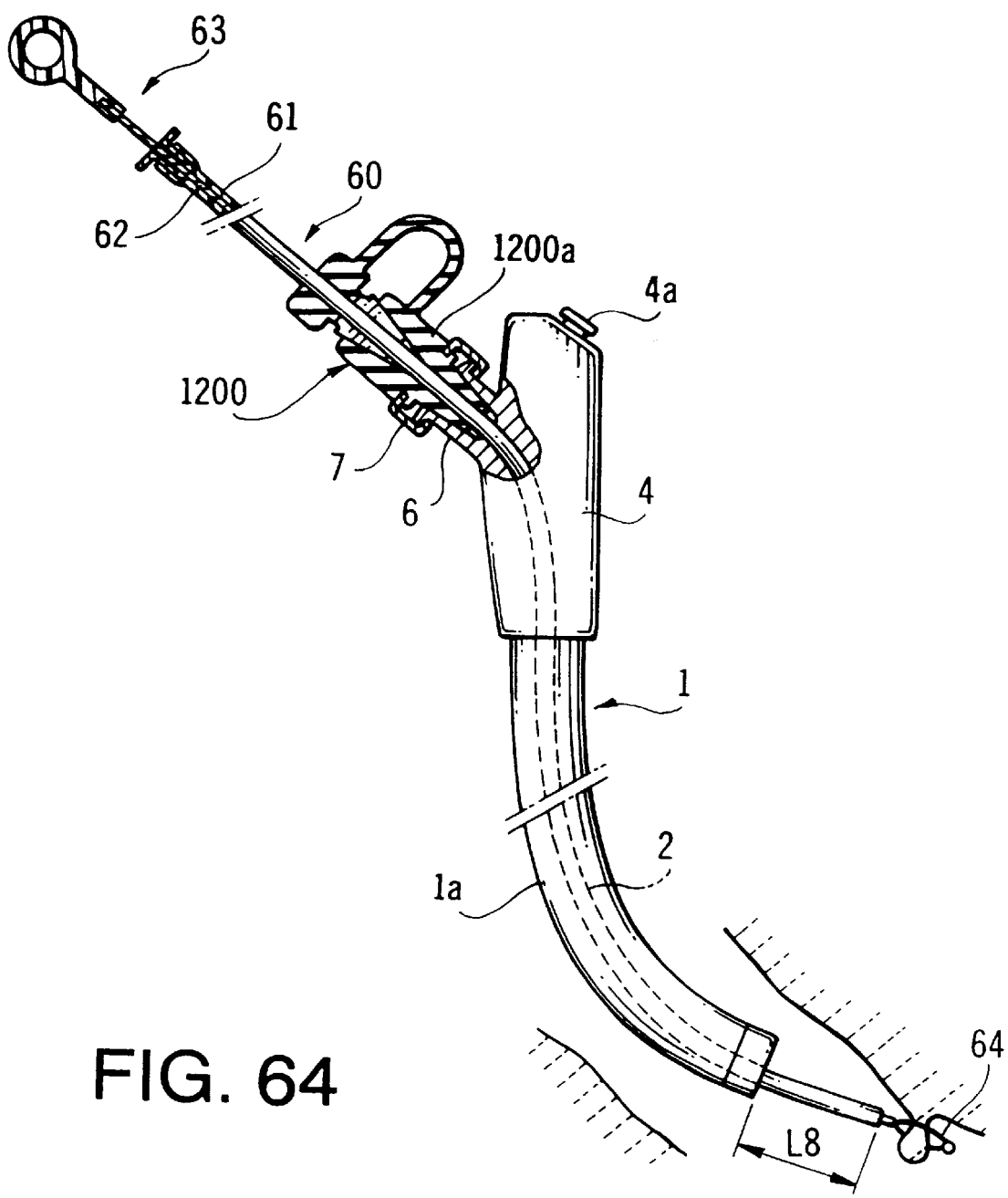
FIG. 64 is a sectional side view of a treatment accessory fixing device according to a fourteenth embodiment of the invention fixing a treatment device in the forceps channel of the endoscope.

FIG. 64 shows a treatment accessory fixing device 1200 according to a fourteenth embodiment of the invention provided on the endoscope 1. The treatment accessory fixing device 1200 fixes a treatment accessory 60 inserted in the endoscope 1.

The endoscope 1 is provided with the flexible insertion portion 1a and the manipulation portion 4 which is connected at the proximal end of the insertion portion 1a. Through the entire length of the insertion portion 1a, the forceps channel 2 is formed having an exit opening at the distal end surface of the insertion portion 1a and an insertion opening on an oblique upper surface of the manipulation portion 4. The manipulation portion 4 is also provided with a water/air supply/suction button 4a.

In FIG. 64, the treatment accessory 60 is a snare instrument for cutting polyps or the like, although other treatment accessories may be used accordingly. The treatment accessory 60 has a flexible cover tube 61, and an operation wire 62 slidably inserted in the cover tube 61. An end of the wire 62 is connected to a snare loop 64, and the other end of the wire 62 is connected to a snare operation portion 63. By moving the snare operating portion 63, the snare loop 64 can be loosened or tightened.

A mouth piece 6 provided at the insertion opening of the forceps channel 2 has a similar shape to the mouth piece 2b of the ninth twelfth embodiments (for example, a Lure-Loc type), and the inner surface of the mouth piece 6 is tapered.

A base portion 1200a of the fixing device 1200 is formed as a tapered tube which fits in the tapered opening of the mouth piece 6. Thus, positioning of the fixing device 1200 is done by inserting the base portion 1200a into the tapered opening of the mouth piece 6. In this embodiment, in order to fix the position of the fixing device 1200 securely, a Lure-Loc fastening ring 7 is provided to fit around the mouth piece 6. The fastening ring 7 may be omitted if the fixing device 1200 is otherwise fixedly positioned without such a fastening ring 7.

Figure 65:
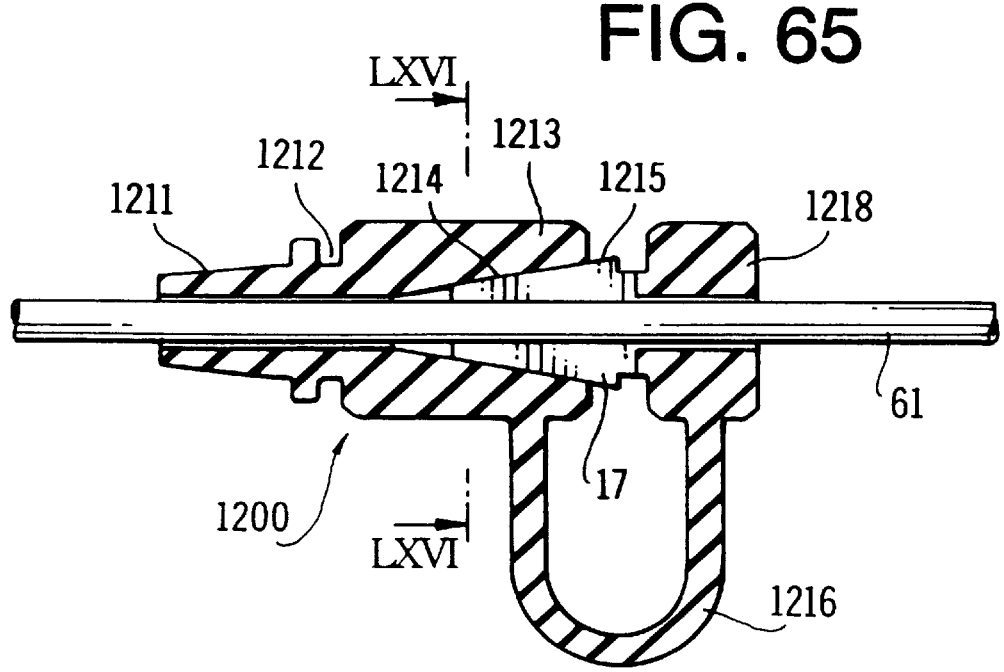
FIG. 65 is a sectional side view of the treatment accessory fixing device of FIG. 64.

FIG. 65 shows an enlarged sectional view of the fixing device 1200. The fixing device 1200 is made of a flexible material such as nylon, propylene, or the like, and preferably made unitarily. An end of the fixing device 1200 is formed to be a tapered tube 1211, and next to the tapered tube portion 1211, a ring-groove 1212 to be engaged with the Lure-Loc fastening ring 7 is formed. Next to the ring-groove 1212, a receiving portion 1213 is provided. A tapered opening 1214 is formed inside the receiving portion 1213. Further, the fixing device 1200 is provided with a plug-in portion 1215, which is detachably inserted in the tapered opening 1214.

A grasping portion 1218 is connected to the plug-in portion 1215. The grasping portion 1218 and the receiving portion 1213 are connected with a flexible connecting belt 1216.

The axis of the tapered opening 1214 coincides with the axis of the forceps channel 2 when the fixing device 1200 is coupled to the mouth piece 6.

At the center of the plug-in portion 1215, a through hole is formed where the cover tube 61 is inserted. The size of the through hole is determined such that the diameter of the through hole is substantially the same as the outer diameter of the cover tube 61, and such that the cover tube 61 is not squeezed by the through hole. The outer surface of the plug-in portion 1215 is tapered such that the plug-in portion 1215 can be firmly inserted in the tapered opening 1214 of the receiving portion 1213.

Figure 66:
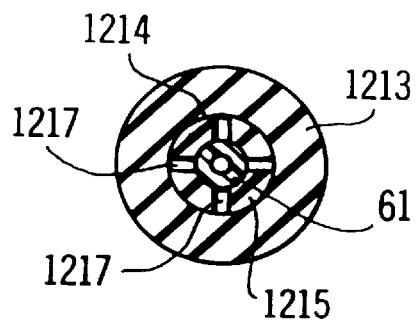
FIG. 66 is a sectional end view of the treatment accessory fixing device of FIG. 64.

FIG. 66 shows a sectional end view of the fixing device 1200. As shown in FIG. 66, on the plug-in portion 1215, crossed slots 1217 are formed inside the plug-in portion 1215. Note that the slots are formed only on the plug-in portion 1215, and no slots are formed on the grasping portion 1218.

Accordingly, if the plug-in portion 1215 is not plugged in or is only loosely inserted in the tapered opening 1214, the fixing device 1200 can be moved freely along its axis relative to the cover tube 61 of the treatment accessory 60.

When an operator grasps the grasping portion 1218 and pushes, inserting the plug-in portion 1215 in the tapered opening 1214 firmly, the pieces (divided by the slots 1217) of the plug-in portion 1215 are pushed towards the axis and therefore are press-contacted with the outer surface of the cover tube 61. Thus the position of the fixing device 1200 with respect to the treatment accessory 60 is fixed.

The positioning of the fixing device 1200 with respect to the treatment accessory 60 (i.e., the cover tube 61) described above is done before the treatment accessory 60 is inserted in the forceps channel 2.

When the treatment accessory 60 is operated, by coupling the fixing device 1200, which is fixed onto the cover tube 61, to the mouth piece 6, the length L8 of the cover tube 61 projected from the insertion portion 1a of the endoscope 1 can be set to a predetermined length, as shown in FIG. 64.

Generally, the length L8 is within a range of 10–40 mm. Since the fixing device 1200 may be positioned at any portion of the treatment accessory, the length L8 can be set accurately for endoscopes having insertion portions 1a having various lengths.

By loosening the engagement of the plug-in portion 1215 with the tapered opening 1214 after the treatment accessory is inserted in the forceps channel 2, the fixing device 1200 can be moved with respect to the cover tube 61. Accordingly, a re-setting of the length L8 can be executed easily.

Figure 67:
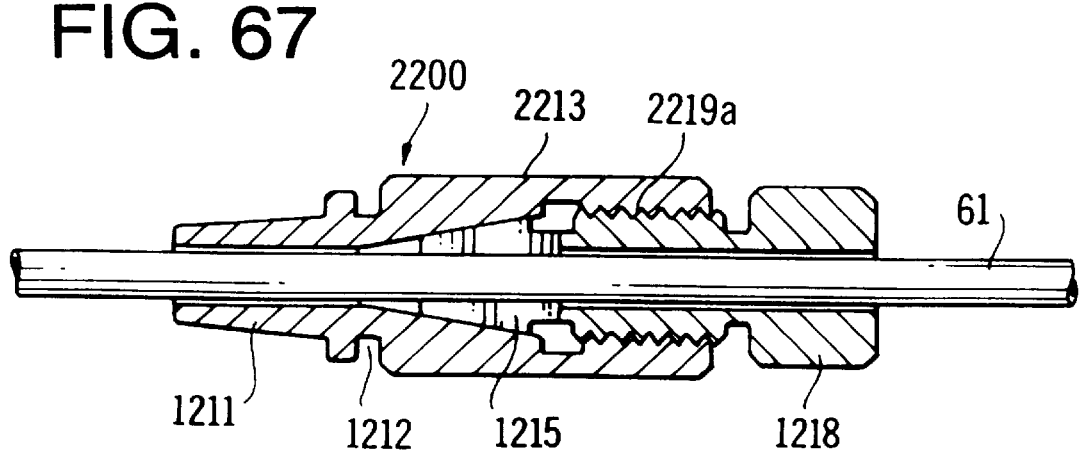
FIG. 67 is a sectional side view of a treatment accessory fixing device according to a fifteenth embodiment of the invention.

FIG. 67 shows a fixing device 2200 according to a fifteenth embodiment. The fixing device 2200 has a similar structure to the fixing device 1200 of the fourteenth embodiment except that the fixing device 2200 does not have the connecting belt 1216 and further a screw thread 2219a is formed on the inner surface of a receiving portion 2213, and further a screw portion 2219b to be engaged with the screw thread 2219a inside the receiving portion 2213 is provided between the plug-in portion 1215 and the grasp portion 1218. With this structure, the fastening and loosening of the plug-in portion 1215 with respect to the receiving portion 2213 can be done more reliably.

Figure 68:
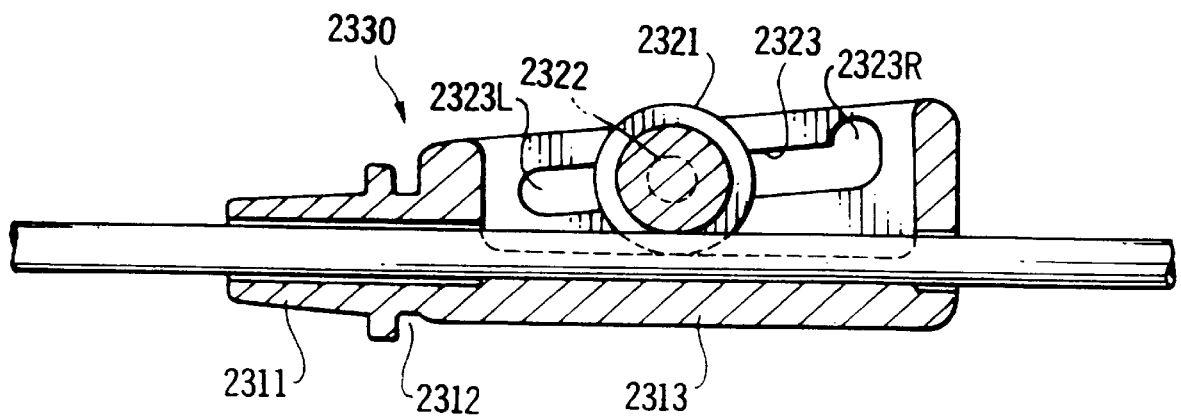
FIG. 68 is a sectional side view of a treatment accessory fixing device according to a sixteenth embodiment of the invention.

FIG. 68 shows a fixing device 2300 according to a sixteenth embodiment. In the fixing device 2300, a roller 2321 for pressing the cover tube 61 is provided. The roller 2321 rotates about a shaft 2322. The shaft 2322 is provided in an L-shaped groove 2323 which is formed obliquely on a receiving portion 2313 of the fixing device 2300.

Figure 69:
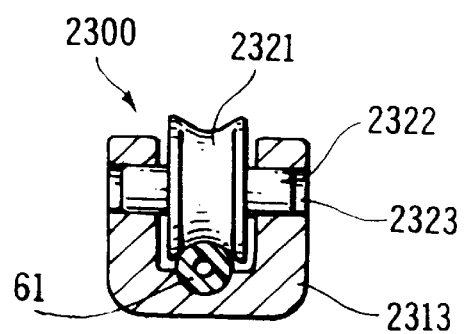
FIG. 69 is a sectional end view of the treatment accessory fixing device of FIG. 68.

The direction where the L-shaped groove 2323 extends is slightly inclined with respect to the axis of the cover tube 61. The inclination angle is approximately 4 or 5 degrees. The circumferential surface of the roller 2321 is formed to be arc shaped in section, as shown in FIG. 69, so that the circumferential surface fits around the cover tube 61.

When the roller 2321 is located at a portion 2323R, the roller 2321 does not press the cover tube 61, and accordingly, the fixing device 2300 can be moved freely with respect to the cover tube 61. If the roller 2321 is located at a portion 2323L, the roller 2321 presses the cover tube 61, and accordingly the fixing device 2300 is fixedly positioned with respect to the cover tube 61.

Figure 70:
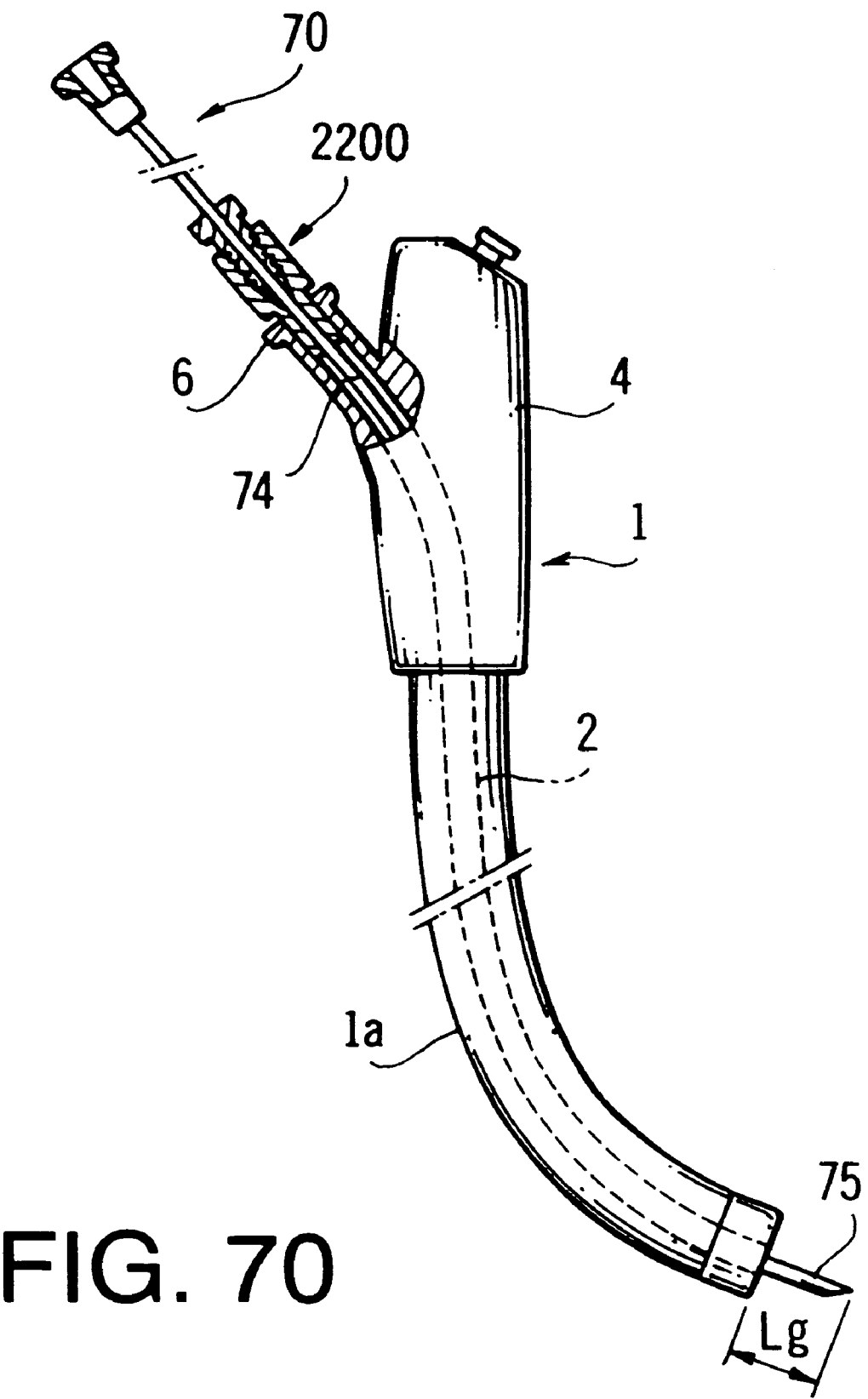
FIG. 70 is a schematic sectional view illustrating the use of the treatment accessory fixing device of FIG. 67.

FIG. 70 shows a schematic side view of an injector instrument 70 being used as a treatment accessory in the endoscope 1. In FIG. 70, the fixing device 2200 according to the fifteenth embodiment is used. It should be noted that, with regard to the arrangement shown in FIG. 70, the fixing device 2200 can be replaced with another embodiment of the fixing device as described above.

The injector instrument 70, similar to the injector instrument 10 of the first embodiment, does not have a cover tube but includes a fluid tube 74 and a needle portion 75 formed at an end thereof. The fluid tube 74 is inserted through the forceps channel 2 of the endoscope 1.

In this case, the fixing device 2200 is fixed on the fluid tube 74. When the fixing device 2200 is coupled to the mouth piece 6, the needle portion 75 is set to extend from the insertion portion 1a of the endoscope 1 by a predetermined length L9. Since the length L9 is reliably set by the use of the fixing device 2200, the needle portion 75 will extend only a desired amount and an injection inside the human cavity can be executed safely and accurately.

Figure 71:
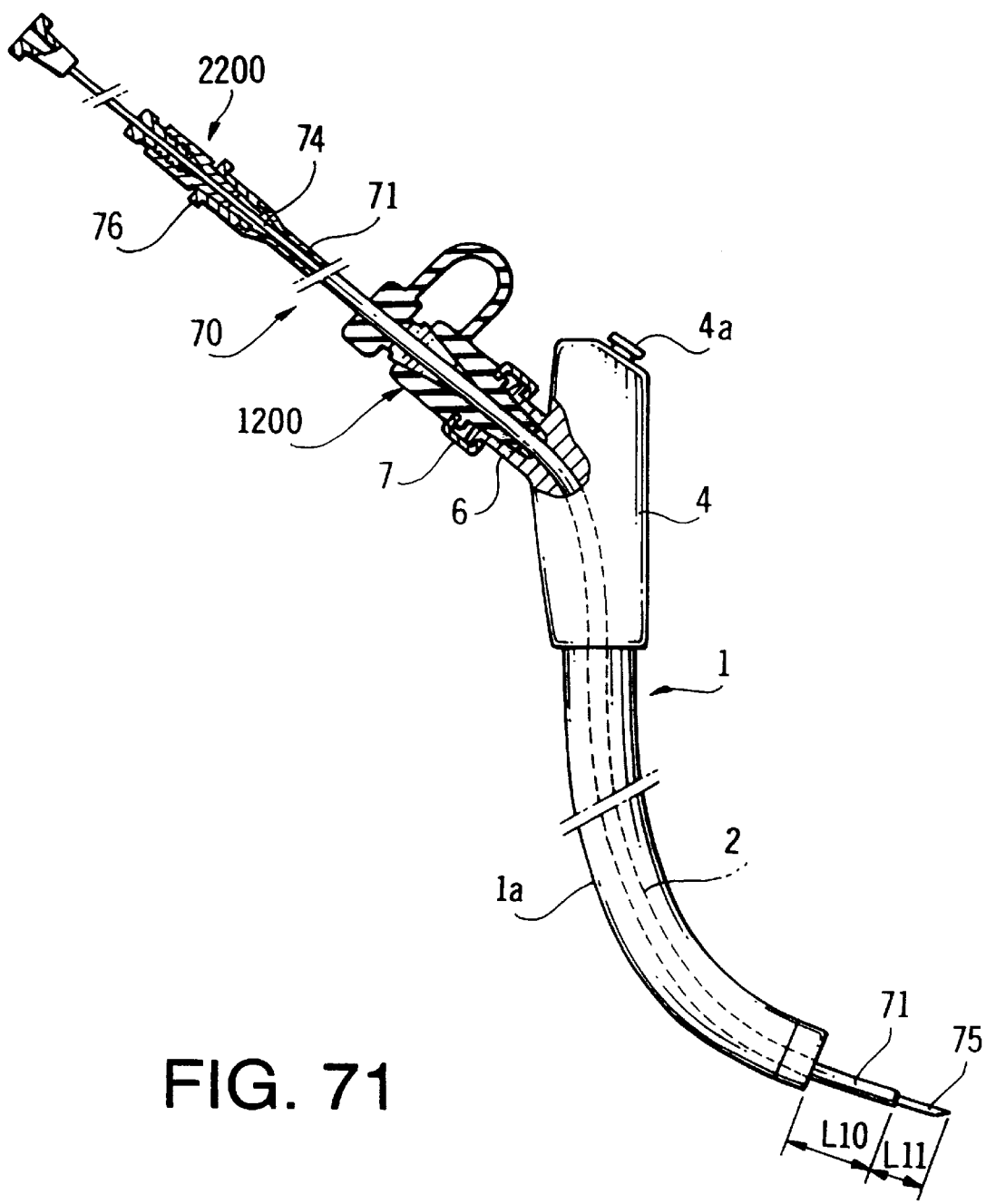
FIG. 71 is a schematic sectional view illustrating the use of both the treatment accessory fixing device of FIG. 67 and the treatment accessory fixing device of FIG. 64.

FIG. 71 shows another example when the injector instrument 70 is used as the treatment accessory.

The injector instrument 70 in this example is provided with a cover tube 71, the fluid tube 74, and the needle portion 75. The fluid tube 74 is slidably enclosed inside the cover tube 71.

The fixing device 1200 according to the fourteenth embodiment is attached to the cover tube 71. Accordingly the length L10 of the cover tube 71 that extends from the distal end of the insertion portion 1a of the endoscope 1 is set.

Further, in this example, the fixing device 2200 may be attached at the proximal end of the fluid tube 74 and the cover tube 71 may be provided with a mouth piece 76 such that the fixing device 2200 fits in the mouth piece 76. Accordingly, the length L11 of the needle portion 75 projected from the cover tube 71 can also be adjusted.

According to the fourteenth, fifteenth, and sixteenth embodiments, the fixing device can be fixedly positioned on a desired portion of the treatment accessory, and by fixedly positioning the fixing device onto the endoscope or another portion of the treatment accessory, the amount of a portion of the treatment accessory extending from the insertion portion of the endoscope can be set to a desired length.

Figure 72:
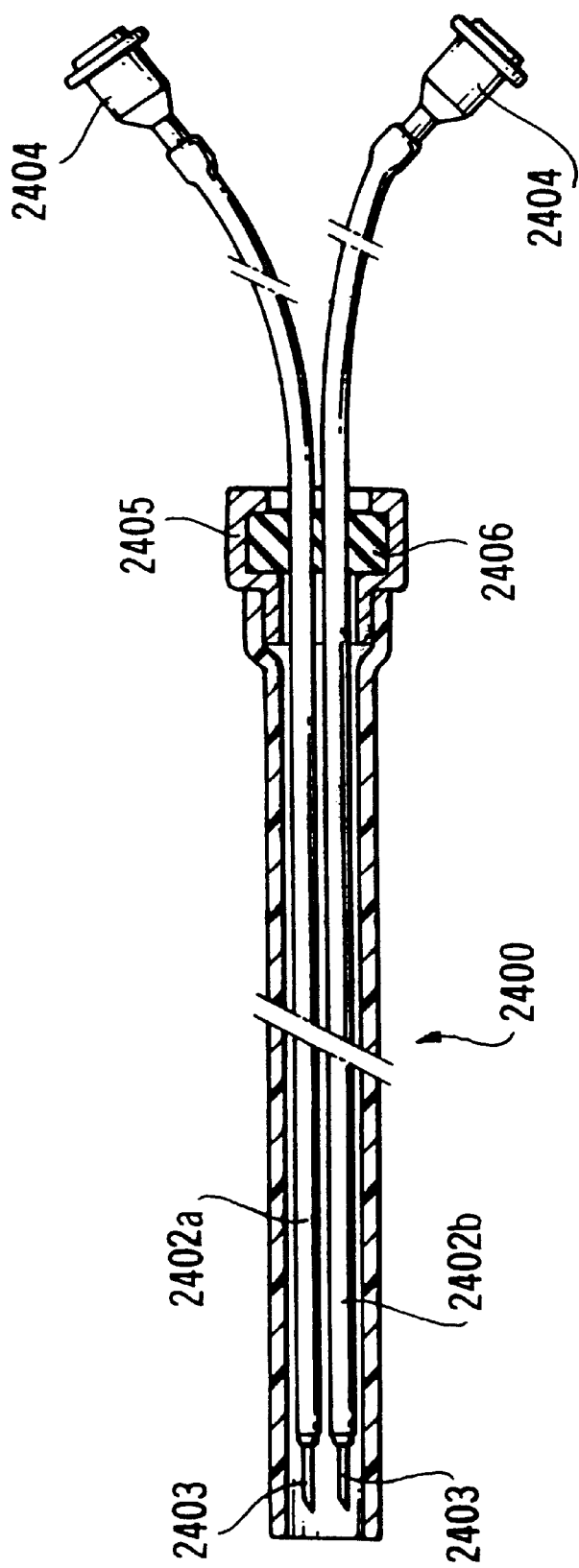
FIG. 72 is a sectional side view of an injector instrument according to a seventeenth embodiment of the invention.

FIG. 72 shows an injector instrument 2400 according to a seventeenth embodiment. The injector instrument 2400 includes a cover tube 2401 which, during use, is slidably and removably inserted in the forceps channel 2 of the endoscope 1 (see FIG. 73). The cover tube 2401 is made of a synthetic resin, such as polytetra-fluoroethylene (PTFE), having a predetermined flexibility.

A pair of fluid supply tubes 2402a and 2402b are inserted through the whole length of the cover tube 2401. The fluid supply tubes 2402a and 2402b are slidable inside the cover tube 2401. Each of the fluid supply tubes 2402a and 2402b is made of a synthetic resin, such as polyimide resin, polyurethane resin, PTFE or the like, also having a predetermined flexibility.

An injection needle 2403 is connected at the distal end of each of the fluid supply tubes 2402a and 2402b. The needle 2403 may be a metal needle, or alternatively, the needle 2403 may be unitarily formed with each of the fluid supply tubes 2402a and 2402b. The type, size, and hardness of the needle 2403 can be determined in accordance with the particular intended purpose of the injector instrument and in accordance with the description above.

The proximal end portion of each of the fluid supply tubes 2402a and 2402b extend from the proximal end of the cover tube 2401 by a predetermined amount, for example, 30 to 50 cm. A mouth piece 2404 is connected to the proximal ends of each of the fluid supply tubes 2402a and 2402b for receiving an injector (not shown).

At the proximal end of the cover tube 2401, an end piece 2405 is fixed. A packing member 2406 is enclosed in the end piece 2405. The packing member 2406 is made of, for example, independent foam sponge or the like, and supports the pair of fluid supply tubes 2402a and 2402b slightly apart from each other. The packing member 2406 prevents backflow from exiting from the proximal end of the cover tube 2401.

Since the pair of fluid supply tubes 2402a and 2402b are supported by the packing member 2406, the fluid supply tubes 2402a and 2402b remain in a fixed position. However, the fluid supply tubes 2402a and 2402b may be pushed or pulled such that the portion of the fluid supply tubes 2402a and 2402b outside the cover tube 2401 changes and accordingly the needle portions 2403 move to be extended from or retracted into the cover tube 2401.

Figure 73:
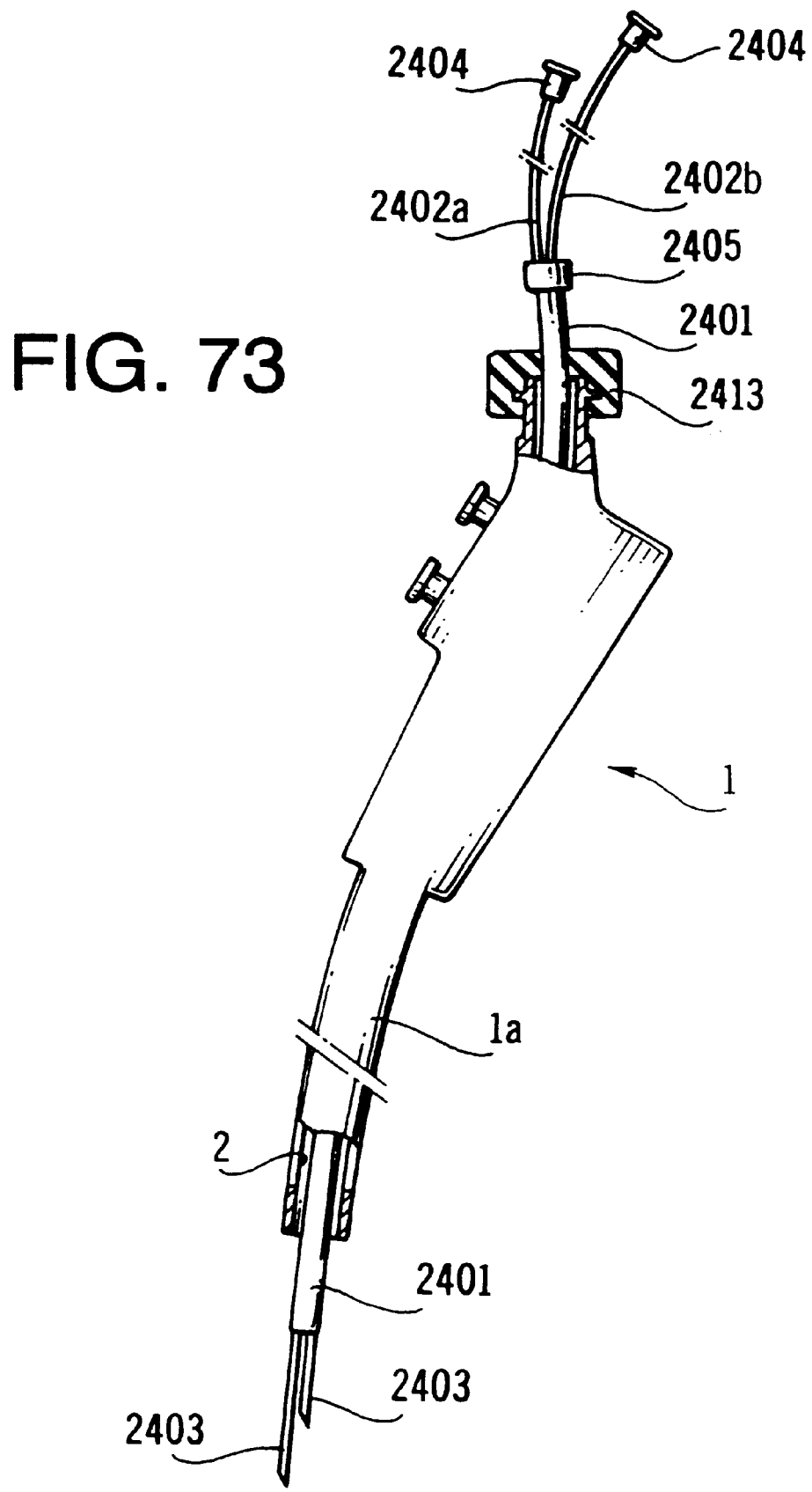
FIG. 73 is a sectional side view of the injector instrument of FIG. 72 inserted in the forceps channel of the endoscope.

As shown in FIG. 73, the endoscope 1 is provided with a forceps tap 2413 at the proximal-end of the forceps channel 2. The forceps tap 2413 holds the injector instrument 2400 in place when the injector instrument 2400 has been fed into the forceps channel 2 of the endoscope 1.

Figure 74:
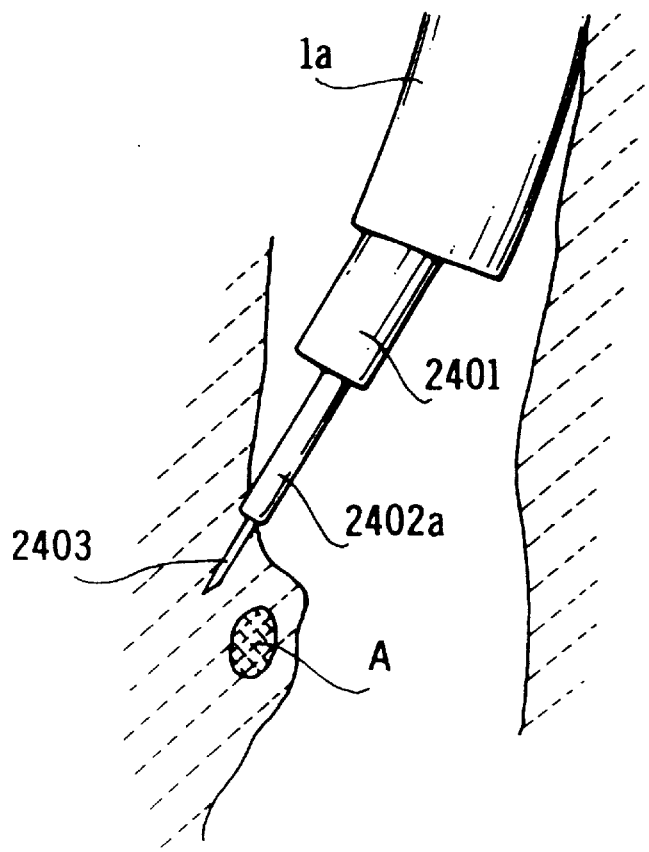
FIG. 74 is a schematic view illustrating the use of the injector instrument of FIG. 72 when a first needle is operated.

FIG. 74 shows a situation where the cover tube 2401 has been inserted through the forceps channel 2 and extended from the insertion portion 1a of the endoscope 1. Further, the first fluid supply tube 2402a has been pushed in the cover tube 2401 such that the needle portion 2403 extends from the cover tube 2401. In FIG. 74, the needle portion 2403 connected to the first fluid supply tube 2402a has missed the affected part A. If a conventional injector were being used it would be necessary to first remove and then re-insert the needle portion 2403 again trying to contact the affected part A.

Figure 75:
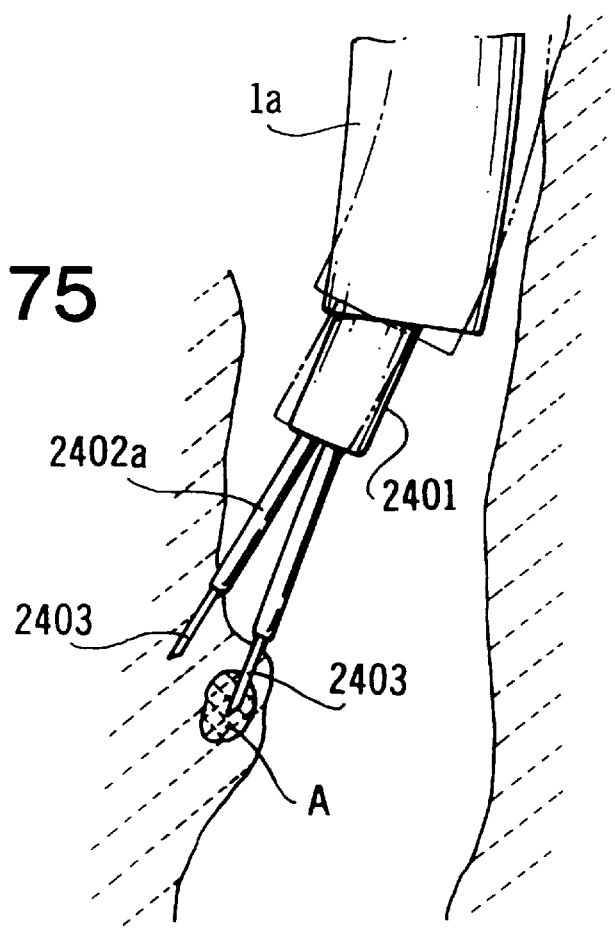
FIG. 75 is a schematic view illustrating the use of the injector instrument of Fig, 72 when a second needle is operated.

However, according to the injector instrument 2400 of the seventeenth embodiment, in such a situation, the second fluid supply tube 2402b is pushed to extend from the cover tube 2401, the orientation of the insertion portion 1a is adjusted, and, as shown in FIG. 75, the needle portion 2403 connected to the second fluid supply tube 2402b is inserted into the affected part A.

According to the seventeenth embodiment, since the first and second fluid supply tubes 2402a and 2402b are flexible, the orientation or attitude of the insertion portion 1a can be changed easily even when one of the needle portions 2403 is inserted into the tissue.

Figure 76:
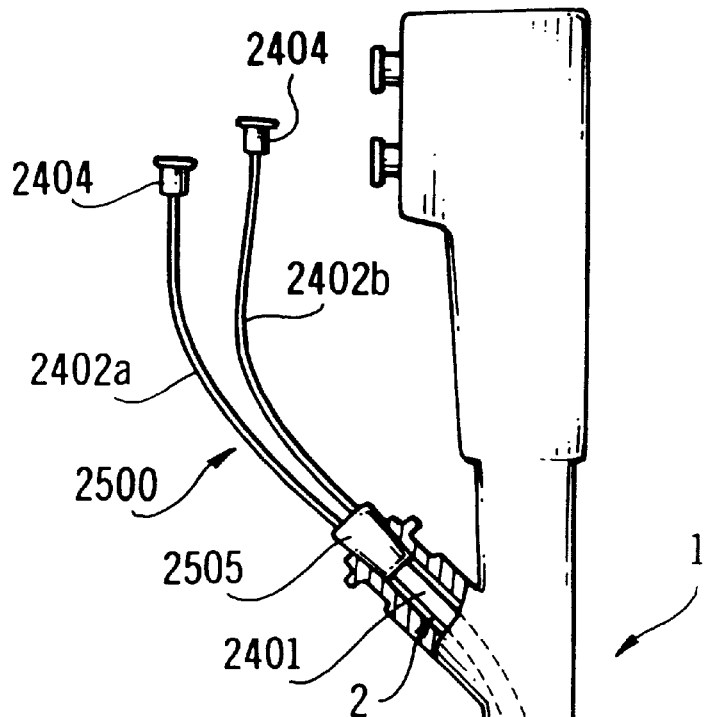
FIG. 76 is a sectional side view of an injector instrument according to an eighteenth embodiment of the invention inserted in the forceps channel of the endoscope.

FIG. 76 shows an injector instrument 2500 according to an eighteenth embodiment inserted in the endoscope 1. In this embodiment, the endoscope 1 is not provided with the forceps tap 2413 as in the description for the previous embodiment. Instead an end piece 2505 of the injector instrument 2500 is formed such that the end piece 2505 may be fixed at the inlet of the forceps channel 2 of the endoscope 1. This structure allows an operator to manipulate both the endoscope 1 and the injector instrument 2500 more easily since the cover tube 2401 is fixed relative to the forceps channel 2. The cover tube 2401 may be designed such that the length L12 that the cover tube 2401 extends from the tip of the insertion portion 1a of the endoscope 1 is set in accordance with a particular purpose.

Figure 77:
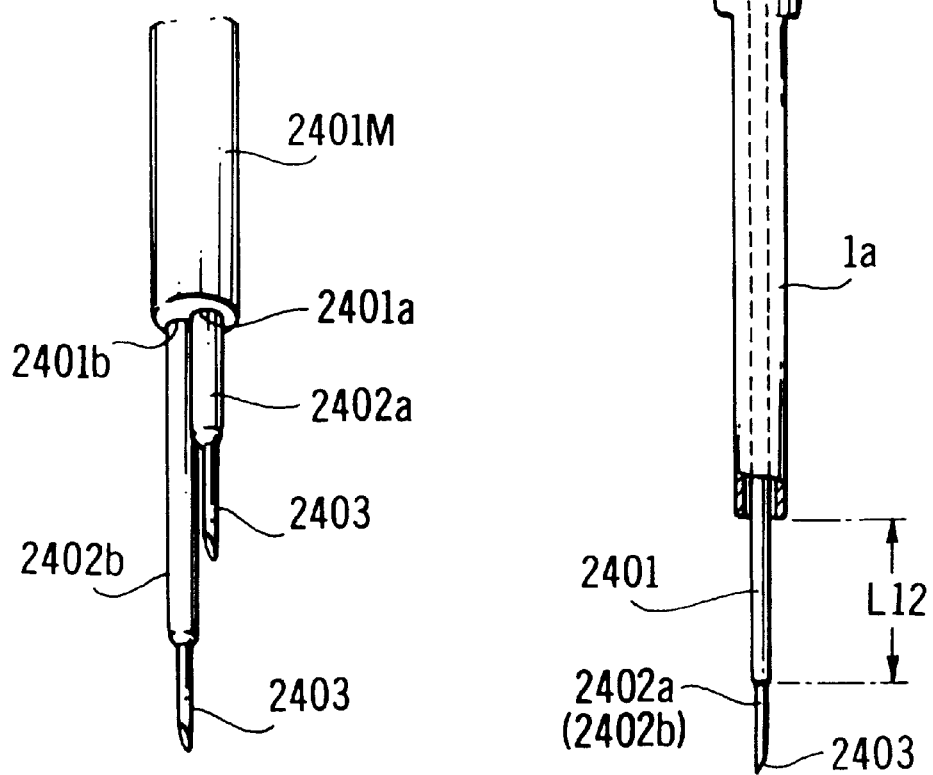
FIG. 77 is a perspective view of a modification to a cover tube of the injector instrument of FIG. 72 or FIG. 76.

FIG. 77 shows a modification of the seventeenth and eighteenth embodiments. In particular, the cover tube 2401 is replaced with a cover tube 2401M that is formed as a solid tube except for two channels 2401a and 2401b, which are formed through the whole length of the cover tube 2401M, to support the two fluid supply tubes 2402a and 2402b. According to this modification, the two fluid supply tubes 2402a and 2402b do not cross over each other inside the cover tube 2401M, allowing each needle portion 2403 to be stuck in target positions accurately and easily.

Further, when a second insertion is made, the cover tube 2401M may be revolved (by an operation at the end piece 2405) about its axis in order to easily position the second needle 2403.

In the modification described above, the two channels 2401a and 2401b are formed through the entire length of the cover tube 2401M, however, other alternatives are possible as long as the positional relation, in a cross section, between the two fluid supply tubes 2402a and 2402b inside the cover tube 2401M is maintained. For example, the cover tube 2401 may be hollow other than at predetermined portions which are provided with channels 2401a and 2401b to support the fluid supply tubes 2402a and 2402b.

Further alternatives to the structure defined in the seventeenth and eighteenth embodiments are also possible. For example, the number of fluid supply tubes inserted in the cover tube may also be three or more. In such a case, the channels described with regard to the modification may not need to be formed for all of the fluid supply tubes.

According to the seventeenth and eighteenth embodiments and modifications and alternative structures therefor, a procedure requiring multiple insertions of a needle or multiple injections is facilitated in that a second or later insertion or injection can be done without removing the needle used for the first injection or insertion, thereby avoiding problems caused by blood obscuring the target position(s).

FIG. 88 shows a forceps tap 2600 according to a nineteenth embodiment of the invention as applied to the endoscope 1.

The endoscope 1 includes an insertion portion 1a, and a manipulation portion 4 which is connected at a proximal end of the insertion portion 1a. A forceps channel 2, through which at least one treatment accessory 81 is inserted (in FIG. 88, a second treatment accessory 82 is also inserted), is formed inside the insertion portion 1a. The forceps channel 2 is formed through the whole length of the insertion portion 1a. The exit of the forceps channel 2 is at the distal end of the insertion portion 1a. The entrance of the forceps channel 2 is in the neighborhood of where the insertion portion 1a and the manipulation portion 4 are connected.

The forceps channel 2 has a diameter that is sufficiently large that two treatment accessories 81 and 82 can be inserted at the same time. At the entrance of the forceps channel 2, the forceps tap 2600 is detachably provided.

Figure 78:
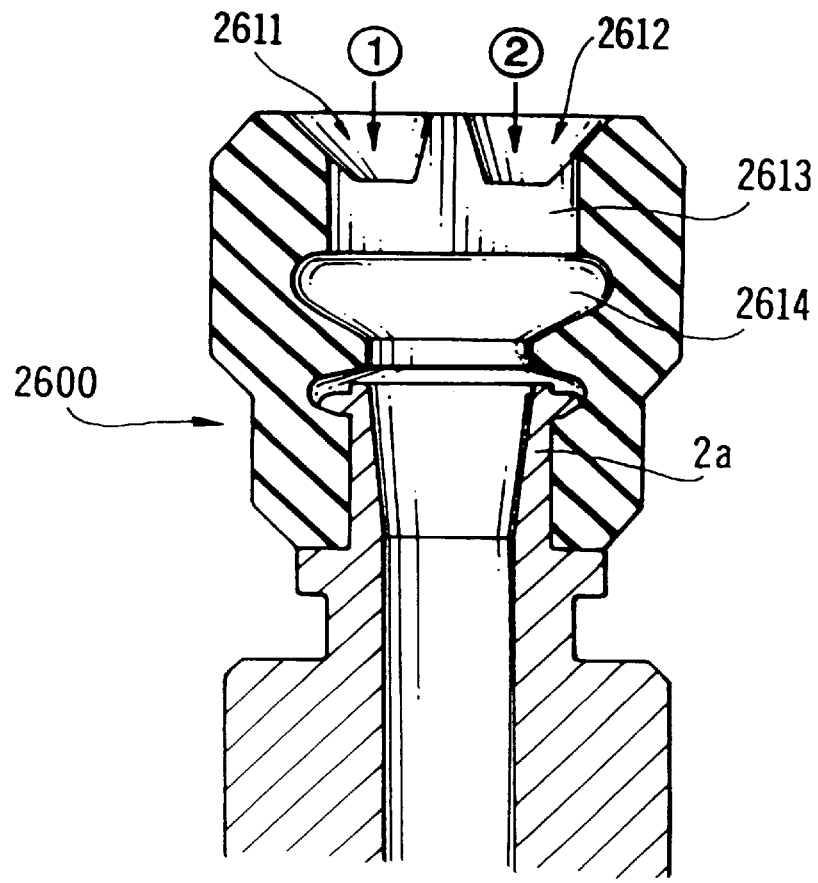
FIG. 78 is a sectional side view of a forceps tap according to a nineteenth embodiment of the invention attached at an entry to the forceps channel of the endoscope.

FIG. 78 shows an enlarged view of the forceps tap 2600 and the entrance of the forceps channel 2. A mouth piece 2a is provided at the entrance of the forceps channel 2. The mouth piece 2a is formed, for example, having the Luer-Lok shape. The forceps tap 2600 is coupled to the mouth piece 2a. The forceps tap 2600 is made of a synthetic rubber having hardness of 30–60, such as soft plastic or the like.

The forceps tap 2600 is attached to or removed from the mouth piece 2a by being elastically deformed. When attached, the forceps tap 2600 slightly squeezes the mouth piece 2a.

A top surface (upper side surface in FIG. 78) of the forceps tap 2600 is provided with treatment accessory guides 2611 and 2612, which are eccentrically bowl-shaped and do not pass through the upper surface of the forceps tap 2600. In particular, it is preferable that the central axis of each of the holes 2611 and 2612 is inclined in relation to the axis of the forceps tap 2600 (which is the same as the axis of the forceps channel 2) and crosses the axis of the forceps tap 2600 inside either of the forceps tap 2600 and the forceps channel 2.

Figure 79:
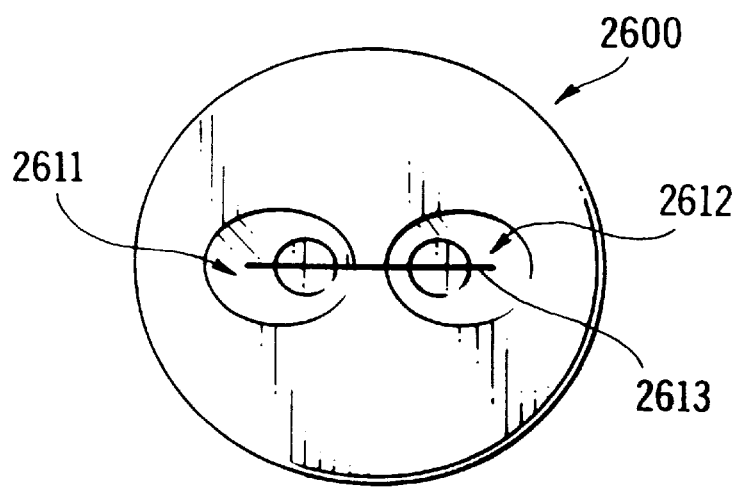
FIG. 79 is a top view of the forceps tap of FIG. 79.

FIG. 79 is a plan view of the forceps tap 2600. As shown in FIGS. 78 and 79, the upper surface of the forceps tap 2600 is formed or cut to have a straight slit 2613 passing through the upper surface of the forceps tap 2600 to an inner space 2614. The slit 2613 passes through the center of each of the treatment accessory guides 2611 and 2612 but does not reach the edges of the forceps tap 2600.

If no treatment accessories are inserted, due to elasticity, the slit 2613 remains closed and accordingly the entrance of the forceps channel 2 is elastically closed.

When two treatment accessories 81 and 82 are used, the treatment accessories 81 and 82 are inserted independently using the treatment accessory guides 2611 and 2612. The slit 2613 is opened by the insertion of the treatment accessories and the treatment accessories pass therethrough. If the treatment accessories are removed, the slit 2613 closes again due to elasticity.

Thus, two treatment accessories can be inserted through one forceps channel 2. In FIG. 88, as an example, both a grasping forceps instrument (treatment accessory 81) and a high frequency snare (treatment accessory 82) are inserted through the forceps channel 2 at the same time allowing, in this example, the cutting of a polyp to be done easily with a simple and inexpensive endoscope.

Figure 80:
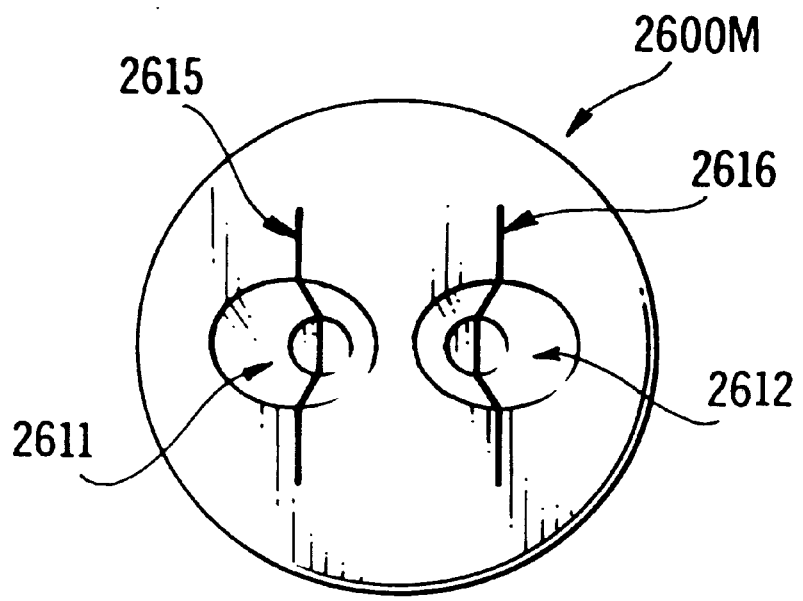
FIG. 80 is a top view of a modification of the forceps tap of FIG. 79.

FIG. 80 shows a top view of a forceps tap 2600M according to a modification wherein, instead of the slit 2613, a pair of slits 2615 and 2616 corresponding to the treatment accessory guides 2611 and 2612 are formed. In particular, the pair of slits 2615 and 2616 are parallel to each other. Substantially the same effect is obtained with the forceps tap 2600M.

Figure 81:
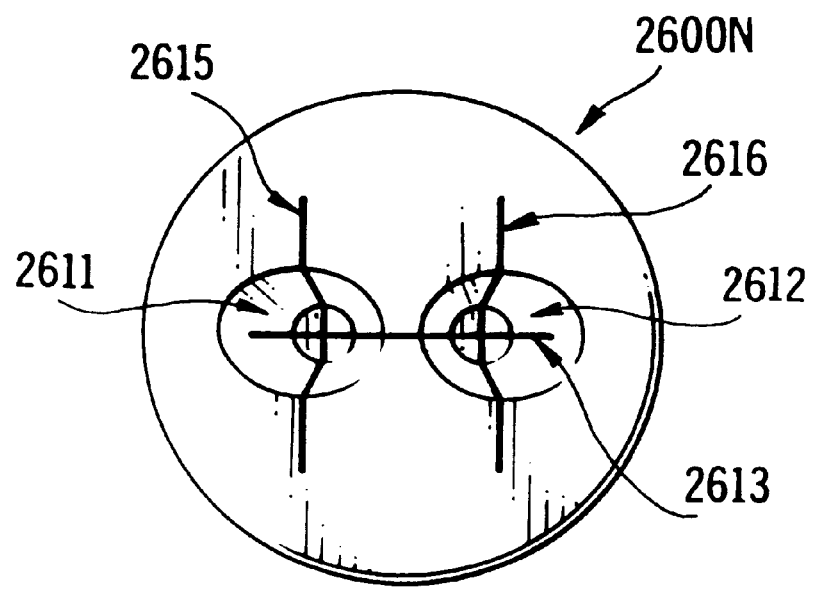
FIG. 81 is a top view of a modification of the forceps tap of FIG. 79.

FIG. 81 shows a top view of a forceps tap 2600N according to a modification, wherein the two parallel slits 2615 and 2616, and the one long slit 2613 which crosses the two parallel slits 2615 and 2616 at right angles are formed.

Figure 82:
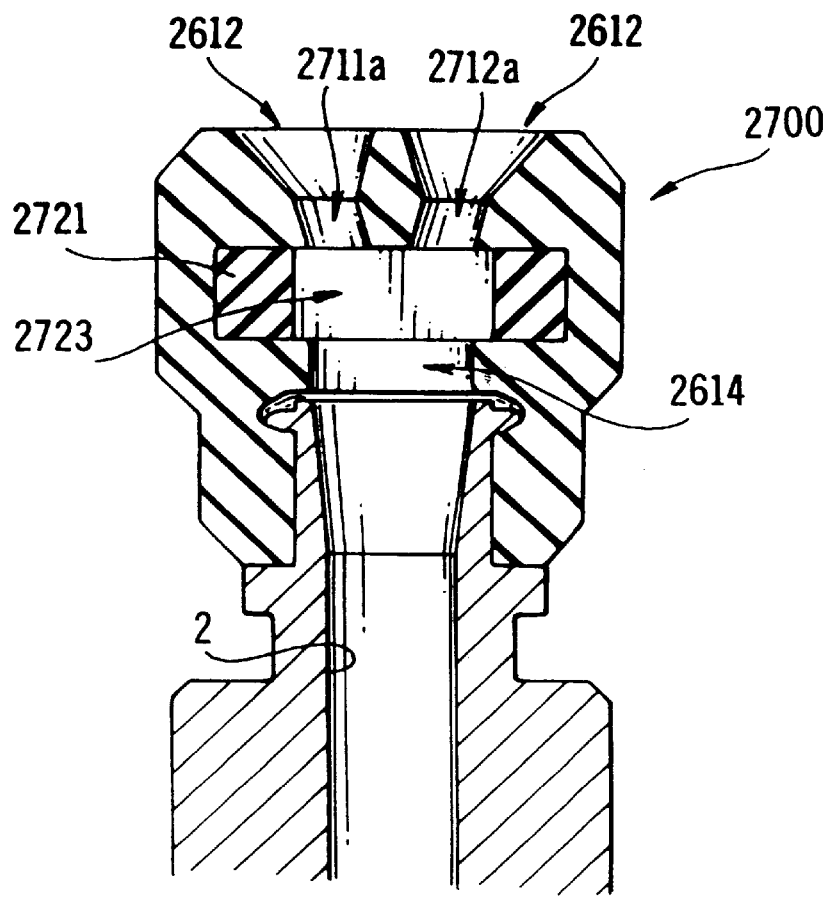
FIG. 82 is a sectional side view of a forceps tap according to a twentieth embodiment of the invention attached at an entry to the forceps channel of the endoscope.
Figure 83:
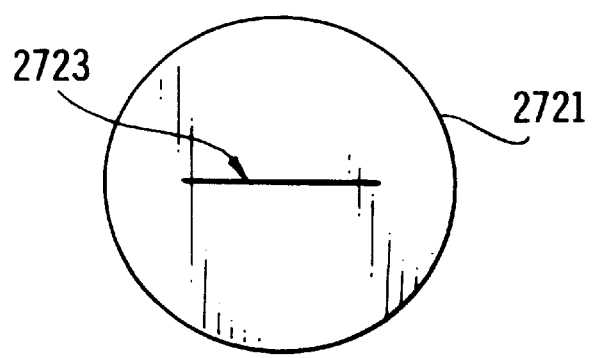
FIG. 83 is a top view of a packing of the forceps tap of FIG. 82.

FIG. 82 shows a schematic sectional side view of a forceps tap 2700 according to a twentieth embodiment of the invention at the entrance to a forceps channel 2. The forceps tap 2700 is similar to the forceps tap 2600 of the nineteenth embodiment. In this embodiment, a separate packing 2721 that is provided with a slit 2723 is fitted in the forceps tap 2700 between guide holes 2711a and 2712a, leading from the treatment accessory guides 2611 and 2612, to the inner space 2614. If this structure is employed, the packing 2721 can be made of a different material than that of the forceps tap 2700. Therefore, the packing 2721 may be made of, for example, independent foam sponge, providing decreased resistance against the insertion of the treatment accessory 81 when inserted through the slit 2723 and forming more closely around the treatment accessory 81 after insertion thereof. FIG. 83 shows a top view of the packing 2721.

Figure 84:
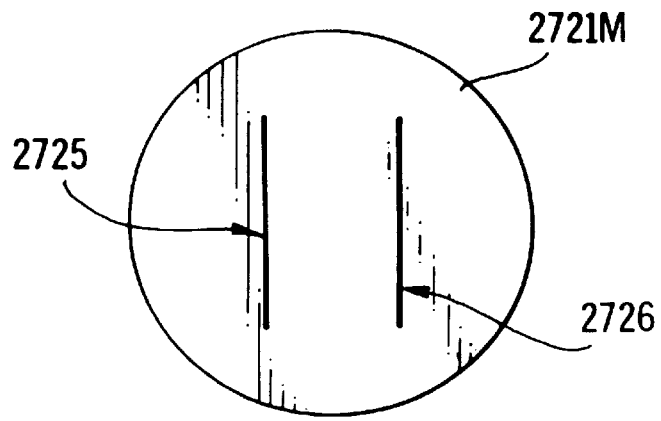
FIG. 84 is a top view of a modification of the packing of FIG. 83.

FIG. 84 shows a top view of a packing 2721M according to a modification wherein a pair of slits 2725 and 2726 are arrange parallel to each other and respectively correspond to the position of the guide holes 2711a and 2712a.

Figure 85:
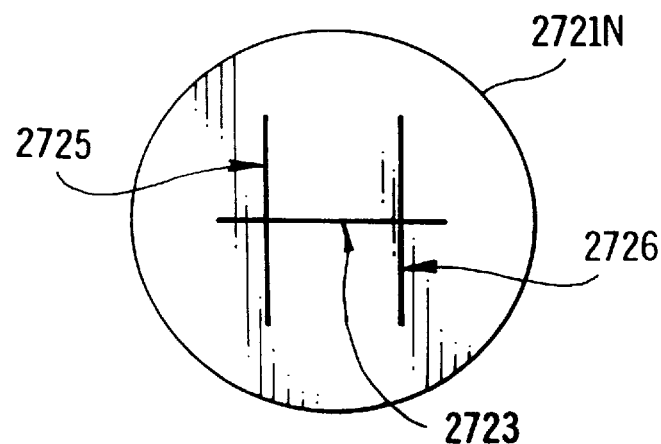
FIG. 85 is a top view of a modification of the packing of FIG. 83.

FIG. 85 shows a top view of a packing 2721N according to a further modification wherein both the slit 2723 and the slits 2725 and 2726 described above are formed.

Figure 86:
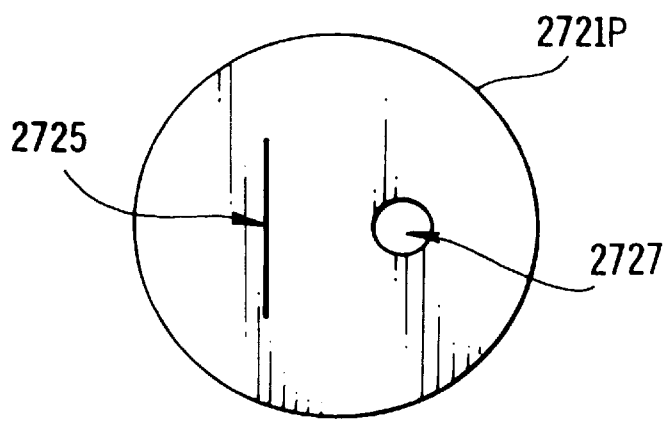
FIG. 86 is a top view of a modification of the packing of FIG. 83.

FIG. 86 shows a top view of a packing 2721P according to yet a further modification. If a cytology brush instrument is used as a treatment accessory 81, in order to avoid the scraping off of collected tissue cells by a slit (for example, the slit 2726 described above) of the packing 2721 during removal of the treatment accessory 81 or for some other particular purpose, a through hole 2727 is provided. In this case, although the through hole 2727 does not completely close the entrance of the forceps channel 2, the opened area is quite small in relation to the cross section of the forceps channel 2.

FIG. 87 shows a top view of a packing 2721Q according to a further modification. In this modification, two through holes 2727 and 2728 corresponding to the guide holes 2711a and 2712a are provided, for example, in order to decrease insertion and removal resistance.

It should be noted that the number of treatment accessory guides, guide holes, and corresponding slits and/or through holes is not limited to the above, and may be more than two.

According to the nineteenth and twentieth embodiments, a plurality of treatment accessories can be inserted in a single forceps channel, independently or simultaneously. Since no branching structure is needed in the manipulation portion, the size of the endoscope is not increased, even if a plurality of instruments are used. In particular, the size of the insertion portion of the endoscope is not increased such that a patient will not be subject to excess pain. Further, the number of forceps taps used is not increased.

Although the structure and operation of an injector instrument for an endoscope is described herein with respect to the preferred embodiments, many modifications and changes can be made without departing from the spirit and scope of the invention.

The present disclosure relates to subject matter contained in Japanese Patent Application No. HEI 07-140147, filed on Jun. 7, 1995, No. HEI 07-145934, filed on Jun. 13, 1995, No. HEI 07-174582, filed on Jul. 11, 1995, No. HEI 07-181337, filed on Jul. 18, 1995, No. HEI 07-199649, filed on Aug. 4, 1995, No. HEI 07-235161, filed on Sep. 13, 1995, No. HEI 07-251668, filed on Sep. 29, 1995, No. HEI 08-178782, filed on Jul. 9, 1996, No. HEI 08-178783, filed on Jul. 9, 1996, No. HEI 08-197491, filed on Jul. 26, 1996, No. HEI 09-22267, filed on Feb. 5, 1997, which are expressly incorporated herein by reference in their entirety.

What is claimed is:

1. An injector instrument for insertion into a forceps channel of an endoscope, said injector instrument comprising:
   a flexible fluid supply tube; and
   a needle portion formed at a distal end of said fluid supply tube, said needle portion being formed from a material having a hardness within a range of Rockwell hardnesses of R50 to R129.

2. The injector instrument according to claim 1, wherein said fluid supply tube and needle portion are integrally formed.

3. The injector instrument according to claim 1, said needle portion including an obliquely cut sharp tip.

4. The injector instrument according to claim 1, said needle portion including a sharp tip having two slanted planes.

5. The injector instrument according to claim 1, further comprising a mandrel member that is inserted into said fluid supply tube and said needle portion during insertion of said fluid supply tube and said needle portion into said forceps channel.

6. The injector instrument according to claim 1, wherein said hardness of said needle portion is greater than a hardness of a wall of said forceps channel.

7. The injector instrument according to claim 1, said needle portion including a stop element spaced from a distal end of said needle portion.

8. The injector instrument according to claim 1, said needle portion being a flexible resin.

9. The injector instrument according to claim 1, further comprising a cover tube, said fluid supply tube and needle portion being inserted into said cover tube.

10. The injector instrument according to claim 9, further comprising a detent element on said fluid supply tube, said detent element holding said needle portion in at least one position with respect to said cover tube.

11. The injector instrument according to claim 10, said detent element including an O-ring on said fluid supply tube and at least one groove on said cover tube.

12. The injector instrument according to claim 11, said at least one groove comprising two grooves spaced a predetermined distance apart, the needle portion having a movable distance within said cover tube which is less than said predetermined distance.

13. The injector instrument according to claim 10, said detent element including an O-ring on said cover tube and at least one groove on said fluid supply tube.

14. The injector instrument according to claim 9, further comprising a detent element on said cover tube, said detent element holding said needle portion in at least one position with respect to said cover tube.

15. The injector instrument according to claim 9, wherein at least two fluid supply tubes and needle portions are inserted into said cover tube.

16. The injector instrument according to claim 9, wherein said cover tube is a coiled wire.

17. The injector instrument according to claim 16, further comprising a metal tip portion at the distal end of said coiled wire.

18. The injector instrument according to claim 9, further comprising a manipulation element, said manipulation element moving said fluid supply tube within said cover tube.

19. The injector instrument according to claim 9, further comprising a mandrel member that is inserted into said fluid supply tube and said needle portion during insertion of said fluid supply tube and said needle portion into said cover tube.

20. The injector instrument according to claim 1, said fluid supply tube being formed to have a curved portion at a distal end portion when said fluid supply tube is in a neutral state.

21. The injector instrument according to claim 1, wherein said forceps channel is made of a material having a harnesses within a range of Shore hardnesses of D41 to D70.

* * * * *